United States Patent
Spence et al.

(10) Patent No.: US 9,504,523 B2
(45) Date of Patent: *Nov. 29, 2016

(54) SYSTEMS AND METHODS FOR TREATING THE HEART WITH ABLATION

(71) Applicant: SCR Inc., Louisville, KY (US)

(72) Inventors: Paul A. Spence, Louisville, KY (US); Sean Warren, Goshen, KY (US); Erica J. Wells, Jeffersonville, IN (US); Kurt Dierking, Louisville, KY (US); Daniel R. Bachman, Louisville, KY (US); Landon H. Tompkins, Louisville, KY (US)

(73) Assignee: SCR Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,739

(22) Filed: Nov. 9, 2015

(65) Prior Publication Data

US 2016/0058506 A1 Mar. 3, 2016

Related U.S. Application Data

(63) Continuation of application No. 13/386,268, filed as application No. PCT/US2010/044565 on Aug. 5, 2010, now Pat. No. 9,216,055.

(60) Provisional application No. 61/320,927, filed on Apr. 5, 2010, provisional application No. 61/294,609, filed on Jan. 13, 2010, provisional application No. 61/231,517, filed on Aug. 5, 2009.

(51) Int. Cl.
*A61B 18/18* (2006.01)
*A61B 18/14* (2006.01)
(Continued)

(52) U.S. Cl.
CPC .......... *A61B 18/1492* (2013.01); *A61M 25/09* (2013.01); *A61B 2018/00279* (2013.01); *A61B 2018/00351* (2013.01); *A61B 2018/00577* (2013.01); *A61M 2025/09183* (2013.01)

(58) Field of Classification Search
CPC ............... A61B 18/1492; A61B 2018/00279; A61B 2018/00577; A61M 25/09

USPC ........................................ 606/32, 39, 41, 49
See application file for complete search history.

(56) References Cited

U.S. PATENT DOCUMENTS 5,499,632 A * 3/1996 Hill, III .......... A61M 25/09041
600/434
5,575,766 A 11/1996 Swartz et al.
(Continued)

FOREIGN PATENT DOCUMENTS

CN 1181790 A 5/1998
CN 1259852 A 7/2000
(Continued)

OTHER PUBLICATIONS

U.S. Patent and Trademark Office, International Search Report and Written Opinion in PCT Application Serial No. PCT/US2010/044565, Sep. 29, 2010.
(Continued)

*Primary Examiner* — Christopher D Koharski
*Assistant Examiner* — Michael Carey
(74) *Attorney, Agent, or Firm* — Wood Herron & Evans LLP

(57) ABSTRACT

A system for ablating internal heart tissue in an ablation pattern on a surface of the tissue within the heart. The system includes an ablation catheter with a distal end having an ablating tip portion operative to allow selective ablation of tissue. A guiding device is engageable with the ablation catheter and includes a tissue anchoring portion operable to engage with tissue proximate to the tissue to be ablated so as to temporarily anchor the guiding device relative to the tissue. Engagement of the guiding device with the ablation catheter operates to assist with guiding the ablating tip portion in moving along the pattern. Various devices and methods of use are further disclosed.

15 Claims, 77 Drawing Sheets

(51) Int. Cl.
*A61M 25/09* (2006.01)
*A61B 18/00* (2006.01)

(56) References Cited

U.S. PATENT DOCUMENTS

| | | | |
|---|---|---|---|
| 5,738,683 A | 4/1998 | Osypka | |
| 5,741,249 A | 4/1998 | Moss et al. | |
| 5,879,295 A | 3/1999 | Li et al. | |
| 5,885,278 A * | 3/1999 | Fleischman | A61B 18/1492 600/374 |
| 5,902,289 A | 5/1999 | Swartz et al. | |
| 6,138,043 A | 10/2000 | Avitall | |
| 6,146,379 A | 11/2000 | Fleischman et al. | |
| 6,235,021 B1 | 5/2001 | Sieben | |
| 6,241,754 B1 | 6/2001 | Swanson et al. | |
| 6,471,699 B1 | 10/2002 | Fleischman et al. | |
| 6,585,733 B2 | 7/2003 | Wellman | |
| 6,595,989 B1 * | 7/2003 | Schaer | A61B 17/2004 606/41 |
| 6,652,517 B1 | 11/2003 | Hall et al. | |
| 6,771,996 B2 | 8/2004 | Bowe et al. | |
| 6,773,433 B2 | 8/2004 | Stewart et al. | |
| 6,899,711 B2 | 5/2005 | Stewart et al. | |
| 6,949,097 B2 | 9/2005 | Stewart et al. | |
| 7,052,492 B2 | 5/2006 | Swanson et al. | |
| 7,128,740 B1 | 10/2006 | Jacobs et al. | |
| 7,294,143 B2 | 11/2007 | Francischelli | |
| 7,331,959 B2 * | 2/2008 | Cao | A61B 18/1492 606/41 |
| 7,338,486 B2 | 3/2008 | Sliwa et al. | |
| 7,340,307 B2 | 3/2008 | Maguire et al. | |
| 7,413,568 B2 | 8/2008 | Swanson et al. | |
| 7,419,489 B2 | 9/2008 | Vanney et al. | |
| 7,474,909 B2 | 1/2009 | Phan et al. | |
| 9,216,055 B2 * | 12/2015 | Spence | A61B 18/1492 |
| 2002/0019627 A1 | 2/2002 | Maguire et al. | |
| 2002/0111618 A1 | 8/2002 | Stewart et al. | |
| 2003/0051362 A1 | 3/2003 | Buckman et al. | |
| 2003/0135207 A1 | 7/2003 | Langberg et al. | |
| 2003/0195510 A1 | 10/2003 | Schaer | |
| 2004/0034347 A1 | 2/2004 | Hall et al. | |
| 2004/0059327 A1 | 3/2004 | Jenkins et al. | |
| 2004/0167510 A1 | 8/2004 | Feld et al. | |
| 2004/0215186 A1 | 10/2004 | Cornelius et al. | |
| 2004/0243107 A1 | 12/2004 | Macoviak et al. | |
| 2005/0159742 A1 | 7/2005 | Lesh | |
| 2005/0267460 A1 | 12/2005 | Roop et al. | |
| 2007/0038056 A1 | 2/2007 | Pappone et al. | |
| 2007/0043296 A1 | 2/2007 | Schwartz | |
| 2007/0219546 A1 | 9/2007 | Mody et al. | |
| 2007/0265610 A1 | 11/2007 | Thapliyal et al. | |

FOREIGN PATENT DOCUMENTS

| | | |
|---|---|---|
| CN | 1269708 A | 10/2000 |
| DE | 10037660 A1 | 2/2002 |
| EP | 1042990 A1 | 10/2000 |
| WO | 2007134258 A2 | 11/2007 |
| WO | 2010039443 A1 | 4/2010 |

OTHER PUBLICATIONS

Chinese Patent Office, Office Action in CN Application No. 2010800426625, Mar. 5, 2014.

Chinese Patent Office, Office Action in CN Application No. 2010800426625, Dec. 25, 2014.

* cited by examiner

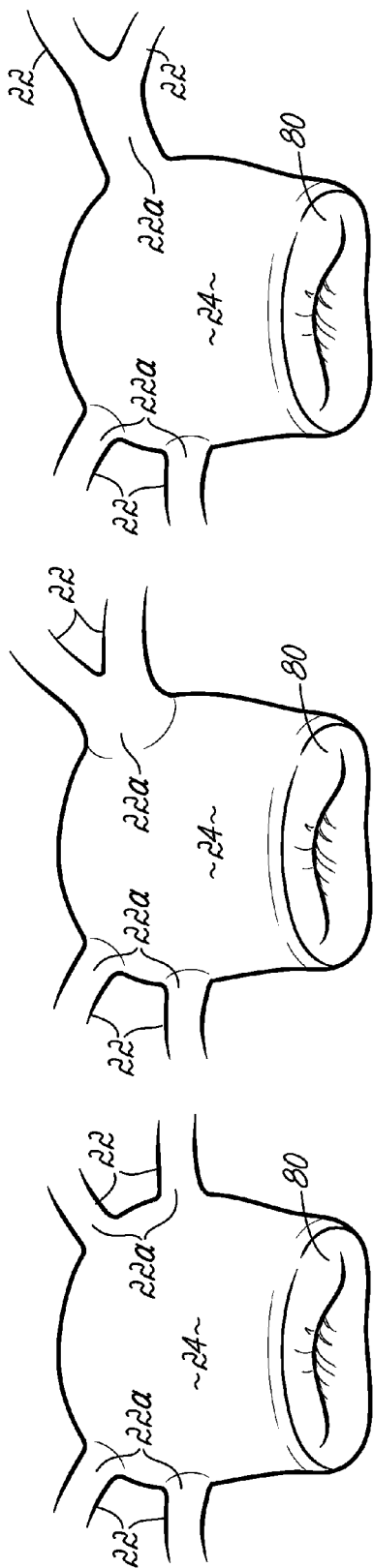

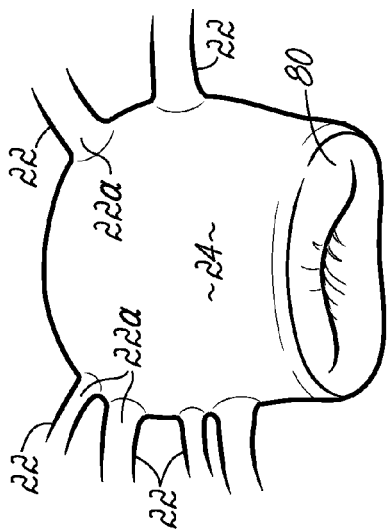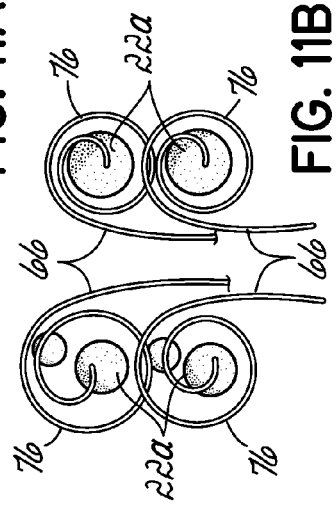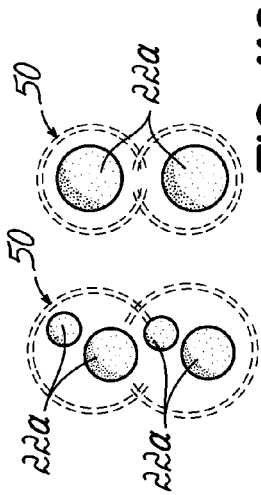
FIG. 9A  FIG. 10A  FIG. 11A
FIG. 9B  FIG. 10B  FIG. 11B
FIG. 9C  FIG. 10C  FIG. 11C

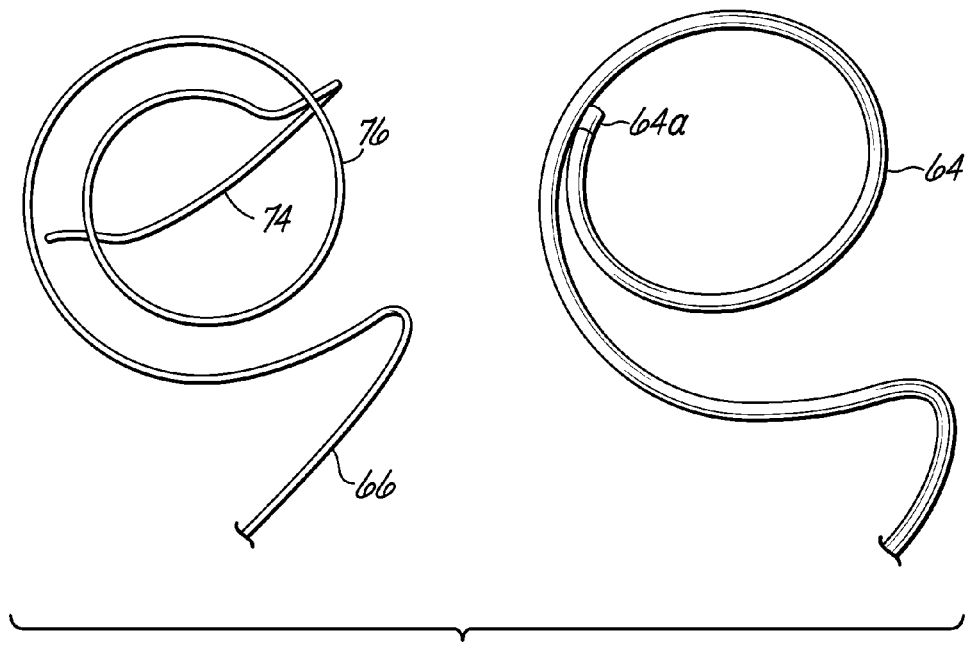
FIG. 13A
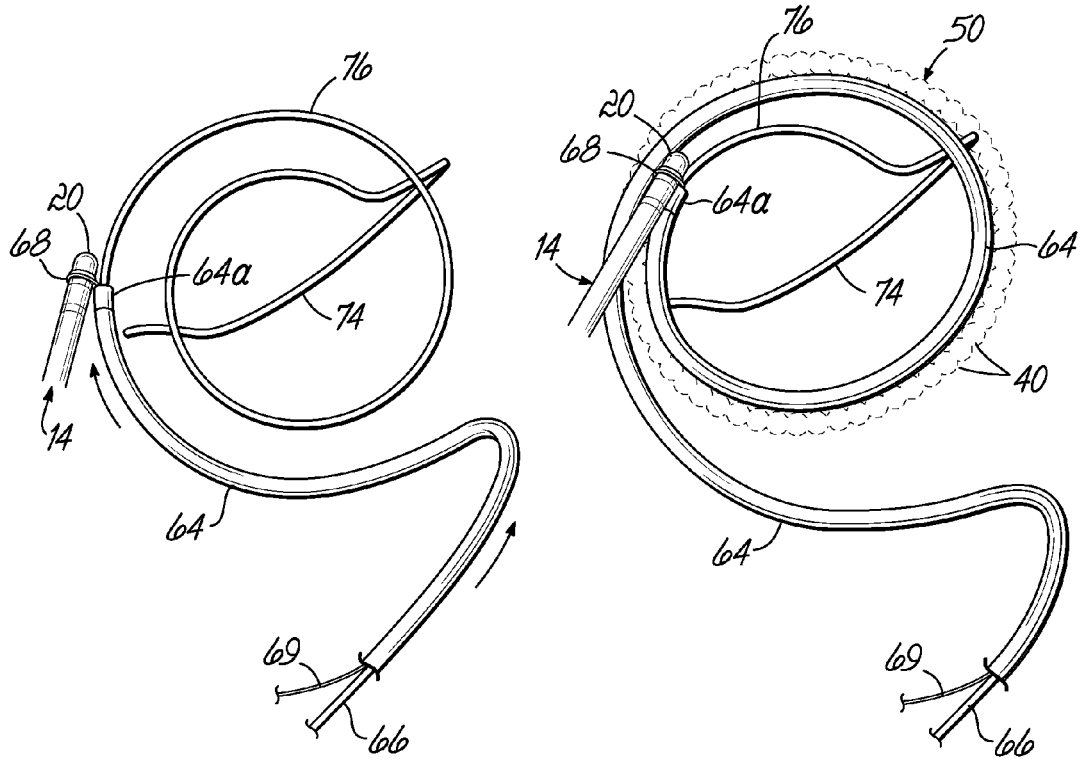
FIG. 13B
FIG. 13C

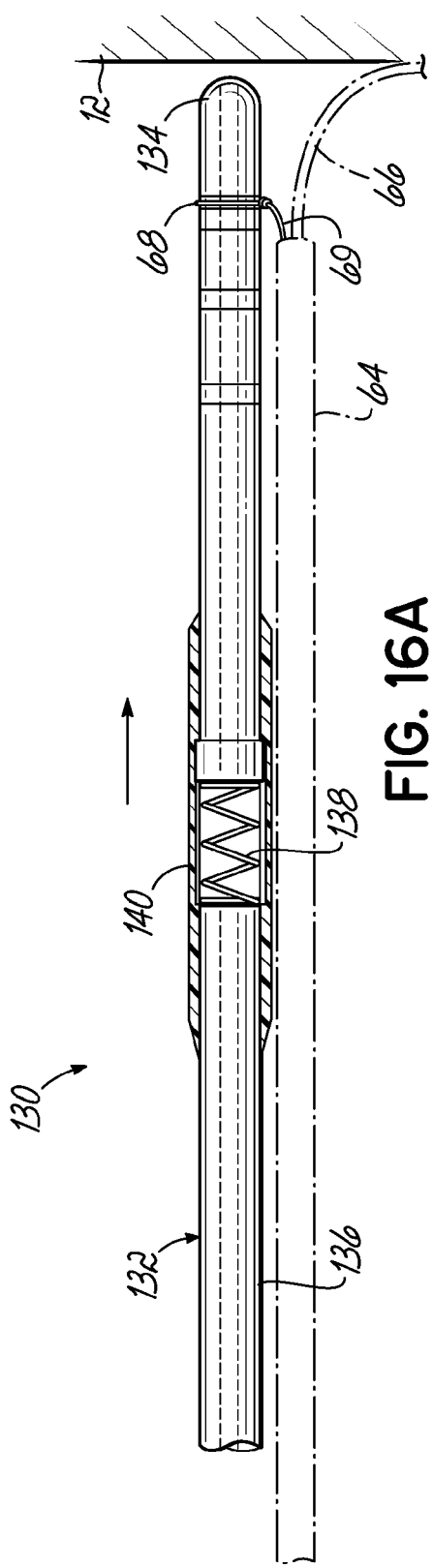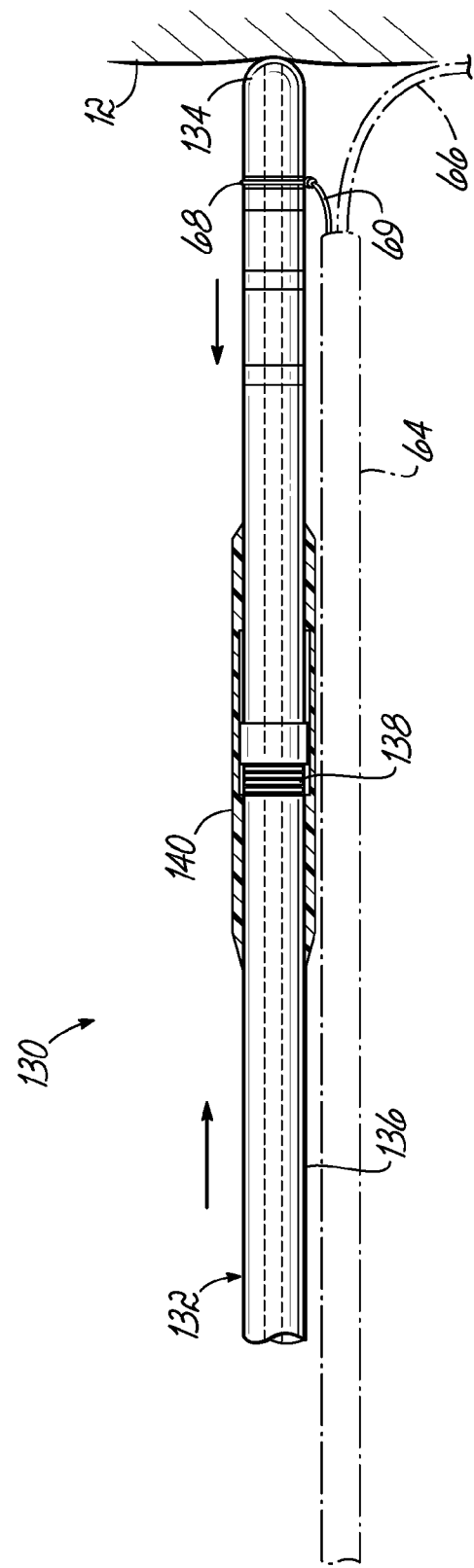
FIG. 16A
FIG. 16B

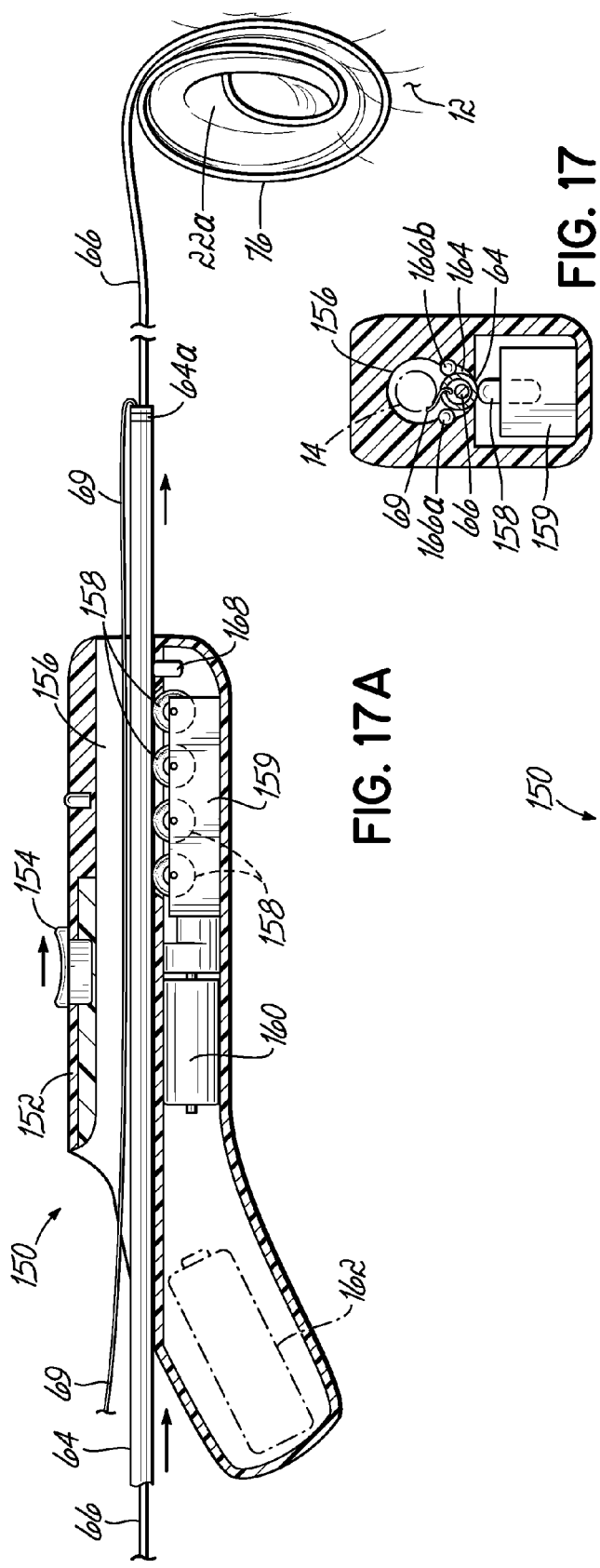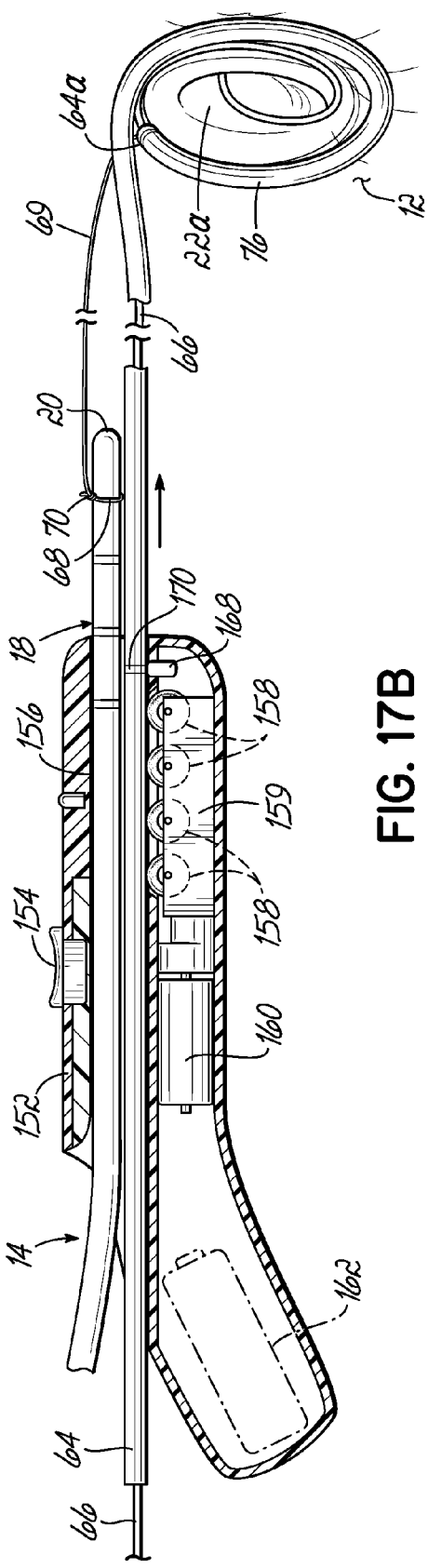
FIG. 17A
FIG. 17
FIG. 17B

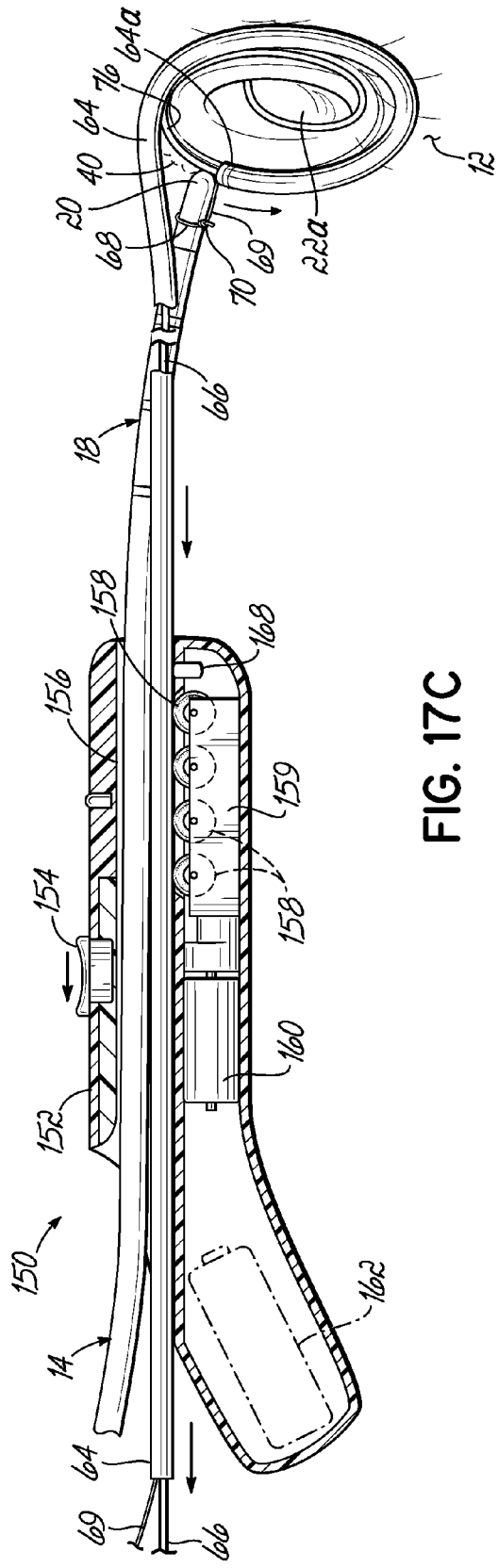
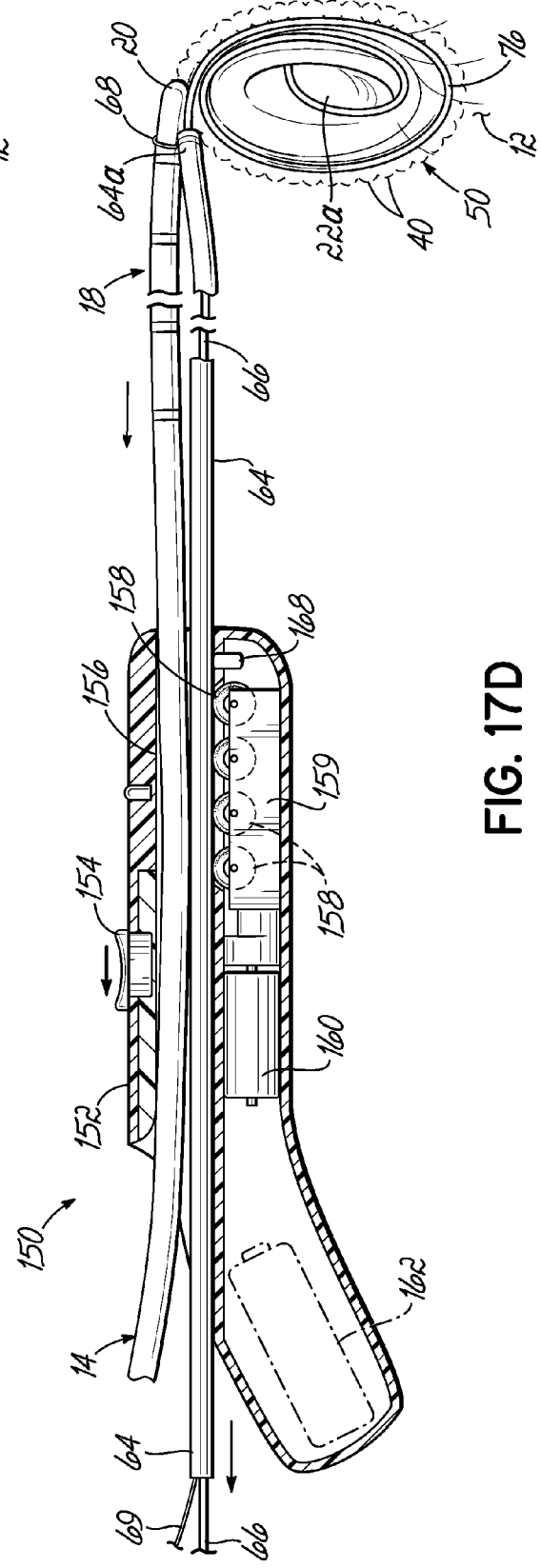
FIG. 17C
FIG. 17D

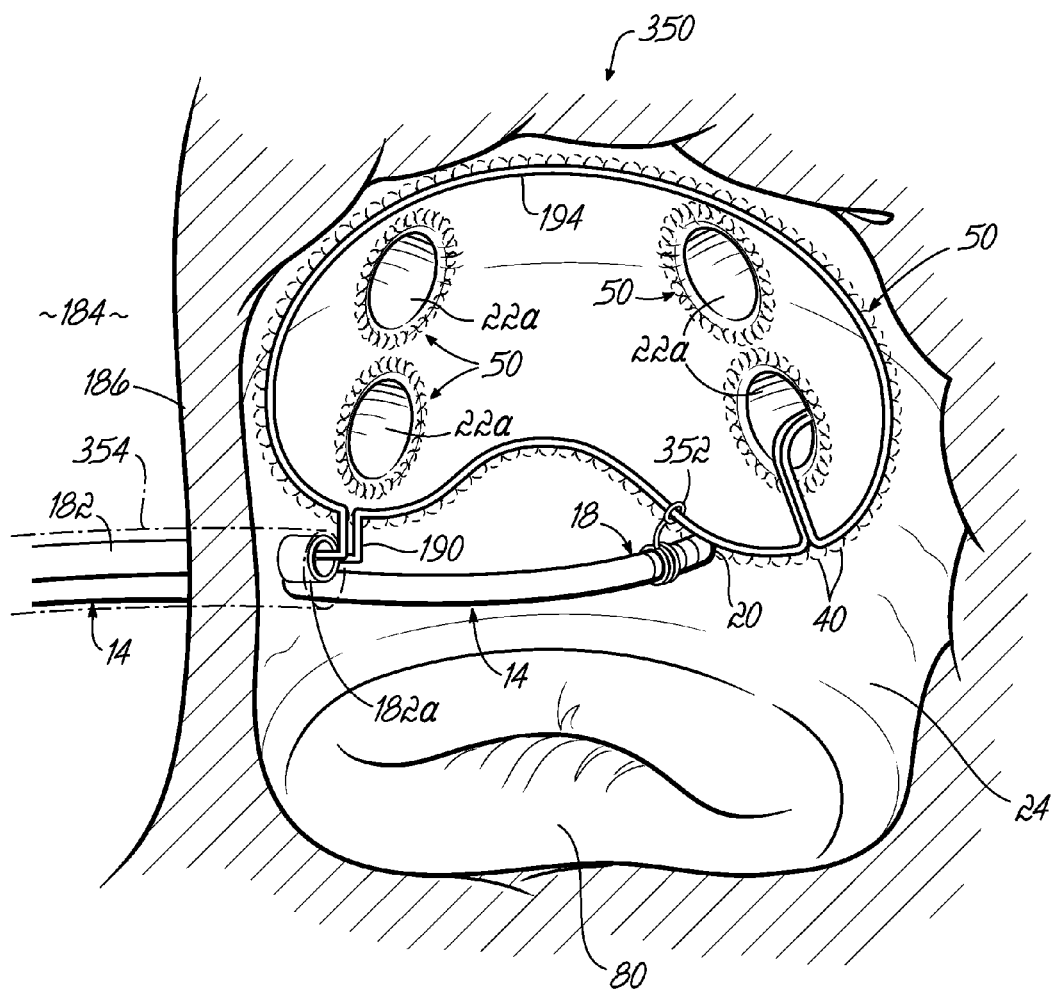
FIG. 28
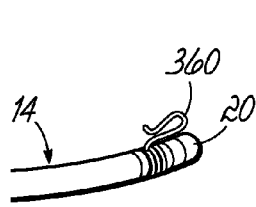
FIG. 29A   FIG. 29B
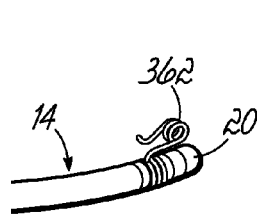
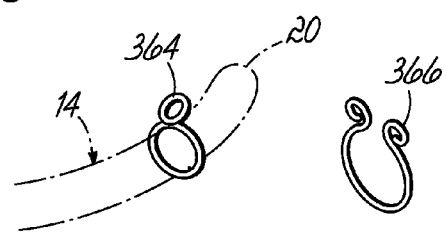
FIG. 29C   FIG. 29D

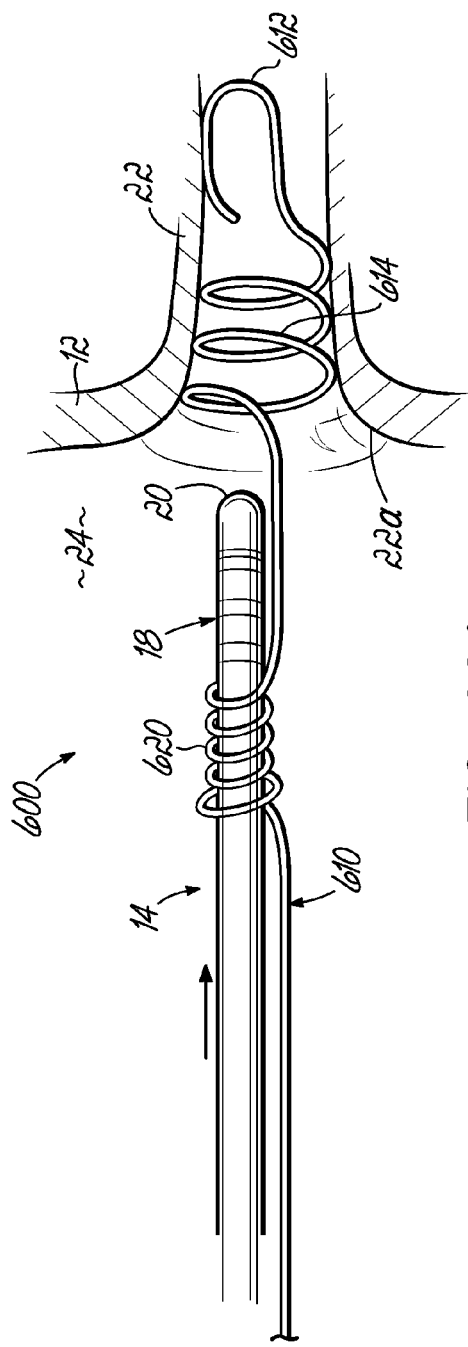
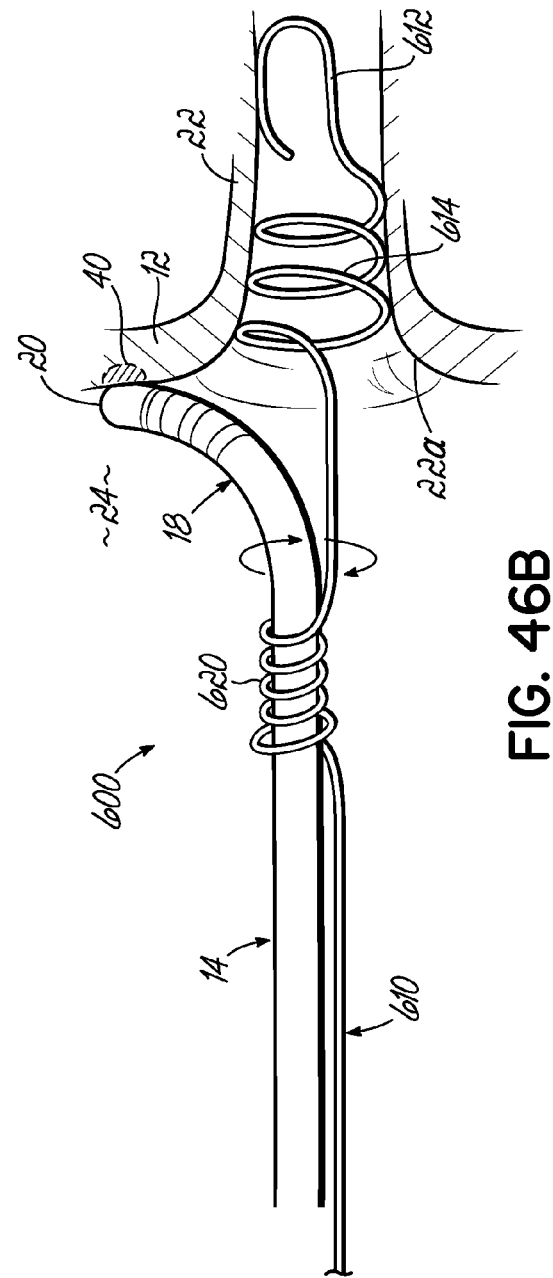
FIG. 46A
FIG. 46B

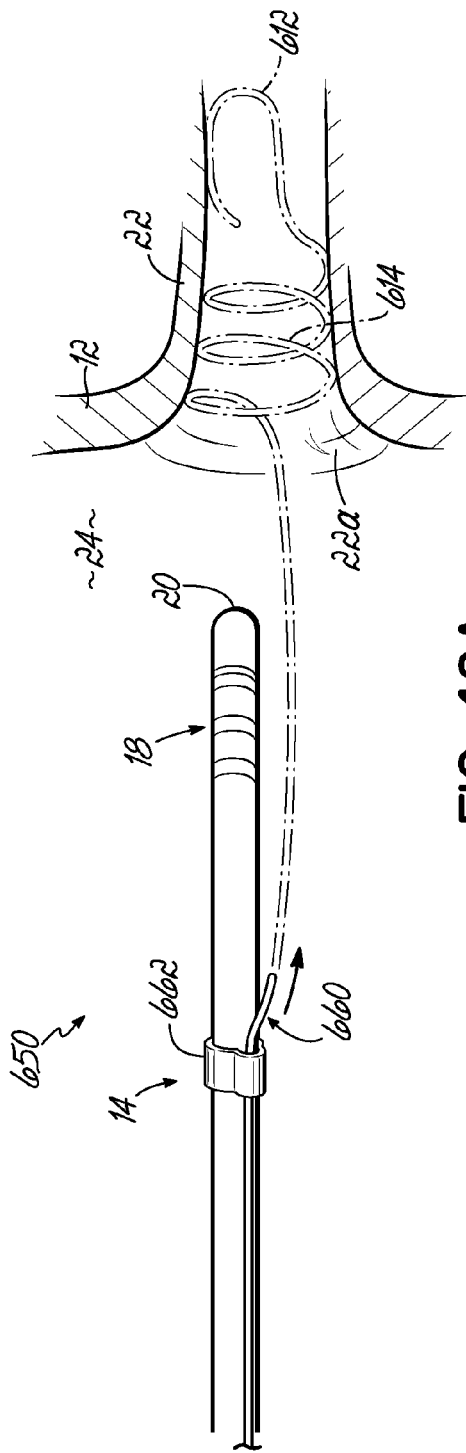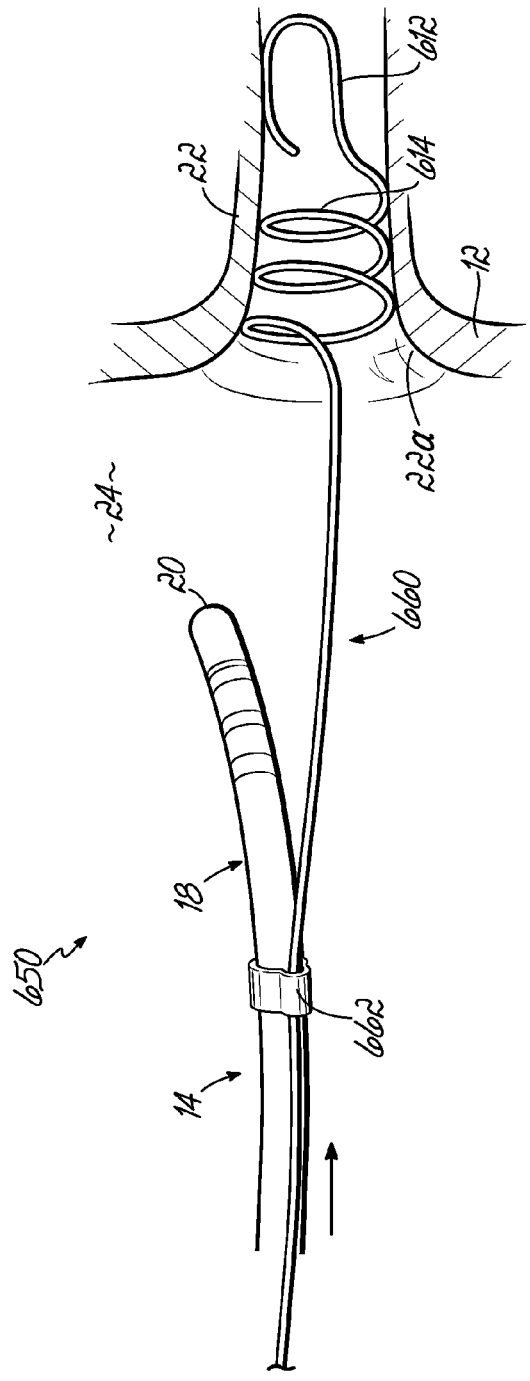
FIG. 48A
FIG. 48B

SYSTEMS AND METHODS FOR TREATING THE HEART WITH ABLATION

CROSS-REFERENCE TO RELATED APPLICATIONS

This application is a continuation of U.S. application Ser. No. 13/386,268 filed Apr. 3, 2012 (now U.S. Pat. No. 9,216,055), which is a U.S. National Phase Application of PCT Serial No. PCT/US2010/044565, filed Aug. 5, 2010 (expired), which claims the benefit of U.S. Provisional Patent Application Ser. No. 61/231,517, filed Aug. 5, 2009, 61/294,609, filed Jan. 13, 2010, and 61/320,927, filed Apr. 5, 2010 the disclosures of which are incorporated by reference herein.

TECHNICAL FIELD

The present invention generally relates to ablation systems, devices and techniques for treating the heart.

BACKGROUND

Various methods have evolved for treating atrial fibrillation (AF) and/or other arrhythmias of the heart and many include the use of ablation techniques. Various types of devices are used for treating heart tissue and forming lesions in selected areas of the heart for this purpose. Early techniques involved open surgery and small incisions in the heart tissue along selected paths designed to disrupt the pathway of disruptive electrical circuits leading to an abnormal sinus rhythm. Since the incisional scars left by this procedure produced a maze-like pattern, the procedure was referred to as the "maze" procedure. Since the early procedures involved open surgery, and heart-lung bypass, the surgery presented the usual risks, long recovery time, and pain. Over time, ablation devices using various forms of energy, such as radiofrequency (RF), cryotherapy, ultrasound, laser, and microwave, have been developed and used in open surgical procedures, and also in less invasive procedures for ablating tissue of the right and left atrial chambers. These ablation techniques form lesions and, ultimately, scar tissue in the heart designed to promote normal heart rhythm in the manner generally as previously performed with incisions.

Catheter ablation techniques typically use relatively low levels of energy that are capable of creating lesions in tissue sufficient to block abnormal electrical pathways within the tissue. For example, treating chronic AF has involved forming numerous lesions in the heart tissue, with the lesions extending completely through the tissue to provide more complete blockage of electrical pathways. Electrophysiologists often create these lesions using the ablating tip portion of an ablation catheter. This will be an electrode in the case of an RF ablation catheter. Such catheters are configured to create spot lesions and, in order for the electrophysiologist to form linear (straight or curved) and/or closed geometric shapes of scar tissue, such as is required for standard maze procedures, the electrophysiologist must make a series of connected spot lesions with the ablation catheter.

Percutaneous treatment is preferred because it may be used on a beating heart and therefore avoids heart-lung bypass and other disadvantages of open surgery. Catheter ablation techniques typically involve mapping the tissue surface of the left atrium with a sensing catheter and other equipment. Electro-anatomic mapping has also been developed which utilizes a GPS system allowing the electrophysiologist to register points on a GPS map. The electrophysiologist ablates tissue and forms lesions in continuous and surrounding patterns, for example, around the pulmonary veins and in other locations. Standard lesion sets include: 1) isolation of the pulmonary veins in the wall of the left atrial chamber or atrium, each being isolated individually or in pairs including isolating the left superior and inferior veins together and isolating the right superior and inferior veins together, 2) a box lesion or four vein isolation in which a closed pattern of lesions is formed around all four of the veins in the atrial chamber, and 3) a pattern of lesions in the atrial wall leading from the box lesion to the mitral valve. Depending on the needs of the patient and the doctor's treatment plan, the lesion patterns may differ.

Catheters have been developed having more complicated designs including, for example, multiple electrodes for forming circular lesions in surrounding relation to the openings of the pulmonary veins in the left atrium. However, these catheters present challenges in use and can present complications and low efficacy as compared to prior techniques.

It would be desirable to provide improved systems, devices and methods for forming the patterns of lesions using an ablation catheter in a percutaneous treatment of the heart designed to promote normal sinus rhythm.

SUMMARY

The present invention generally provides a system for ablating internal heart tissue in a lesion pattern on a surface of the tissue within the heart of a patient. Typically, the lesions will be formed in the left atrium, but it may be desirable to form lesions in other areas of the heart, such as the right atrium. The pattern(s) may take many different forms, such as one or more of the forms discussed above, or any other form that is designed to promote normal sinus rhythm. This includes the more specific treatment and cure for atrial fibrillation or AF.

The system generally comprises an ablation catheter including a distal end, with the distal end including an ablating tip portion operative to allow selective ablation of tissue. This ablation catheter may take many different forms, and may utilize many different types of energy for purposes of effecting the ablation. The energy may, for example, be radiofrequency energy, thermal energy, cryogenic energy, laser or microwave energy. The system further includes a guiding device engageable with the ablation catheter. The guiding device includes a tissue anchoring portion operable to engage with tissue proximate to the tissue to be ablated so as to temporarily anchor the guiding device relative to the tissue to be ablated. Engagement of the guiding device with the ablation catheter is operable to assist with guiding the ablating tip portion in moving along the pattern designed to promote normal sinus rhythm of the heart. In general, the engagement of the guiding device with the ablation catheter may or may not include a direct or indirect physical connection between the ablation catheter and the guiding device. If there is no direct or indirect physical connection between the ablation catheter and the guiding device, for example, the ablating tip portion of the ablation catheter may be contacted with the guiding device, such as the template portion of a template wire, as the ablating tip is moved or indexed therealong to create the desired pattern of lesions. The lesions may be, for example, a series of connected spot lesions or one or more elongated lesions.

In one form, the guiding device further comprises a positioning catheter operatively coupled with the ablation catheter and further coupled with a template wire. The positioning catheter is movable along a distal end portion of the template wire to assist with applying at least a portion of the pattern. In another form, the guiding device comprises a wire that is engageable with the ablation catheter by way of a coupling that extends laterally relative to a proximally located main, lengthwise axis of the wire. The coupling allows the ablating tip portion of the ablation catheter to be moved about or around the tissue anchoring portion to apply at least a portion of the ablation pattern. In the case of using a wire as at least part of the guiding device, the tissue anchoring portion may be formed using a distal tip portion of the wire, although it may be disposed at other locations at the distal portion of the wire. Also, while it is preferred that the tissue anchoring portion be formed integrally from the wire, it may be a separately connected portion instead, as may other portions of the wire. The tissue anchoring portion may include a portion configured to extend into and temporarily anchor within a pulmonary vein communicating with the atrial chamber. This anchoring portion may comprise a section of the wire that extends laterally relative to the main, long axis of the wire at a more proximal location thereof. This laterally or transversely extending portion may be formed in many different shapes including, for example, hook or J-shapes, U-shapes and/or coil shapes.

The guiding devices may be attached to the ablation catheter in a manner that allows limited movement of the ablating tip portion toward and away from the tissue in order to maintain proper contact with and force against three dimensional variations in the tissue surface. The template wire may be configured into a generally closed geometric shape so that the pattern of ablation is also applied and lesions are formed in a closed, geometric shape by following the ablating tip portion along the template wire. More specifically, the template wire may be configured into a shape configured to surround one or more pulmonary vein locations in the left atrium. The template wire may also carry one or more markers, such as radiopaque markers, and/or sensors, such as electrodes, operative to assist with location and/or testing of the effectiveness of the ablation. The template wire may further comprise a double wire track configured to receive and guide the ablating tip portion between two wire portions of the track. For coupling the ablation catheter for movement relative to the template wire, the ablation catheter may further include a coupling, such as a wire segment, that is capable of being actuated to selectively couple with the template wire, such as by coiling around the template wire, in order to connect the ablating tip portion to the template wire in a manner allowing movement of the ablating tip portion relative to the template wire. The ablation catheter may further include a guide channel and the guiding device may further include a template wire extending through the guide channel. In this case, the ablation catheter is movable along the template wire to apply at least a portion of the pattern. A template wire may be preformed with a three dimensional shape including a tissue anchoring portion and a template portion along which the ablation catheter is guided and the channel can further comprise a lumen extending lengthwise through the ablation catheter. The template wire transforms from a straightened condition in the lumen of the ablation catheter to a three dimensional shape as or after the template wire is extended outwardly from a distal end of the ablation catheter. This transformation may occur due to the bias inherent in the material or materials used to form the template wire, or may occur when energy is applied as in the case of using a shape memory alloy, or by other mechanical means. In another alternative, superelastic materials may be used, such as NiTi, to facilitate this function. The template wire may have at least two areas of stiffness along the length thereof that are different from each other at the distal end portion. Although the entire template wire is preferably flexible such that it may be suitably directed through a catheter, for example, the tissue anchoring portion may be more flexible than more proximal portions, such as the portion serving as a template to guide the ablating tip portion of the ablation catheter. The increased flexibility of the tissue anchoring portion, relative to the template portion, can help prevent puncturing or damage to the heart tissue during insertion of the tissue anchoring portion into a pulmonary vein, for example, or during other manipulation of the wire within the heart during a procedure. A motor drive unit may be provided and operatively coupled to the ablation catheter so as to move the ablating tip portion along the pattern. This would provide a more automated method of treatment. This operative coupling may be a direct or indirect coupling.

In another aspect, the system includes an ablation catheter as generally discussed above, and a template wire connected with a direct or indirect connection with the ablation catheter. The template wire includes a tissue anchoring portion operable to engage with tissue proximate to the tissue to be ablated so as to temporarily anchor the template wire relative to the tissue to be ablated. The template wire further includes a template portion generally having a shape corresponding to at least a portion of the ablation pattern. The direct or indirect connection between the template wire and the ablation catheter allows the ablating tip portion to be guided and moved along the template portion to apply at least a portion of the pattern. In the embodiments including a template portion of the wire, the template portion extends in a lateral or transverse direction relative to a main, lengthwise axis of the wire at a more proximal location on the wire.

In another aspect, the system includes an ablation catheter as generally discussed above, and a guiding device comprising a wire including a tissue anchoring portion operable to engage the tissue at an anchoring location proximate to the tissue to be ablated so as to temporarily anchor the wire relative to the tissue to be ablated. The wire is connected with the ablation catheter by way of a coupling that extends laterally or transversely to a main, lengthwise axis of a more proximal portion of the wire. The coupling allows movement, such as generally a rotation of the ablating tip portion in an arch or curved pattern, around the anchoring location to apply at least a portion of the ablation pattern. In this aspect, the wire guiding device may include a coiled portion or a channel or ring-shaped coupling, and the ablation catheter extends through the coupling to connect the wire guiding device to the ablation catheter allowing the relative movement between the ablation catheter and the wire guiding device. The tissue anchoring portion may further comprise a portion configured to extend into and temporarily anchor with a pulmonary vein.

In another aspect, an ablation catheter is provided and includes an elongate catheter portion having a distal end portion with an ablating tip portion and a second portion operatively coupled to the ablating tip portion so as to allow relative axial movement between the second portion and the ablating tip portion. In this manner, a user may apply axial force to the distal end portion during an ablation procedure and the second portion will move axially relatively to the ablating tip portion thereby indicating an amount of axial force applied by the user. This will assist with indicating to the user the amount of energy applied to the tissue for effective transmural ablation. The second portion and the ablating tip portion may lie along a common axis and a compressible portion of the catheter may be positioned between the ablating tip portion and the second portion for allowing the relative axial movement.

In another aspect, a percutaneous method of treating the heart to promote normal sinus rhythm is provided and generally comprises directing an ablation catheter including a distal end percutaneously into the vascular system including the heart of a patient, with the distal end including an ablating tip portion operative to allow selective ablation of tissue. A guiding device is percutaneously directed into the vascular system either with or separately from the ablation catheter and is also directed into the heart. The guiding device is temporarily anchored on tissue proximate to the tissue to be ablated. The ablating tip portion is guided with the aid of the guiding device while ablating heart tissue along a pattern designed to promote normal sinus rhythm of the heart, such as by treating atrial fibrillation with a maze pattern of lesions.

The guiding device may further comprise a positioning catheter operatively coupled with the ablation catheter and further coupled with a template wire. Guiding the ablating portion may then further comprise moving the positioning catheter along a template portion of the template wire at the distal end of the wire to assist with applying at least a portion of the pattern. The method may further comprise temporarily anchoring the guiding device by anchoring a distal tip portion of the template wire. Temporarily anchoring the distal tip portion may further comprise inserting and anchoring the distal tip portion into a pulmonary vein. The guiding device may be attached to the ablation catheter in a manner that allows limited movement of the ablating tip portion toward and away from the tissue and guiding the ablation tip portion may further comprise maintaining proper contact with and ablation of three dimensional variations in the tissue surface by moving the ablating tip portion toward and away from the guiding device. The template wire may be configured into a generally closed geometric shape and guiding the ablating tip portion may further comprise applying an ablation pattern having a closed geometric shape. Guiding the ablating tip portion may further comprise applying a pattern of ablation in a shape surrounding one or more pulmonary vein locations in the left atrium. The ablating tip portion of the ablation catheter may be sensed while guiding the ablating tip portion, such as with radiopaque markers or electronic sensors. Effectiveness of the ablation pattern may be tested with sensors located on the guiding device and/or on the ablation catheter. The template wire may further comprise a double wire track and guiding the ablating portion may further comprise guiding the ablating tip portion between two wire portions of the track. The guiding device may further comprise a wire coupled to the ablation catheter to allow relative movement therebetween and guiding the ablating tip portion may further comprise moving the ablating tip portion generally about a central location of the tissue and thereby applying at least a portion of the ablation pattern, such as in a closed geometric shape around a pulmonary vein opening within the left atrium. The ablation catheter may further comprise a coupling, such as a wire segment, and the method may further comprise actuating the coupling to connect with the template wire. For example, the wire segment may be actuated to coil around the template wire in order to couple the ablating tip portion to the template wire in a manner that allows movement of the ablating tip portion relative to the template wire while guiding the ablating tip portion. The ablation catheter may further include a guide channel and the guiding device may further comprise a template wire extending through the guide channel. In this case, guiding the ablating tip portion then can further comprise moving the ablation catheter along the template wire using the guide channel, thereby applying at least a portion of the lesion/ablation pattern. The template wire may be preformed with a three dimensional shape including a tissue anchoring portion and a template portion along which the ablation catheter is guided. The channel may further comprise a lumen extending lengthwise through the ablation catheter. In this case, the method can then further comprise extending the template wire from the lumen of the ablation catheter to transform the template wire from a straightened condition in the lumen of the ablation catheter to the three dimensional shape including the tissue anchoring portion and the template portion configured to guide the application of at least a portion of the pattern. The method may further comprise guiding the ablating portion using a motorized drive unit to move the ablation catheter along the pattern.

In another aspect, a guidewire is provided for use with an ablation catheter to guide an ablating tip portion of the ablation catheter along a pattern of heart tissue ablation designed to promote normal sinus rhythm of the heart. The guidewire can generally comprise an elongate, flexible wire having a proximal portion extending generally along a lengthwise axis and a distal portion. The distal portion includes a tissue anchoring portion configured to temporarily anchor the wire to the tissue proximate to a location to receive the pattern of ablation and a guide track portion extending laterally from the axis and formed into a shape corresponding generally to at least a portion of the pattern. The guide track portion may include at least one generally circularly shaped wire portion usable as a guide for applying a generally circular, closed pattern of ablation. The guide track portion may also or alternatively include at least one generally curved wire portion and/or straight portion usable as a guide for applying a pattern of ablation. The tissue anchoring portion may further comprise a wire portion that extends laterally relative to the axis such that it is configured to be inserted into a pulmonary vein from the left atrium of the heart and held in place by the walls of the vein.

In another aspect, a guidewire is provided for use with an ablation catheter to guide an ablating tip portion of the ablation catheter along a pattern of heart tissue ablation designed to promote normal sinus rhythm. The guidewire includes an elongate, flexible wire having a proximal portion extending along an axis and a distal portion. The distal portion includes a tissue anchoring portion configured to temporarily anchor the wire to the tissue proximate to a location to receive the pattern of ablation, and a coupling portion. The coupling portion extends laterally from the axis and is configured to allow the wire to be secured to the ablation catheter in a manner allowing movement of the ablating tip portion about the tissue anchoring portion along at least a portion of the pattern. The coupling portion may further comprise a coiled section, channel or ring-like portion of the wire itself or connected to the wire configured to receive the ablation catheter. The tissue anchoring portion may further comprise a wire portion that extends laterally or transversely relative to the axis of the more proximal section of the wire, and is configured to be inserted into a pulmonary vein from the left atrium of the heart and held in place by the walls of the vein.

Various additional features of the invention will become more readily apparent to those of ordinary skill in the art upon review of the following detailed description of the illustrative embodiments, taken in conjunction with the accompanying drawings.

BRIEF DESCRIPTION OF THE DRAWINGS

FIGS. 6A-6C are respective schematic views illustrating a first illustrative anatomy of the left atrium of the heart, and the use of guiding devices to apply patterns of ablation corresponding to the anatomy.

FIGS. 7A-7C illustrate another illustrative anatomy of the left atrium and the use of guiding devices to apply patterns of ablation corresponding to this anatomy.

FIGS. 8A-8C illustrate yet another illustrative form of anatomy sometimes found in the left atrium and the use of guiding devices for applying patterns of ablation corresponding to this anatomy.

FIGS. 9A-9C illustrate yet another illustrative form of anatomy sometimes found in the left atrium and the use of guiding devices for applying patterns of ablation corresponding to this anatomy.

FIGS. 10A-10C illustrate yet another illustrative form of anatomy sometimes found in the left atrium and the use of guiding devices for applying patterns of ablation corresponding to this anatomy.

FIGS. 11A-11C illustrate yet another illustrative form of anatomy sometimes found in the left atrium and the use of guiding devices for applying patterns of ablation corresponding to this anatomy.

FIGS. 13A-13C are schematic perspective views of another embodiment of a system utilizing an ablation catheter and a guiding device including a positioning catheter and a template wire.

FIGS. 16A and 16B are schematic views, partially in cross section, illustrating the distal end portion of an ablation catheter constructed in accordance with an embodiment allowing relative movement between an ablating tip portion and a second portion of the catheter.

FIGS. 17A-17D are respective schematic views, partially in cross section, showing the use of a motorized drive unit in conjunction with a system in accordance with the invention.

FIG. 17 is a cross sectional view of the motorized drive unit taken transverse to the views shown in FIG. 17A-17D and showing additional internal structure for holding the positioning catheter.

FIG. 28 is a schematic, perspective view illustrating the interior of the left atrium and use of a system constructed in accordance with another embodiment.

FIGS. 29A-29D illustrate respective embodiments of a coupling used between the ablation catheter and the template wire.

FIG. 46A is a plan view illustrating a system in accordance with a first embodiment of the invention, and illustrating an ablation catheter being guided by a guiding device temporarily anchored within a pulmonary vein.

FIG. 46B is a view similar to FIG. 46A, but illustrating a subsequent portion of the method in which the ablation catheter is being used to ablate tissue surrounding the pulmonary vein within the left atrium of the heart.

FIG. 48A is a plan view illustrating a system in accordance with another embodiment of the invention and showing another type of connection between the ablation catheter and the guiding device.

FIG. 48B is a view similar to FIG. 48A, but illustrating a subsequent portion of the method.

DETAILED DESCRIPTION

Figure 1A:
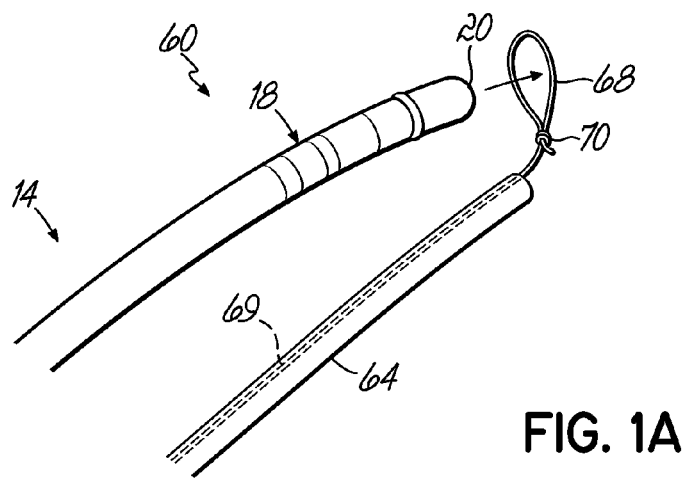
FIGS. 1A-1F are schematic views illustrating a system in accordance with another embodiment of the invention, including an ablation catheter, and a guiding device comprising a positioning catheter and a template wire.
Figure 1B:
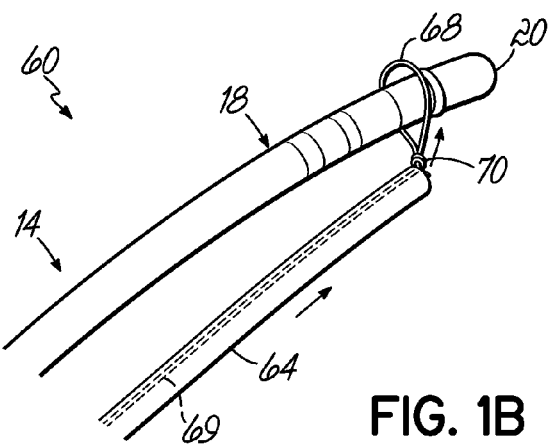

In the various embodiments, like reference numerals are used to refer to like elements of structure and function and therefore no further description herein is necessary, while reference numerals with one or more prime (') marks refer to similar structure and function as elements having the reference numerals without the one or more prime (') marks, the minor differences either described herein or apparent from review of the drawings.

Figure 1C:
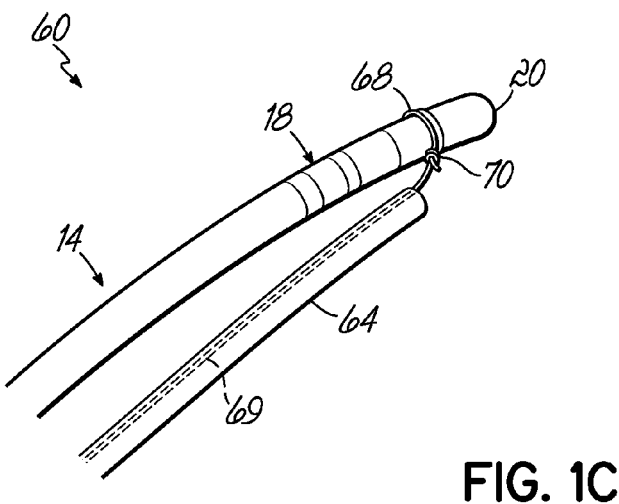
Figure 1D:
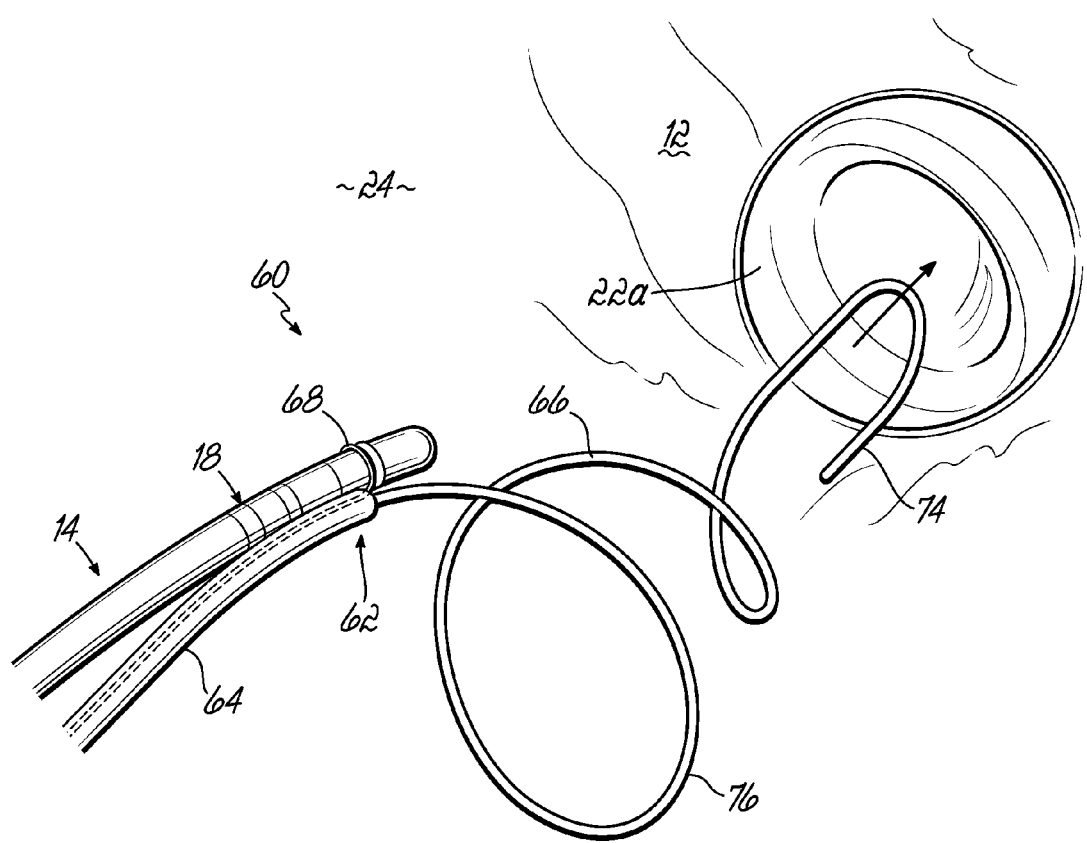

FIGS. 1A-1D illustrate a system 60 constructed in accordance with another embodiment. This system 60 includes an ablation catheter 14, as previously described. The system 60 further includes a guiding device 62 (FIG. 1D) which, in this embodiment, includes a positioning catheter 64 operatively coupled with the ablation catheter 14 and, as illustrated in FIG. 1D, also coupled with a template wire 66. The positioning catheter 64 in this particular embodiment is coupled with the ablation catheter 14 through the use of a snare 68 formed, for example, from suture 69 and tightened against the distal tip 18 of the ablation catheter 14 with a slip knot 70 as shown in FIG. 1C. Thus, the positioning catheter 64 provides one manner of indirectly connecting the template wire 66 and the ablation catheter 14. As will be understood from a review of FIG. 1D, the combination of the ablation catheter 14 and the positioning catheter 64 are inserted into the vascular system of a patient percutaneously in any known manner, either together or separately using suitable delivery techniques, until the distal tip portions thereof are within the left atrium of the heart. The template wire 66 of the guiding device 62 is then extended from the positioning catheter 64 and takes on a preformed shape as generally illustrated in FIG. 1D such that portions thereof, including a temporary tissue anchoring portion 74 and a template portion 76 extend laterally relative to the main long axis of the more proximal portions of the template wire 68. The positioning catheter 64 may be used with any of the template wires contemplated herein. The tissue anchoring portion 74 may comprise, as illustrated, a J-shaped or U-shaped hook which is sufficiently flexible so as to prevent injury, or otherwise constructed so as to prevent injury, but sufficiently strong to temporarily anchor the template wire 68 when inserted into a pulmonary vein opening 22a as illustrated in FIG. 1D. Use of the system 60 shown in FIG. 1D will become more apparent with reference to FIGS. 1E and 1F which show that the template portion 76 of the template wire 66 is used to guide the ablating tip portion 20 of the ablation catheter 14 in conjunction with the positioning catheter 64 as the position catheter 64 is moved along the template portion 76 and the ablation catheter 14 is used to apply spot ablations as the positioning catheter 64 is moved or indexed along the template portion 76, thereby creating the lesions 40 contacting each other to form a continuous pattern 50.

Figure 1E:
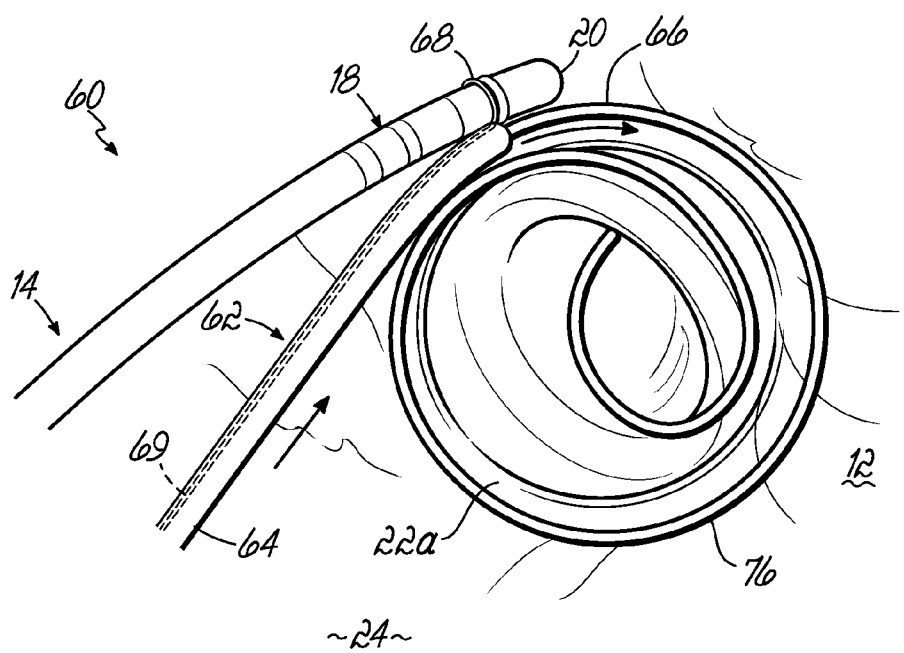
Figure 1F:
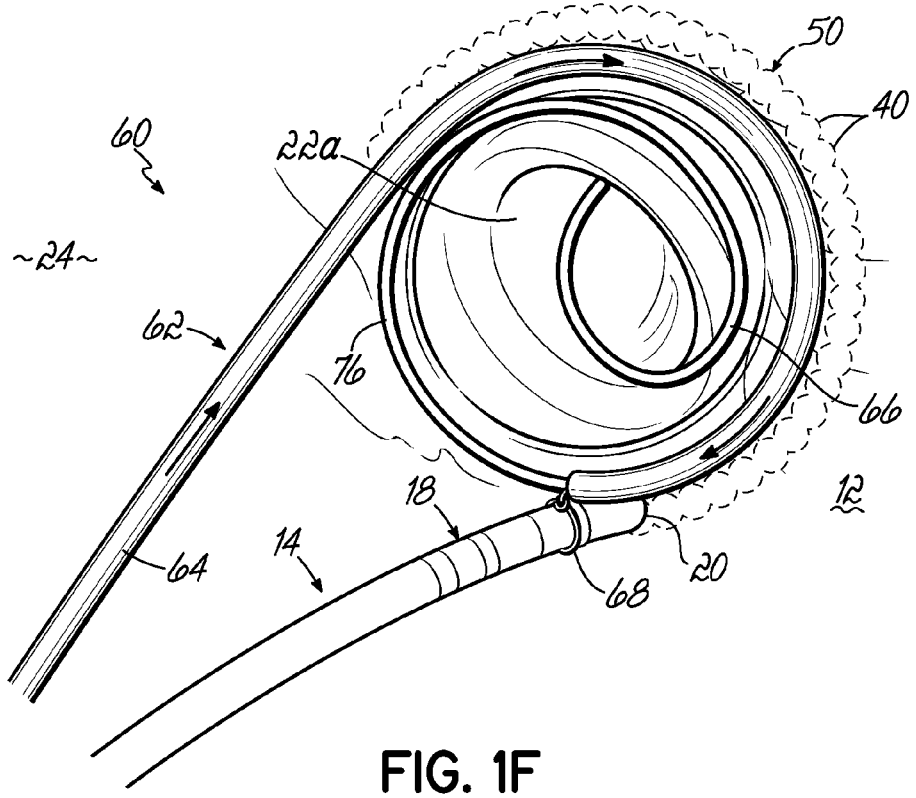

As illustrated in FIGS. 1E and 1F, subsequent steps in the method involve pushing the positioning catheter 64 along the template portion 76 of the template wire 66 to accurately position the ablating tip portion 20 of the ablation catheter 20 along the template wire 66. The spot ablations may be applied as the positioning catheter 64 is moved or indexed in the direction shown in FIG. 1E, i.e., a forward or distal direction, to form the pattern of lesions 40 as schematically illustrated in FIG. 1F. Alternatively, the positioning catheter 64 and the connected ablation catheter 14 may be moved along the template portion 76 of the wire 66 to a starting point and then the positioning catheter 64 may be withdrawn along the template portion 76 of the wire 66 carrying the ablating tip portion 20 with it by way of the snare connection 68. As the positioning catheter 64 is withdrawn in a proximal direction (opposite to that shown in FIG. 1F), the ablating tip portion 20 may be selectively activated in a known manner to create the spot lesions 40 or other forms of lesion in the reverse direction to that shown. In either case, a pattern of ablation may be created that is designed to promote normal sinus rhythm and, more specifically, for example, designed to treat AF.

Figure 2:
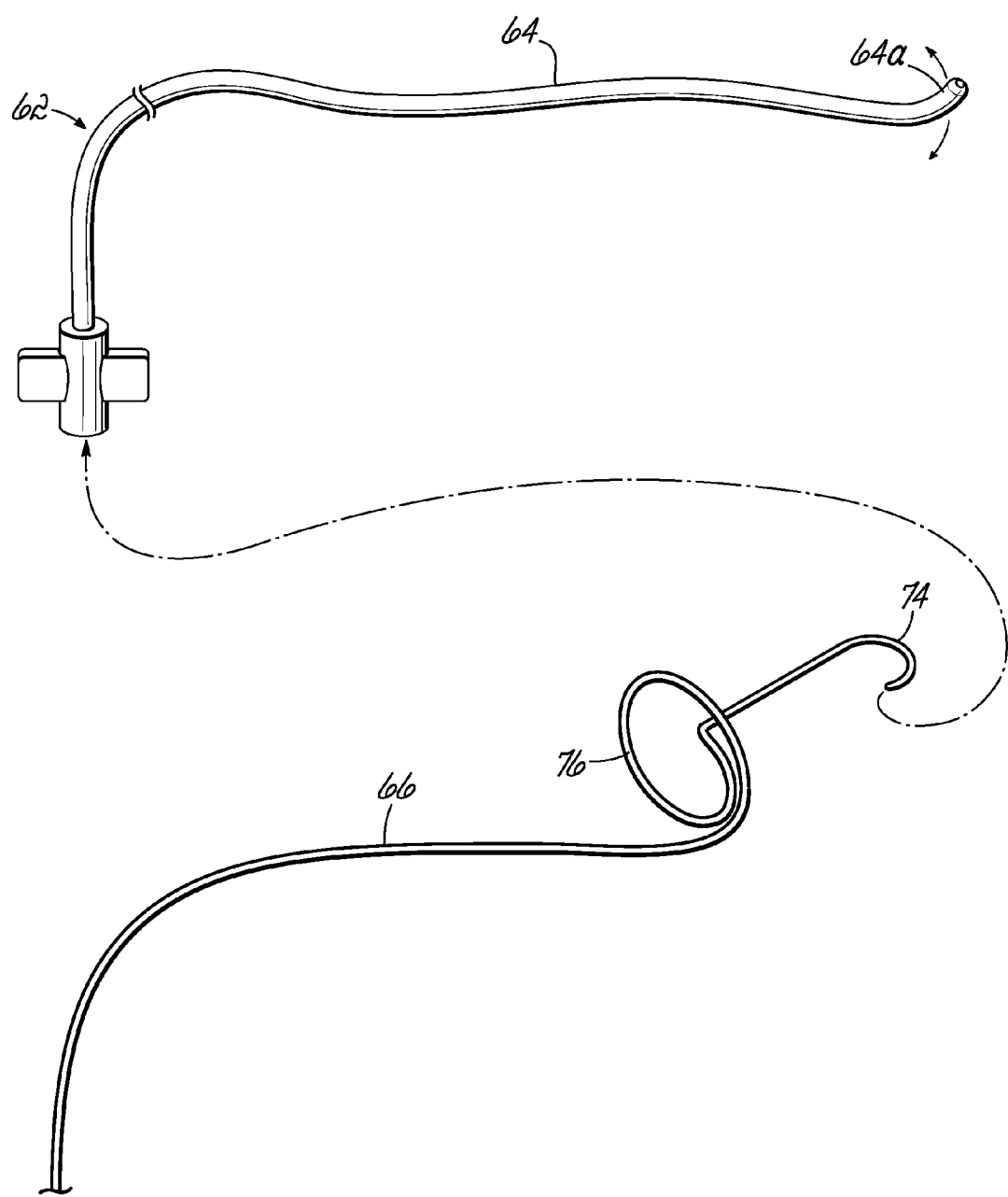
FIGS. 2-4 are respective schematic, perspective views illustrating a system constructed in accordance with another embodiment, and use thereof in ablating tissue within the left atrium.
Figure 3:
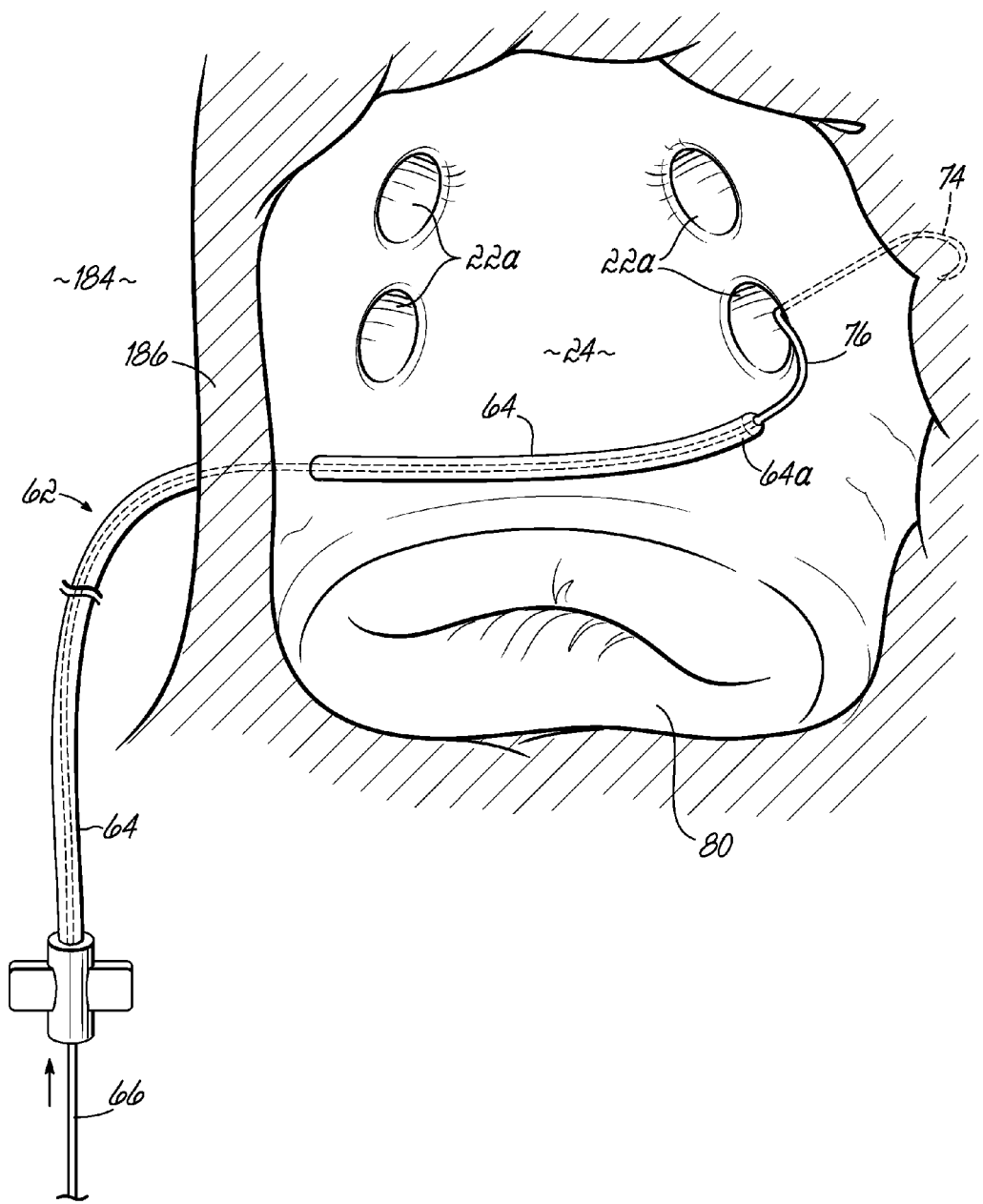
Figure 4:
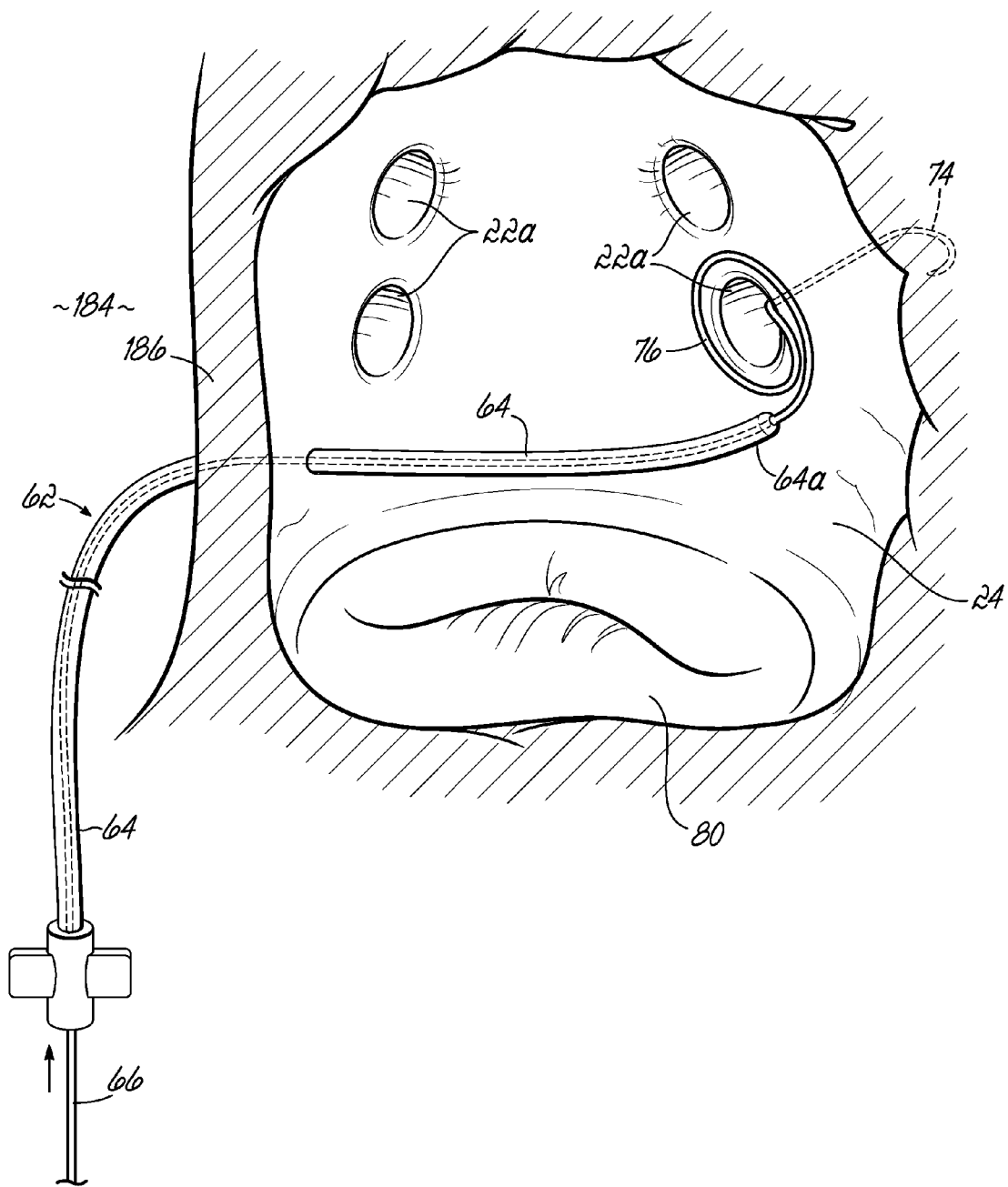

FIGS. 2-4 illustrate more particularly an illustrative method of introducing the template wire 66 into the left atrial chamber 24. In this regard, the template wire 66 is preformed into the required shape, such as that shown in FIG. 1, having a temporary anchoring portion 74 and a template portion 76 and is introduced into a positioning catheter 64, which may have a steerable distal end. This straightens the template wire 66 for introduction into the patient (FIG. 3). Once the distal tip 64a of the catheter 64 is introduced into the left atrial chamber 24, the template wire 66 may be extended from the distal tip 64a. The wire 66 will transform either automatically due to its physical characteristics or it will be transformed into its preformed shape (FIG. 4). The template wire 66 will then be used in one of the manners generally described herein, with a tissue anchoring portion 74 thereof anchored to tissue, such as by being inserted into a pulmonary vein opening 22a, and a template portion 76, for example, being used as a guide for creating a pattern of lesions, such as in one of the manners described herein.

Figure 5A:
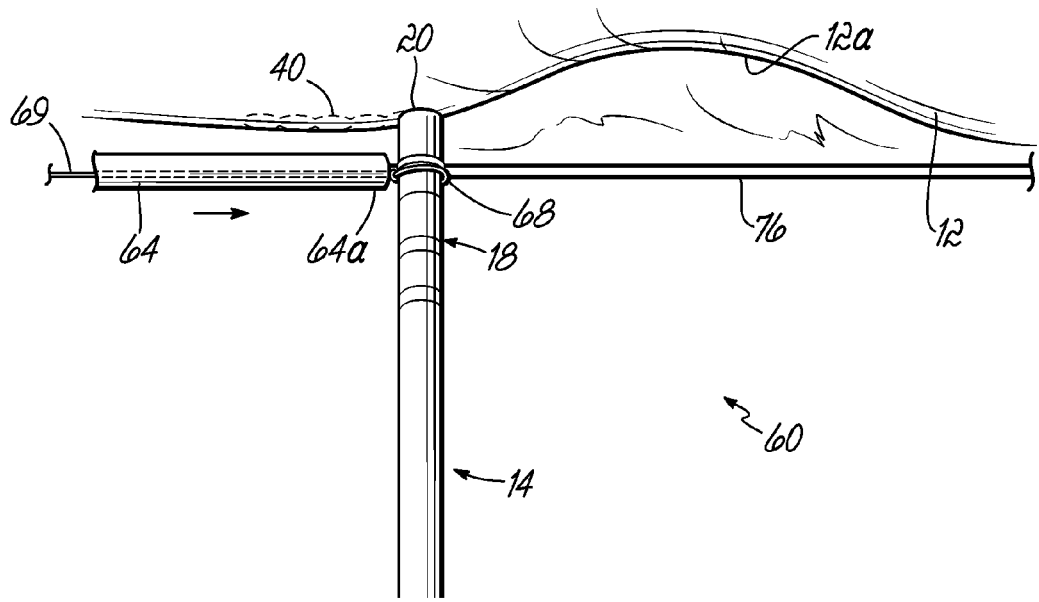
FIGS. 5A and 5B are schematic views respectively illustrating use of a coupling feature between the ablation catheter and the guiding device allowing limited movement of the ablation catheter to accommodate three dimensional variations in the surface of the tissue to be ablated.
Figure 5B:
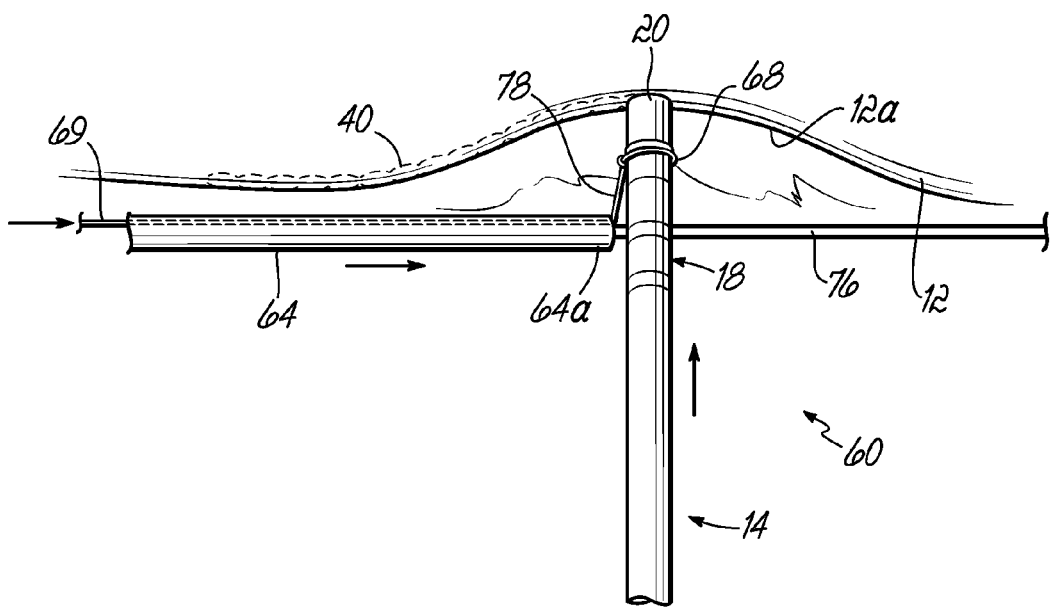

FIGS. 5A and 5B schematically illustrate the ability of the coupling between the positioning catheter 64 and the ablation catheter 14 to allow limited movement of the ablating tip portion 20 toward and away from the template portion 76. In this regard, the template portion 76 will lay generally flat against the tissue 12 to be ablated, while the tissue 12 may have various three dimensional contours, angulations and recesses 12a to which the wire portion 76 will not conform as schematically shown in FIGS. 5A and 5B. These contours or angulations 12a in the surface of the atrial wall will be accommodated by the coupling, which in this case, includes at least a short length of suture 78 that allows the ablating tip portion 20 to be moved in a direction shown relative to the template portion 76 and the distal tip 64a of the positioning catheter 64 to engage against the tissue surface 12a with the proper amount of force to create sufficient lesions in the tissue 12.

FIG. 6A illustrates, in schematic fashion, the left atrium 24 of the heart anatomy, including four pulmonary veins 22 and the mitral valve 80 which provides communication with the left ventricle (not shown). This represents typical anatomy of a human heart. FIGS. 6B and 6C respectively illustrate template wires 66 constructed in accordance with one embodiment of the invention and which may be used in accordance with methods as described herein to create respective closed geometric patterns 50 of lesions 40 in surrounding fashion to respective pairs of the pulmonary vein openings 22a in the interior walls of the atrium 24 as shown in FIG. 6C.

FIGS. 7A-7C are similar views to those shown in FIGS. 6A-6C, except that an alternative anatomy is illustrated and the use of only three template wires 66 instead of four to apply closed patterns 50 of ablation about the openings 22a to the pulmonary veins 22. The left hand side of FIG. 7B further illustrates that two of the template wires 66 may overlap to assist with application of the closed pattern 50 of ablation schematically illustrated in FIG. 7C.

FIGS. 8A-8C are similar figures to FIGS. 7A-7C except that the anatomy of the heart and, specifically, the connections of the pulmonary veins 22 to the left atrium 24 are slightly different.

FIGS. 9A-9C are similar views to FIGS. 6A-6C, but again showing a slight variation to the anatomy of the left atrium 24 and the connections of the pulmonary veins 22 thereto, and illustrating the use of two sets of overlapping template wires 66 to apply the closed patterns 50 of ablation illustrated in FIG. 9C.

FIGS. 10A-10C and 11A-11C are similar to FIGS. 9A-9C, but again illustrating slight variations to the anatomy of the left atrium 24 and the connections of the pulmonary veins 22 thereto. These embodiments again illustrate the use of overlapping template wires 66 and closed patterns 50 of ablation by following or indexing the ablating tip portion 20 of an ablation catheter (not shown) along the curvatures 76 of the wires 66.

Figure 12A:
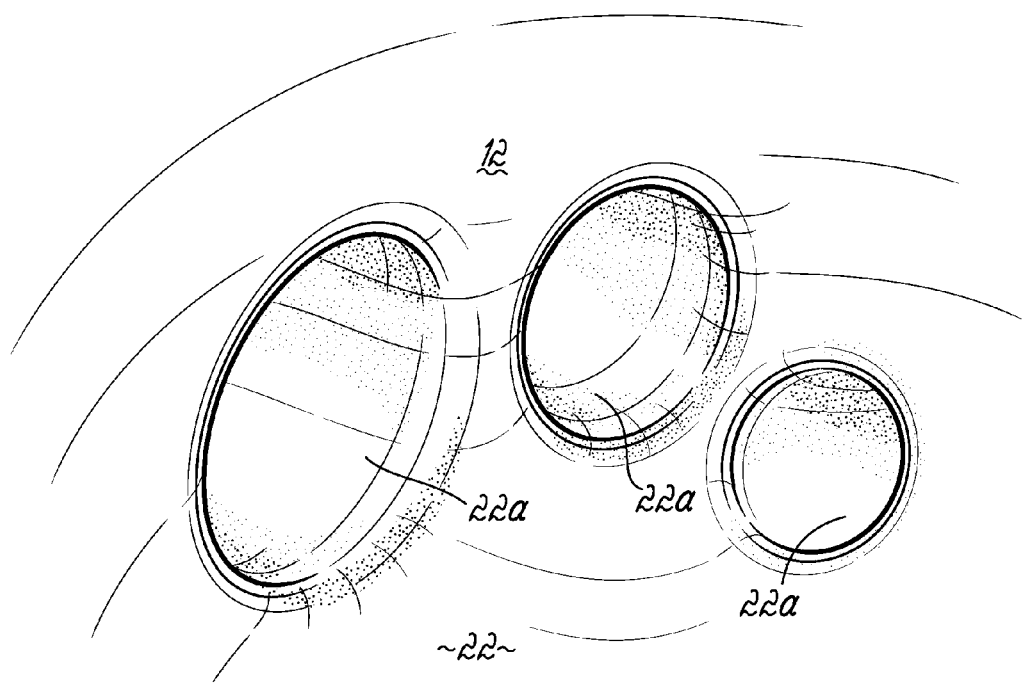
FIGS. 12A-12D present three dimensional or perspective, schematic illustrations of the interior of a left atrium and the use of two guiding devices to apply a pattern of ablation surrounding three openings associated with the pulmonary veins.
Figure 12B:
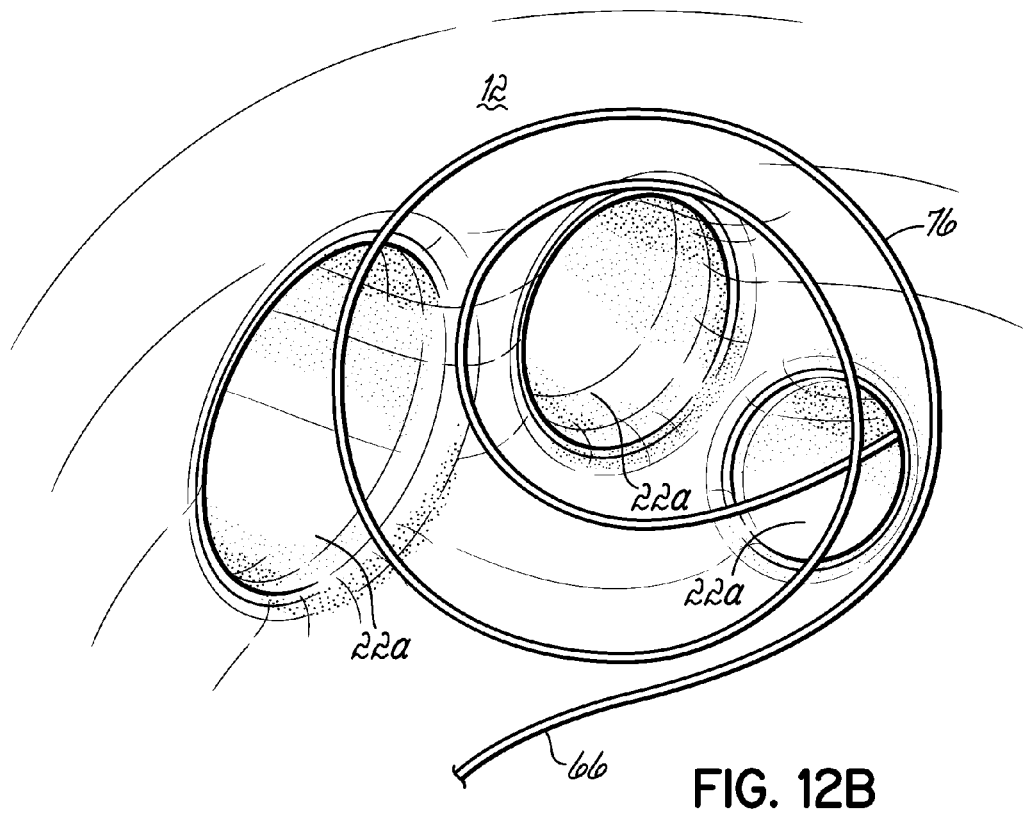
Figure 12C:
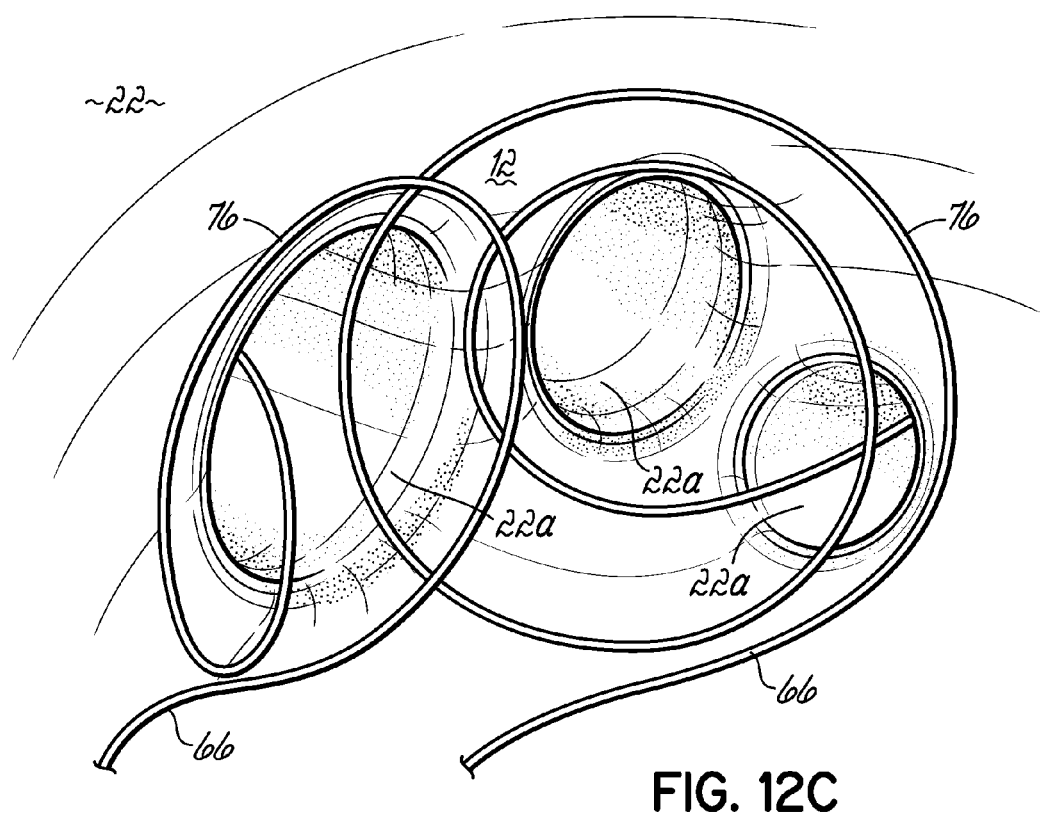
Figure 12D:
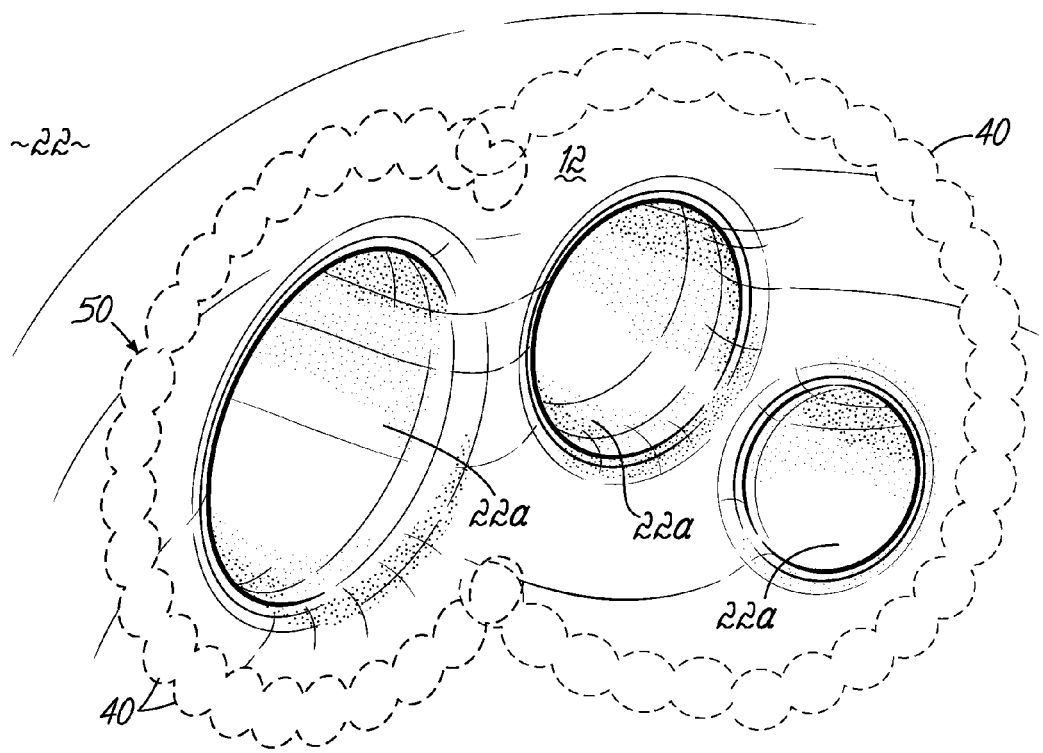

FIGS. 12A-12D present a schematic, perspective view of the anatomy, for example, similar to that shown in FIG. 8A and illustrating in stepwise format the introduction of a first template wire 66 into the left atrium 24 in FIG. 12D. A temporary tissue anchoring portion 74 (see FIG. 1D) thereof is inserted into a first opening 22a of a pulmonary vein 22 as previously discussed while a second portion or template portion 76 engages against the interior tissue 12 of the left atrium 24 generally as shown to surround at least two of the openings 22a to the pulmonary veins 22. The template portion 76 is flexible enough to conform generally in three dimensions to the interior tissue surface of the atrium 24. A second template wire 66 is percutaneously introduced in a similar fashion as shown in FIG. 12C such that a temporary anchoring portion 74 (see FIG. 1D) is inserted into the third pulmonary vein opening 22a and a template portion 76 surrounds the third pulmonary vein opening 22a. At this point, as shown in FIG. 12D, an ablation catheter 14 (not shown in this figure) may be directed within the atrium 24 and controlled/steered such that the ablating tip portion 20 follows along the respective template portions 76 to form the closed pattern 50 of lesions 40 as generally and schematically illustrated in FIG. 12D. Because of the coiled nature of the template wire 66 and template portion 76, the tip 20 may be selectively directed and engaged against different portions of the coil (inner and/or outer) to vary the diameter of the ablation pattern 50.

FIGS. 13A-13C illustrate the system 60 including the ablation catheter 14, positioning catheter 64 and template wire 66. FIGS. 13B and 13C illustrate one method of using the system 60 and guiding the ablating tip portion 20 of the ablation catheter 14 along the template wire 66. Although not illustrated, it will be understood that the temporary anchoring portion 74 is anchored within a pulmonary vein opening as previously discussed during the operation of the system. As the positioning catheter 64 is moved along the template portion 76 of the wire 66, the ablation catheter 14 is likewise moved and guided along the template portion 76 due to the connection formed by the suture snare 68 between the positioning catheter tip 64a and the ablation catheter 14. As the positioning catheter 64 and ablation catheter 14 are moved by the electrophysiologist in the manner illustrated, the ablating tip portion 20 may be activated to form the spot lesions 40 as shown in FIG. 13C into a closed pattern 50 of lesions 40 or any other desirable pattern of lesions, depending on the configuration of the template portion 76. FIG. 13B illustrates a design in which the winding of the coiled or helical template portion 76 is spaced apart at a distance that may be too large to ensure a closed pattern 50. FIG. 13C illustrates a closer spacing that will result in a side-to-side contact of lesions 40 to ensure a closed geometric pattern 50.

Figure 14:
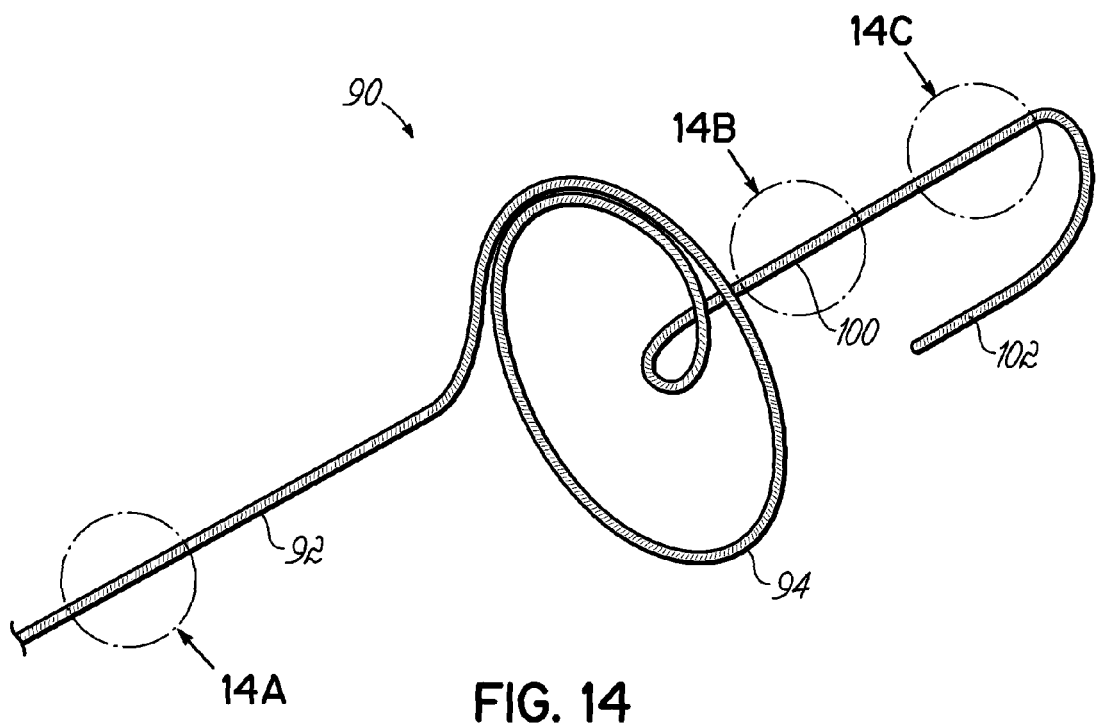
FIG. 14 is a perspective view illustrating another embodiment of a template wire including sections along its distal end portion that are formed with different stiffnesses.
Figure 14A:
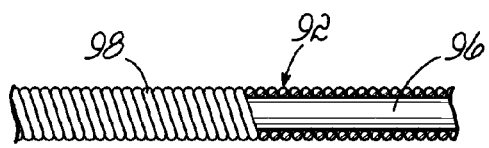
FIGS. 14A, 14B and 14C are respective enlarged views of the encircled areas 14A, 14B and 14C shown in FIG. 14.
Figure 14B:
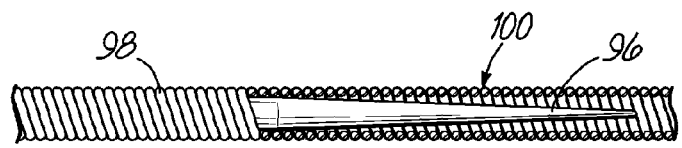
Figure 14C:
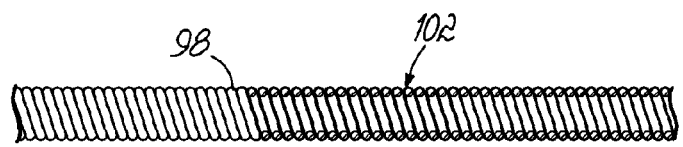

FIGS. 14, and 14A-14C illustrate another template wire 90 constructed to have varying stiffness along the length thereof at the distal portion shown. In these and the other figures herein, it will be understood that the template wire 90 will be formed long enough to be inserted percutaneously into a patient, for example, from a femoral vein insertion point. It may be desirable to maintain a relatively stiff area of the wire 90 that includes the section 92 proximal to a template portion 94, as well as the template portion 94, by having a composite construction including a wire core 96 and an outer coil portion 98. These sections 92, 94 are still flexible enough to be delivered percutaneously, but stiff enough to provide the requisite support at the template portion 94. It may then be desirable to have a portion 100 of the wire 90 between a tissue anchoring portion 102 and the template portion 94 that gradually reduces in flexibility such as by tapering the wire core 96 as shown in FIG. 14B. At the most distal end or temporary anchoring portion 102, the wire core 96 may be eliminated to make this section highly flexible for insertion into the opening of a pulmonary vein as previously discussed while preventing damage to tissue either in the pulmonary vein or in the left atrial chamber of the heart while manipulating the template wire 90 into position in a percutaneous catheter based procedure. In this embodiment, as well as other embodiments, the template wire 90 may have an outer coating which is non-slip, such as a PTFE coating.

Figure 15A:
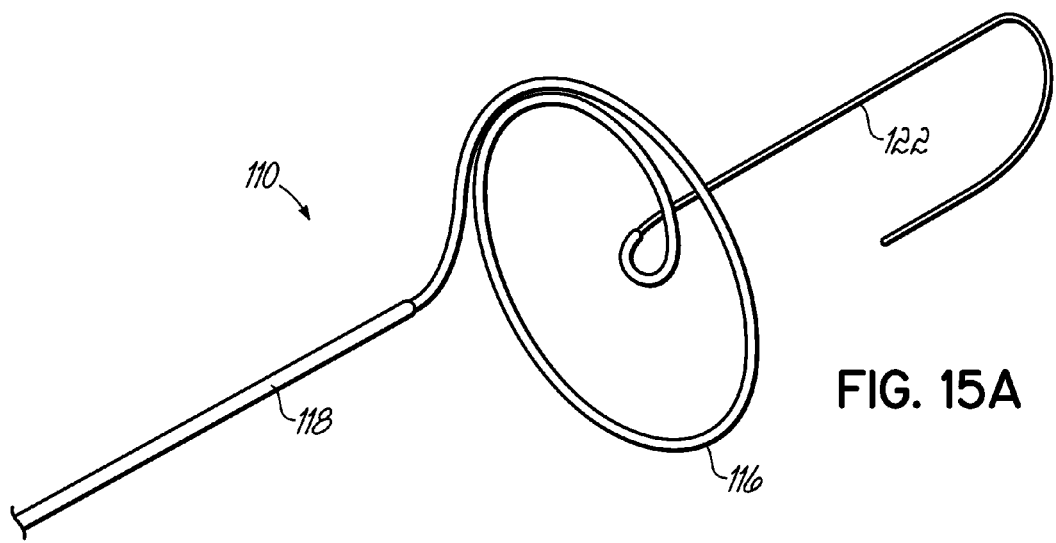
FIGS. 15A, 15B and 15C are respective perspective views of the distal end portions of three further embodiments of a template wire having varying stiffness along their lengths at the distal end portions.
Figure 15B:
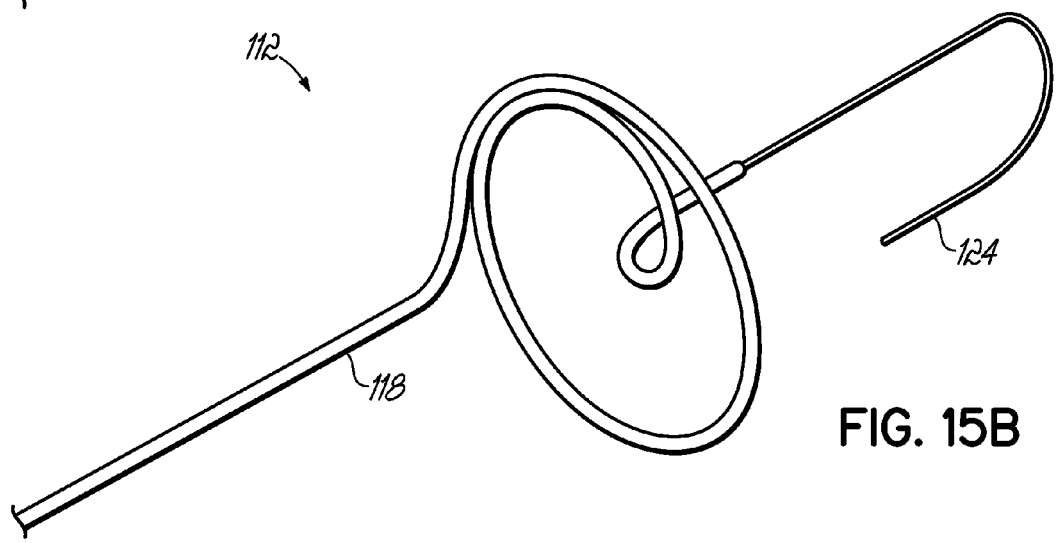
Figure 15C:
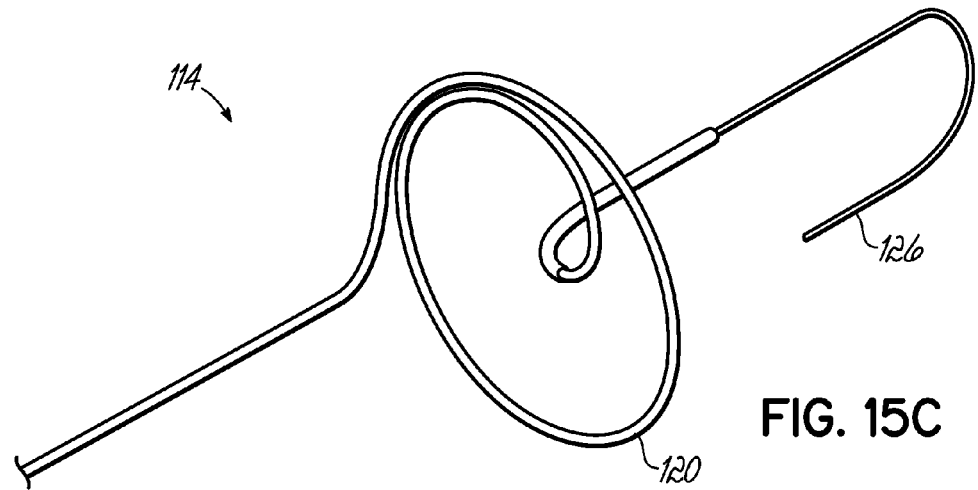

FIGS. 15A, 15B and 15C respectively illustrate alternative embodiments of the template wires 110, 112, 114 to that shown in FIG. 14, and respectively illustrating different manners of providing varying stiffness along the length of the wires 110, 112, 114. In these embodiments, the wires are formed with varying thicknesses that the thicker portions of the wires exhibit more stiffness than thinner portions of the wire, for reasons discussed in connection with FIG. 14. The thicker portions of the wires 110, 112, 114 may be formed, for example, through the use of coatings or layers of construction, or simply different thicknesses of a single material construction. As with the other embodiments, these wires include template portions 116, 118, 120 and tissue anchoring portions 122, 124, 126 as previously discussed.

FIGS. 16A and 16B illustrate an ablation catheter 130 with a distal end portion 132 constructed according to an alternative embodiment. The positioning catheter 64 and template wire 66 are shown in dash-dot lines for environmental purposes. It will be understood that this ablation catheter 130 is usable in many applications, not limited to those discussed herein. In this embodiment, the distal end portion 132 of the ablation catheter 130 has an ablating tip portion 134, as well as a second, more proximal portion 136. The ablating tip portion 134 is coupled to the second portion 136 in a manner allowing relative movement of the second portion 136 toward and away from the ablating tip portion 134 in directions parallel to the main long axis of the catheter 130. The user can thereby apply axial force to the ablating tip portion 134 during an ablation procedure while engaging the tissue 12 to be ablated and the second portion 136 will move axially relative to the ablating tip portion 134 to indicate an amount of axial force applied by the user. This may provide a tactile response indicated to the user in any suitable manner to communicate that the requisite axial force has been applied to the tissue 12 to apply proper ablation. It will be understood that the second portion 136 may be an integral or unitary construction with the ablating tip portion 134, or may be structure that is not disposed coaxially with the ablating tip portion 134 as illustrated. In this embodiment, when the second portion 136 is moved or pushed axially to a stopped position as shown in FIG. 16B, the requisite axial force has been applied. As opposed to a physical stop, one or more electronic sensors may be used to detect the physical movement of the second portion 136 relative to the ablating tip portion 134. This may be communicated electronically to the user. In the embodiment illustrated, the axial movement is a biased movement provided by a compressible spring 138 contained in a sleeve 140.

FIGS. 17A-17D illustrate the use of a motorized drive unit 150 in conjunction with a system 60 as previously described. In this embodiment, the motorized drive unit 150 is schematically illustrated as including a handle portion 152 with an actuating switch 154 and a passage 156 for containing the ablation catheter 14 and the positioning catheter 64 as previously discussed. The positioning catheter 64 is secured to the ablation catheter 14 with a suture 69 and snare 68, also as generally discussed above. As shown in FIGS. 17A and 17B the positioning catheter 64 is driven or moved through the handle 152 by a drive mechanism including rollers 158, for example, mounted in a suitable support 159 for rotation, and driven by a motor 160. The motor 160 may be powered by a battery 162, schematically illustrated, or by another power source. The drive mechanism, such as the series of motorized rollers 158, moves the positioning catheter 64 along the template wire 66. As shown in FIG. 17, the positioning catheter is held in place for sliding movement in a lower channel 164 and by a pair of upper retaining elements 166a, 166b. The template wire 66 has been previously inserted into the left atrium 24 in a percutaneous manner using appropriate catheter delivery techniques as known, with the temporary anchoring portion 74 (see FIG. 1D) of the template wire 66 inserted into the opening 22a of a pulmonary vein 22 as previously discussed. The positioning catheter 64 is then driven along the template wire 66 by the motorized drive unit 150, for example, by actuating the switch 154 in a forward direction. A suitable sensor 168 may be used to detect a marker 170 on the positioning catheter 64 to indicate when the distal tip 64a of the positioning catheter 64 is at the proper location along the template wire 66. The ablation catheter 14 is moved into position by moving the ablation catheter 14 forward while pulling the suture 69 into the distal end 64a of the positioning catheter 64. This will position the ablating tip portion 20 of the ablation catheter 14 at the distal end 64a of the positioning catheter 64 as shown in FIG. 17C. At this point in time, the positioning catheter 64 is withdrawn in a proximal direction by reversing the motorized drive unit 150, such as by actuating the switch 154 in the reverse direction and reversing the rotation of the series of drive rollers 158. As the positioning catheter 64 is withdrawn along the template portion 76, the ablating tip portion 20 of the ablation catheter 14 is used to create a pattern 50 of ablation along the template portion 76. This ablation may be spot or focal ablation, as previously discussed, and may form all or part of a closed pattern 50 of lesions 40 designed to treat AF, as schematically illustrated in FIG. 17D. In this embodiment, the ablation catheter 14 could alternatively or also be driven by a suitable drive mechanism. Using an ablation level sensing system such as discussed herein, the level or amount of ablation may be detected by sensing impedance level, temperature, time of ablation, or other characteristics. A control may automatically activate the tip portion 20, detect the appropriate level of ablation, then deactivate the tip portion 20 and automatically index the tip portion 20 to the next location in the pattern 50 where the process is repeated until the full pattern 50 is formed. In this illustrative example, the ablation catheter 14 is indirectly coupled to the drive rollers 158 by way of being directly connected, via suture 69, to the positioning catheter 64. It will be appreciated that a direct connection may be used instead to move or index the catheter tip 20 along the pattern.

Figure 18A:
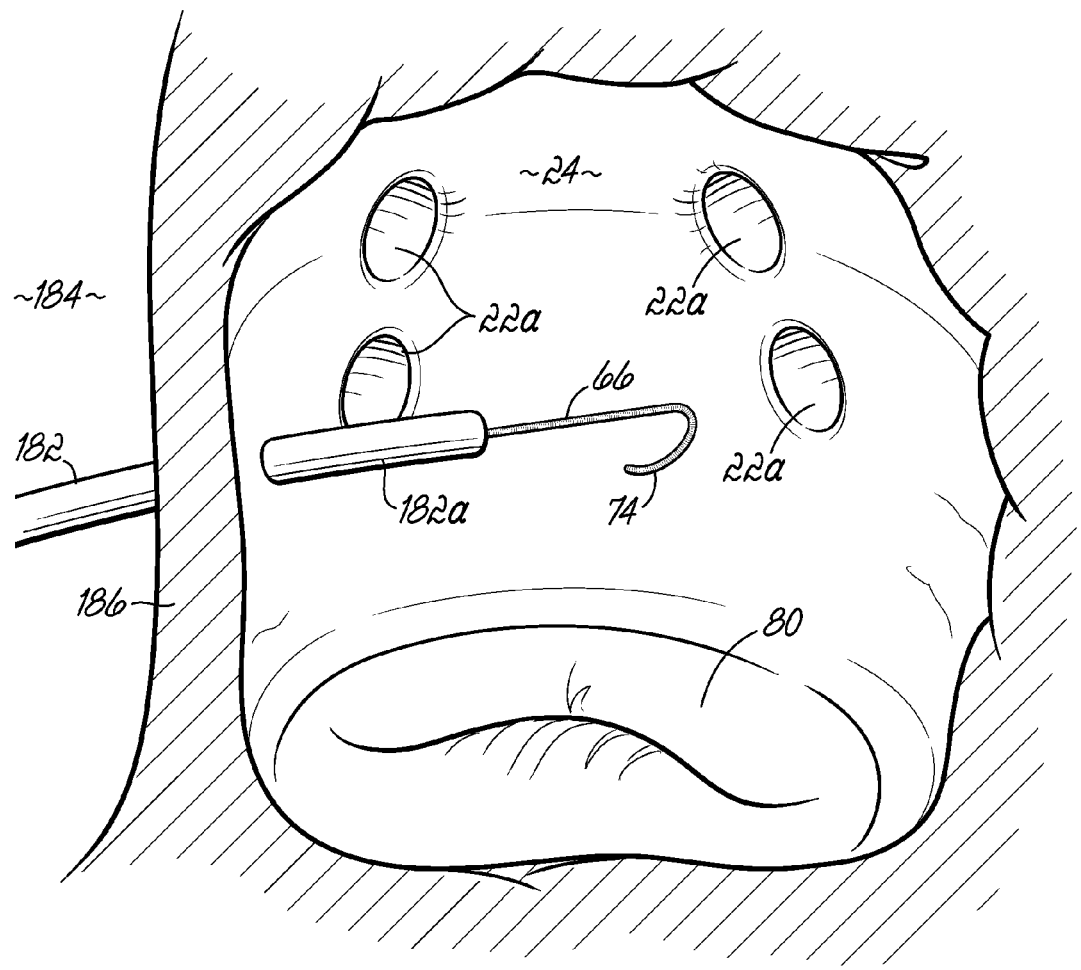
FIGS. 18A-18L are respective schematic, perspective views illustrating use of a system in the left atrium, and constructed in accordance with another embodiment of the invention.
Figure 18B:
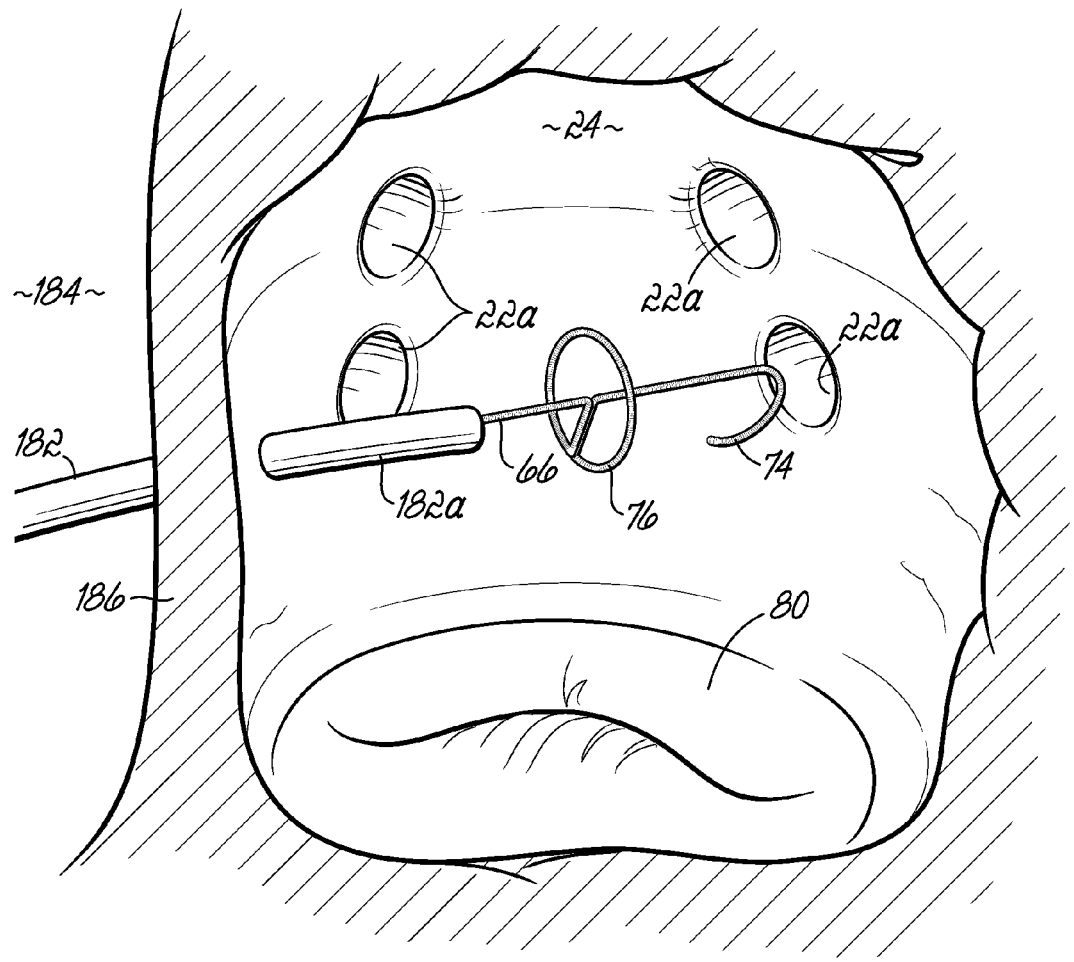

FIGS. 18A-18L illustrate a system 180 in accordance with another embodiment and a method of using the system percutaneously to apply a pattern 50 of lesions 40 in the interior wall of the left atrium 24 for treatment of AF. In accordance with known catheter based techniques, a delivery catheter 182 is directed into the vascular system of a patient. The distal tip portion 182a of the delivery catheter 182 is, for example, introduced transeptally into the left atrium 24 via the right atrium 184 and through the septal wall 186. This may be accomplished in a known manner from a femoral vein insertion point. In this and the other embodiments, it will be understood that one or more other catheter devices may be introduced through the same insertion point, or using the other femoral vein of the patient, for example, to facilitate the use of testing or visualization aids (not shown). Once positioned in the left atrium 24, a template wire 66 is extended from the delivery catheter 182 and takes on a preformed shape including a temporary tissue anchoring portion 74 and a template portion 76 as illustrated in FIG. 18B. In this and in other embodiments, the preformed shape may be facilitated through the use of highly flexible materials, such as superelastic materials that will allow the wire to be straightened when placed directly or indirectly by use of another catheter (not shown) into the lumen of the delivery catheter 182 but then assume its preformed shape when unrestrained, such as when extended from the distal end of the delivery catheter 182 as shown in FIG. 18B. Other manners of transforming the distal end of the template wire 66 into the requisite shapes may be used instead, such as via mechanical structure or the use of shape memory materials that are reshaped through the application of energy.

Figure 18C:
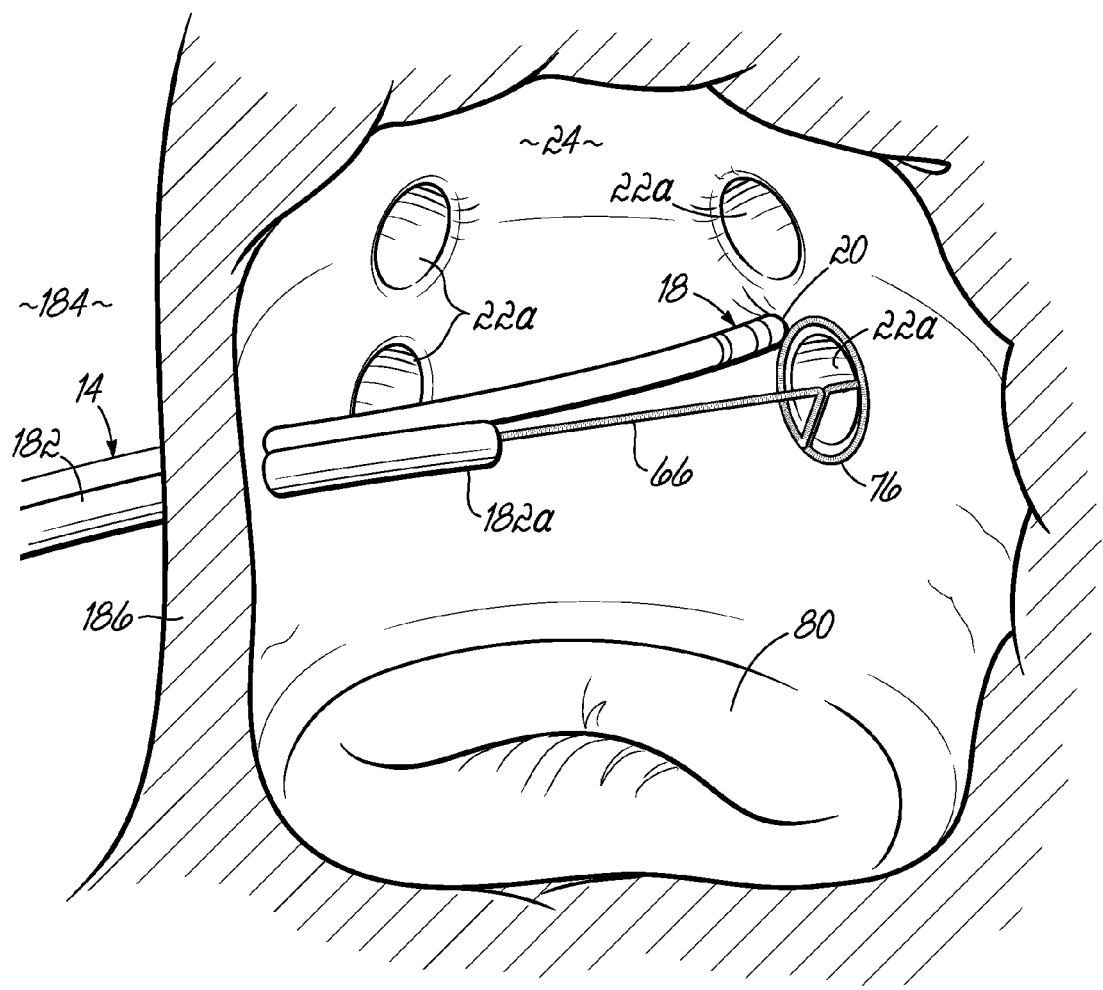
Figure 18D:
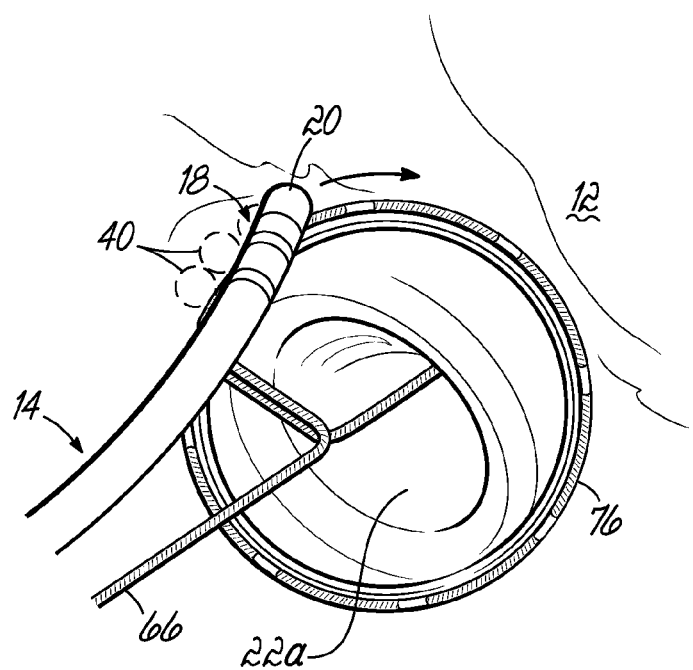
Figure 18E:
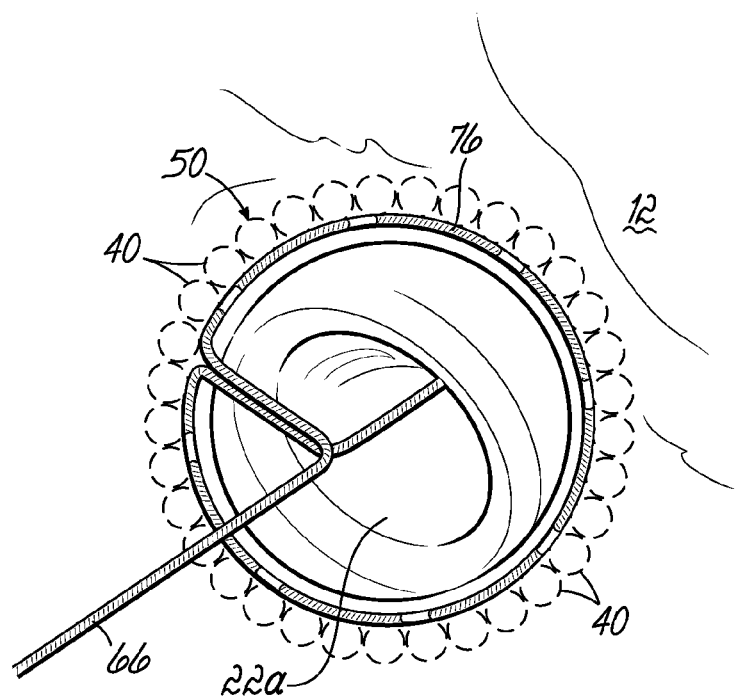
Figure 18F:
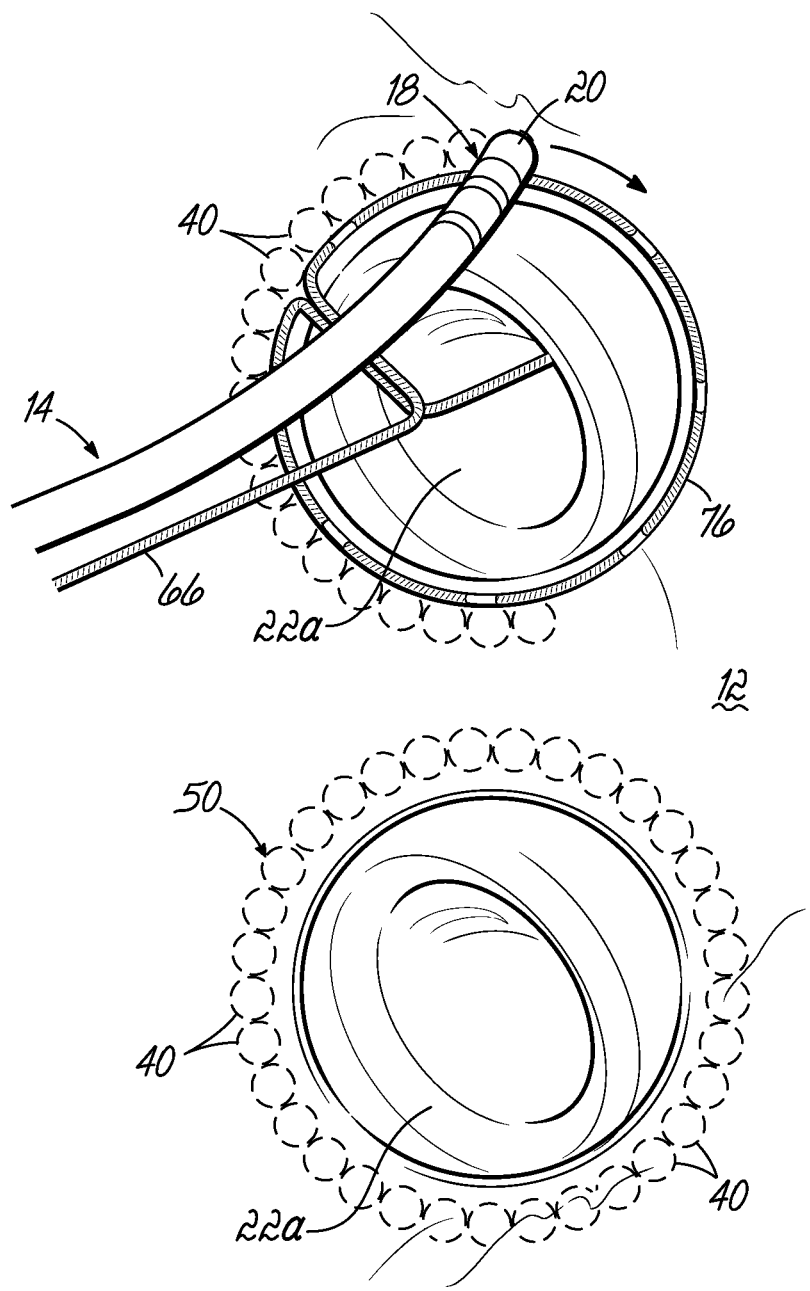
Figure 18G:
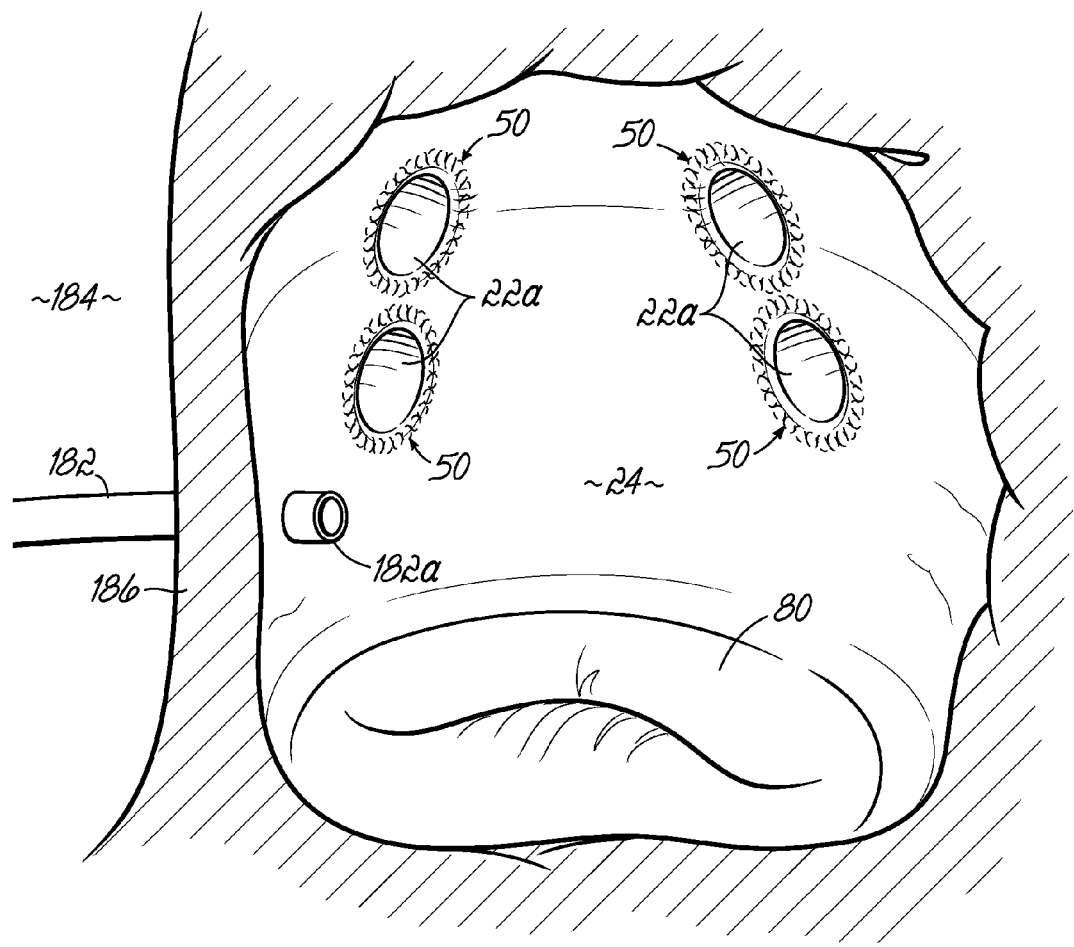

As shown in FIG. 18C, after the guiding device, which in this case comprises template wire 66 including the temporary tissue anchoring portion 74 (FIG. 18B) and the template portion 76, is inserted and anchored into one of the pulmonary vein openings 22a, an ablation catheter 14 may be used by an electrophysiologist to create a series of lesions 14. In this regard, the ablation catheter 14 may be introduced into the vascular system of the patient percutaneously in known manners and then the ablating tip portion 20 may be engaged with the template portion 76 of the wire as shown in FIGS. 18C and 18D to create a pattern 50 of ablation/lesions as for example shown in FIG. 18E. The template wire 66 is removed after the pattern of ablation is applied and may then be used in similar manners to apply a pattern of lesions 40 in surrounding relation to another pulmonary vein opening 22a as shown in FIG. 18F. As shown in FIG. 18G, all pulmonary vein openings may be isolated in this manner by serially introducing the template wire 66 in each and forming the patterns 50 of lesions.

Figure 18H:
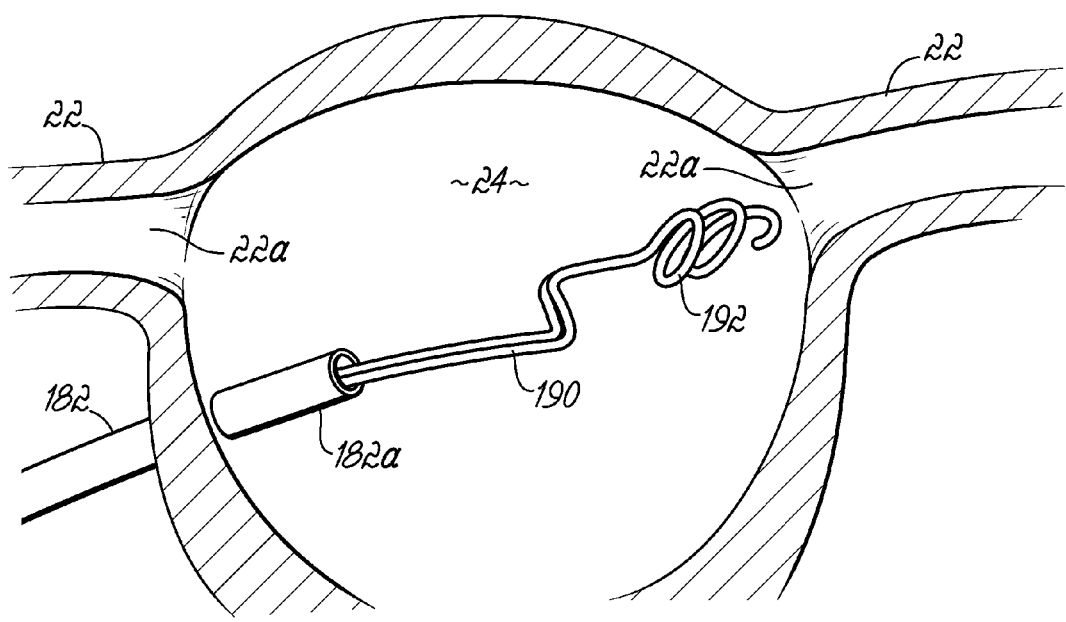
Figure 18I:
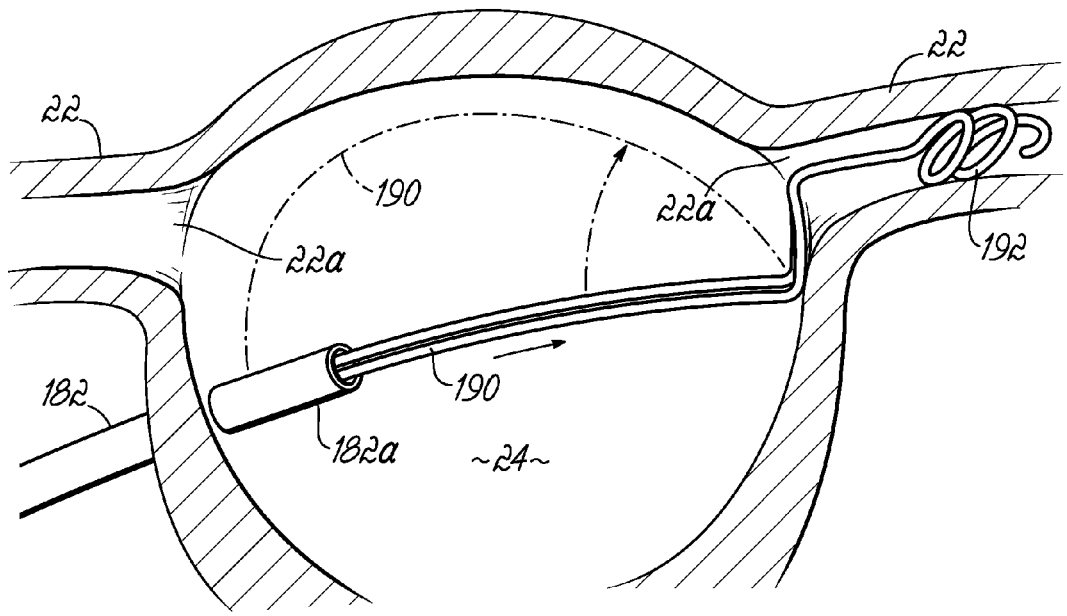
Figure 18J:
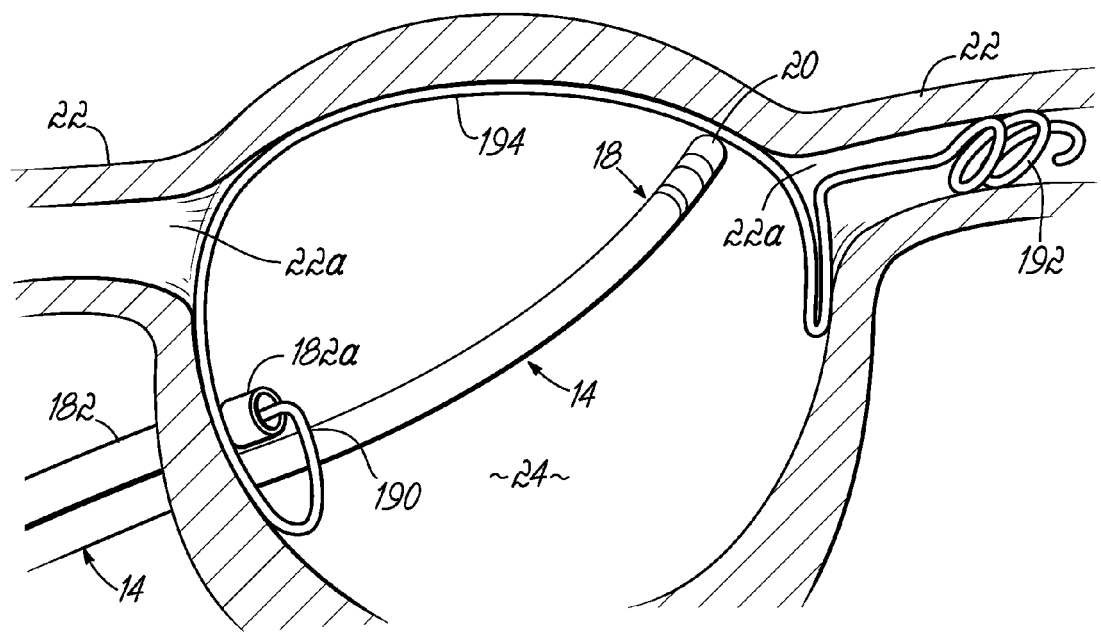
Figure 18K:
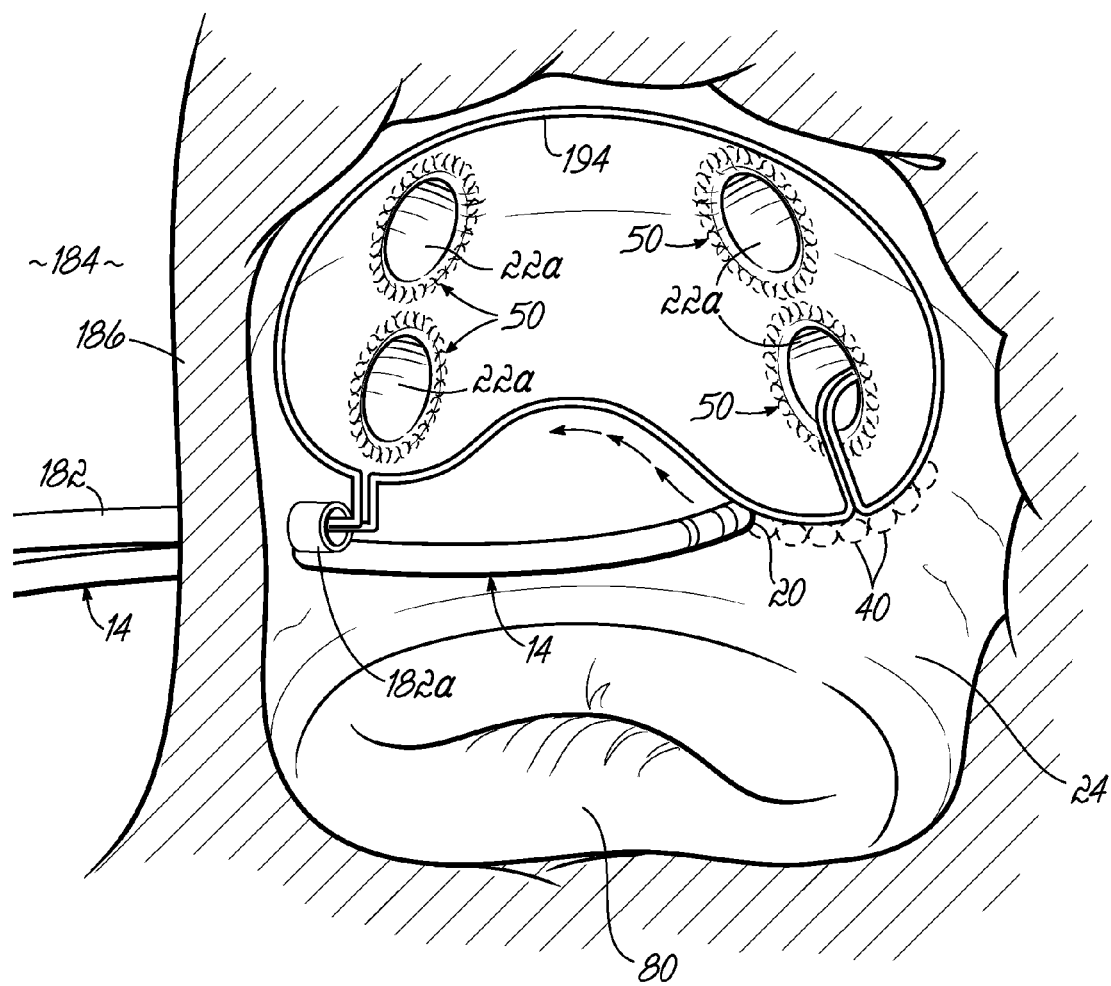
Figure 18L:
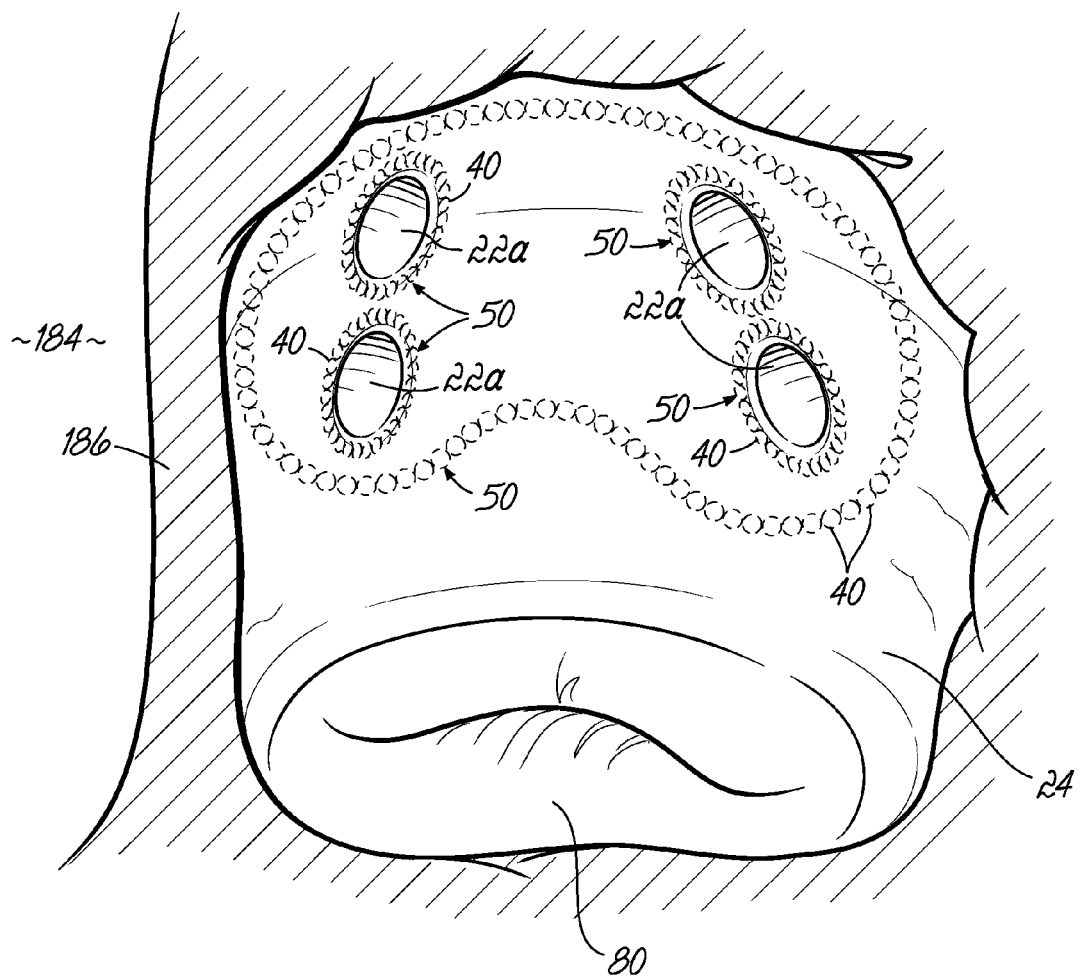

FIG. 18H illustrates the introduction of another template wire 90 through the delivery catheter 182 and into the left atrium 24. The template wire includes a temporary tissue anchoring portion 192. The temporary anchoring portion is formed as a coiled portion of the wire 190 and is inserted into a pulmonary vein opening 22a as illustrated in FIG. 18I to stabilize and anchor the template wire 190, the template wire 190 is then further extended as shown in FIG. 18J and includes a template portion 194 that takes on a preformed shape when unrestrained. The template portion 194 expands to lie against the interior wall of the left atrium 24 in surrounding relation to all of the pulmonary vein openings 22a as schematically illustrated in FIG. 18K. The ablation catheter 14 is then used with the ablating tip portion 20 thereof engaging against the template portion 194 of the wire 190 and selectively activated to apply a pattern of ablation to the tissue on the interior of the atrium 24 along the wire and in surrounding relation to all of the pulmonary vein openings 22a. This procedure results in four individual isolation patterns 50 of the pulmonary veins 22 as well as the larger overall "box" type lesion pattern 50 shown in FIG. 18L.

Figure 19A:
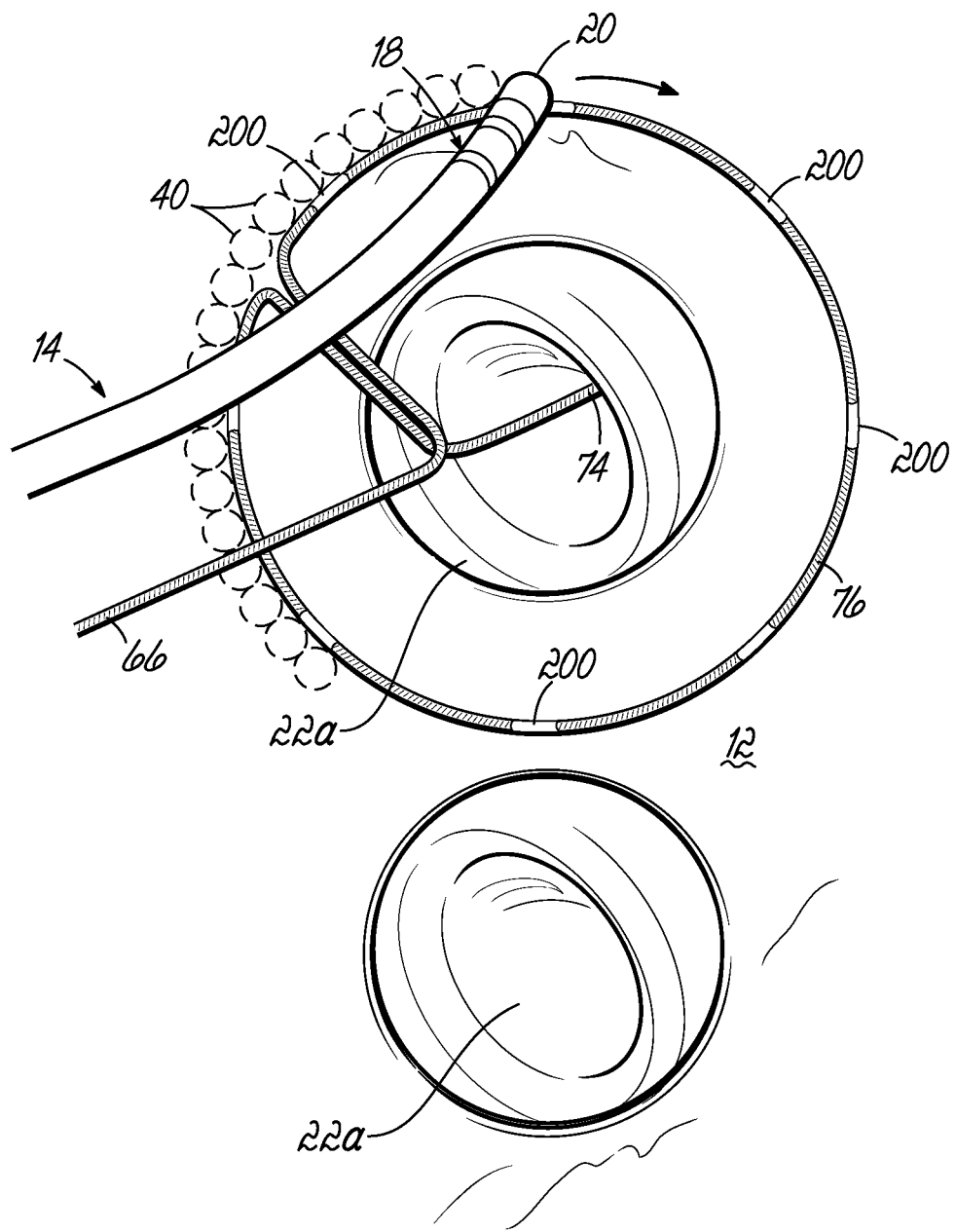
FIGS. 19A-19C illustrate a system constructed in accordance with another embodiment and use thereof to apply a geometric pattern of ablation about two openings associated with pulmonary veins in the left atrium of the heart.
Figure 19B:
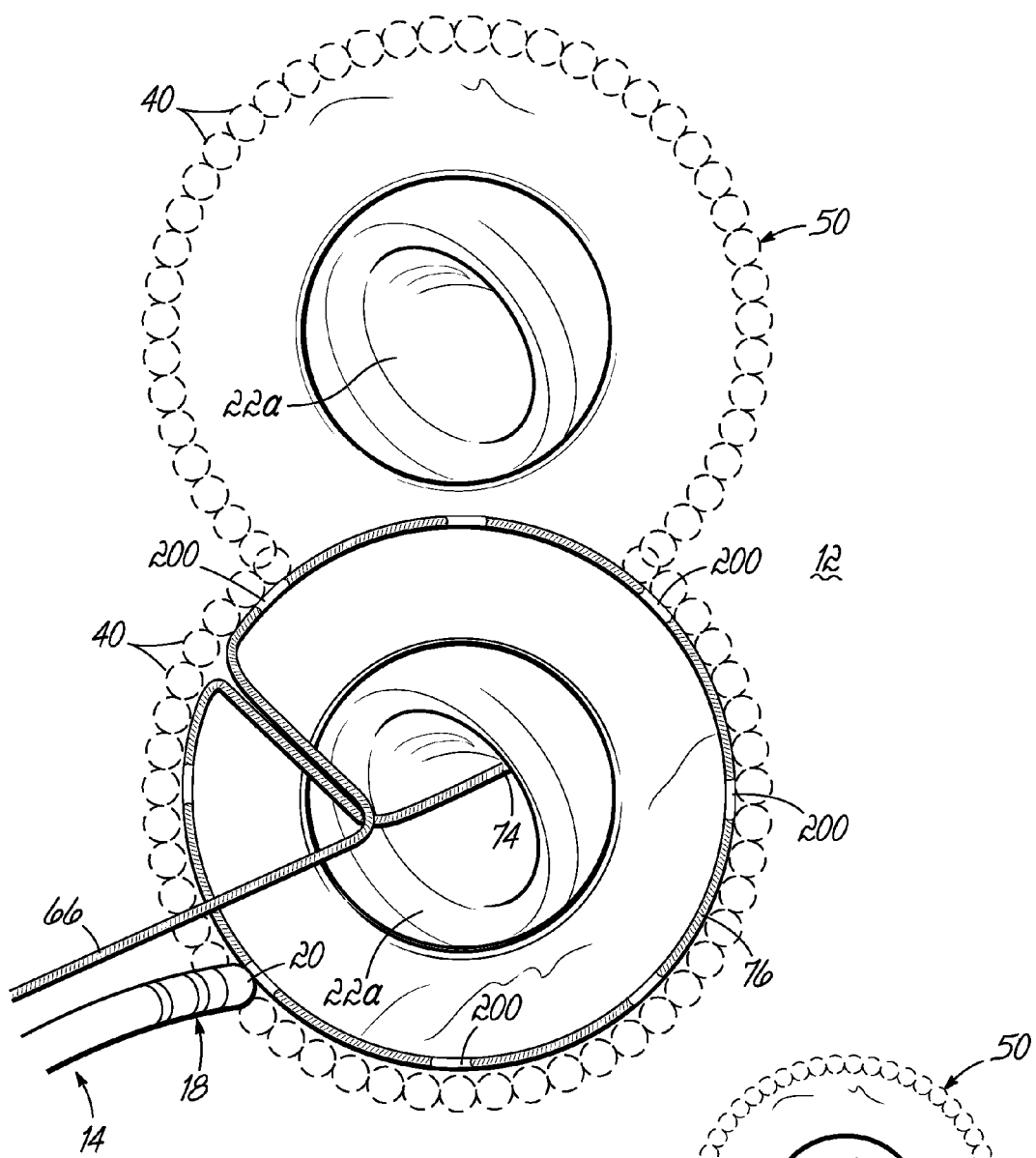
Figure 19C:
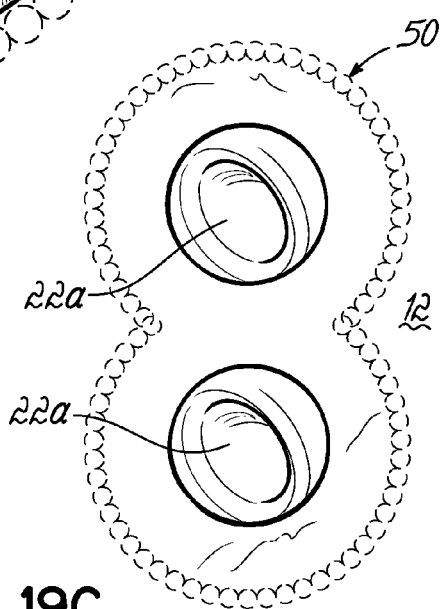

FIGS. 19A and 19B illustrate the use of a template wire 66 to apply a pattern of lesions 40 about or in surrounding relation to two pulmonary vein openings 22a. In this regard, the template wire 66 is anchored as previously discussed within an upper one of the pulmonary vein openings 22a and the ablating tip portion 20 of the ablation catheter 14 is directed around the template portion 76 of the wire 66. Markers 200 are placed on the template portion 76 of the wire. These markers 200 may be radiopaque markers, such that the electrophysiologist may see where to start and stop the ablation pattern, for example, with the aid of X-ray. The same or a different template wire 66 may be inserted into the second or lower pulmonary vein opening 22a allowing the electrophysiologist to complete the pattern of ablation generally into a figure eight, closed geometric shape 50 as shown in FIG. 19B. Again, the markers 200 allow the electrophysiologist to detect where to start and stop the lesions 40. The final lesion pattern 50 is shown in FIG. 19C.

Figure 20A:
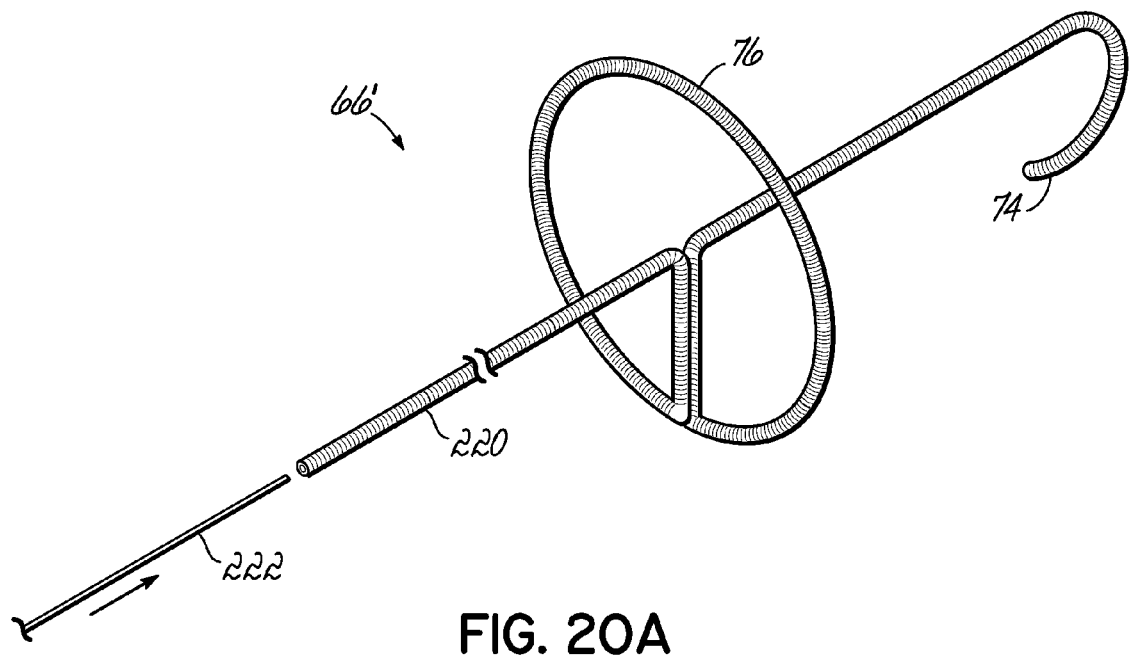
FIGS. 20A-20D illustrate a template wire constructed in accordance with another embodiment.
Figure 20B:
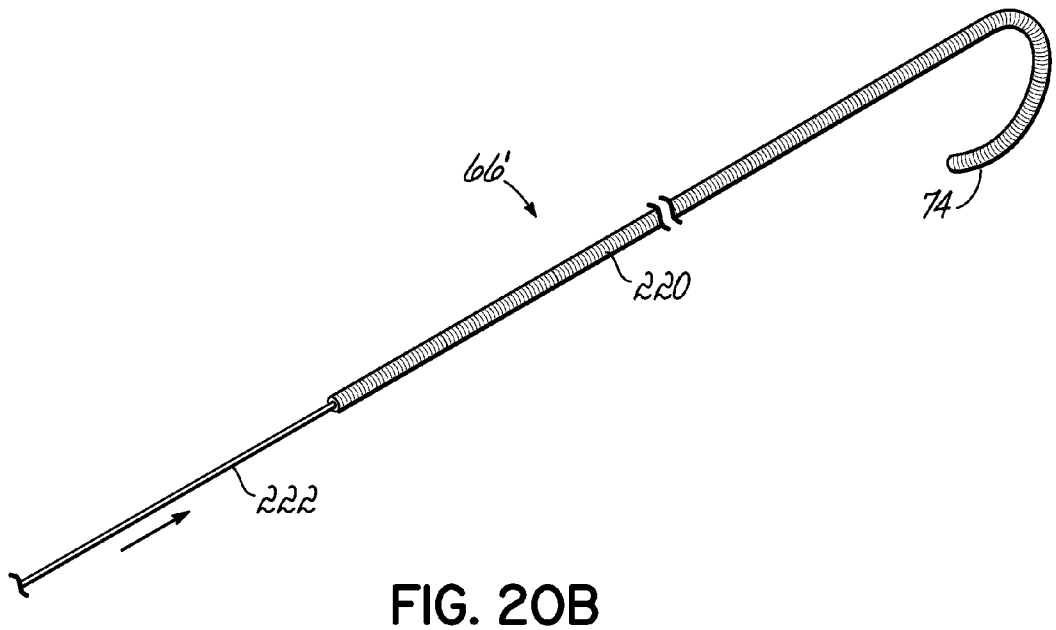
Figure 20C:
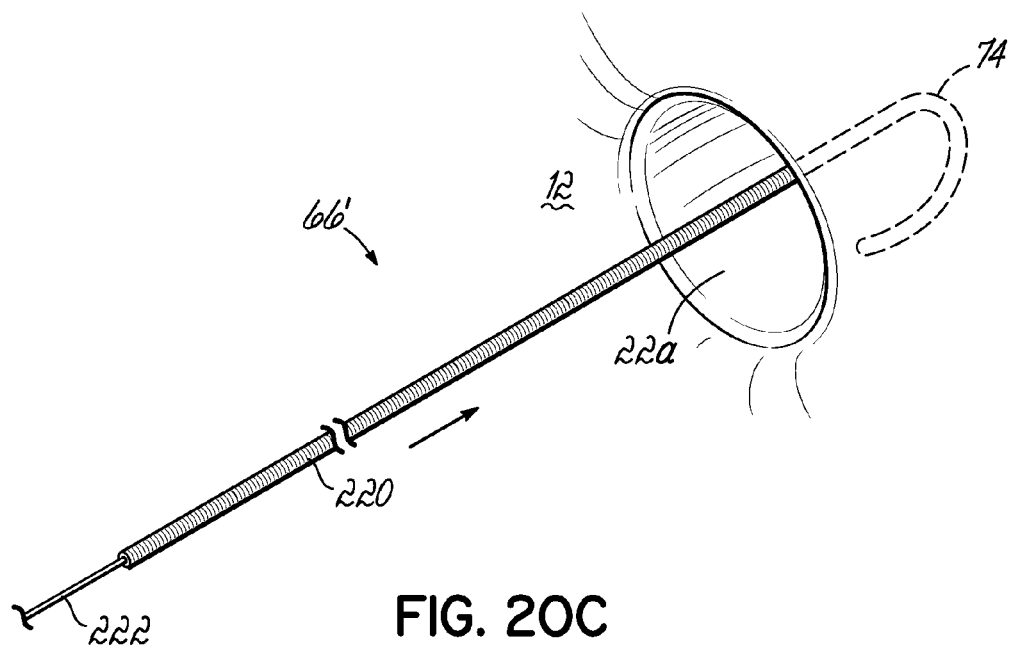
Figure 20D:
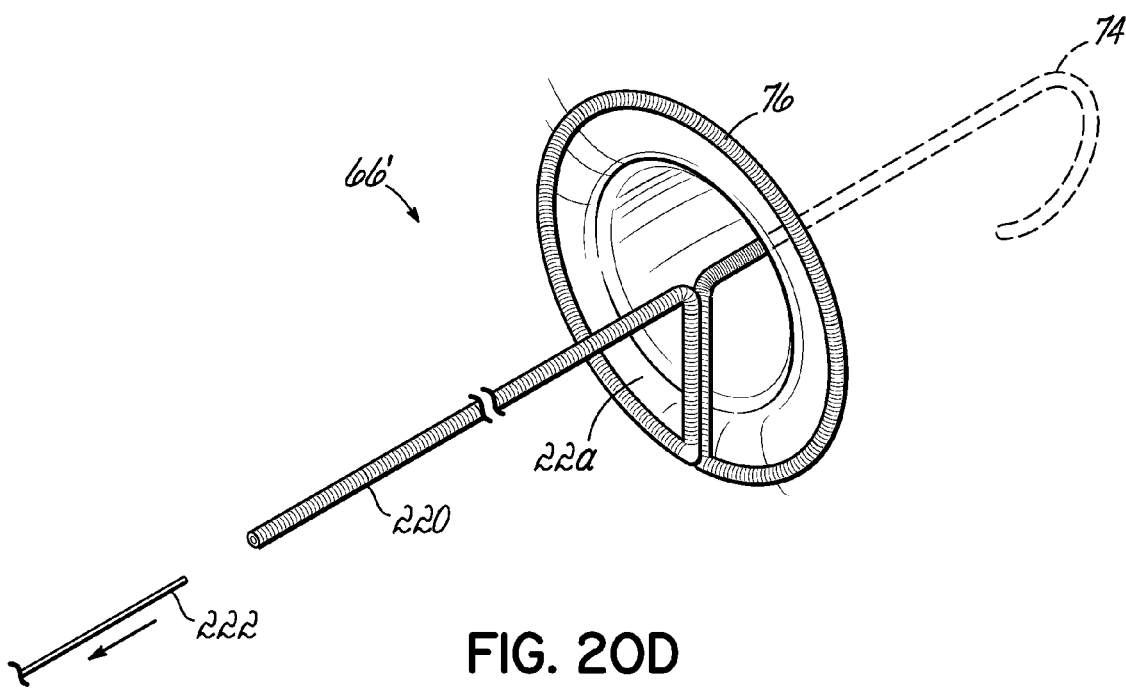

FIGS. 20A-20D illustrate a template wire 66' having a composite construction with an outer coil portion 220 and an inner, removable core wire 222. The outer coil portion 220 is preformed into the shape illustrated in FIG. 20A including the previously discussed temporary anchoring portion 74 and template portion 76. When the core wire 222 is introduced into the hollow center of the coil portion 220, this will straighten out the template wire 66', such as in the form shown in FIG. 20B. In this form, for example, the template wire 66' may be directed percutaneously into the desired location, such as with the anchoring portion 74 within one of the pulmonary vein openings 22a (FIG. 20C) to temporarily anchor the template wire 66'. Then, the core wire 222 may be withdrawn as shown in FIG. 20B allowing the outer coil portion 220 of the template wire 66' to take on its preformed shape. This forms the template portion 76 as shown in FIG. 20D. This will then allow the ablation method to be performed, such as in one of the manners discussed herein.

Figure 21:
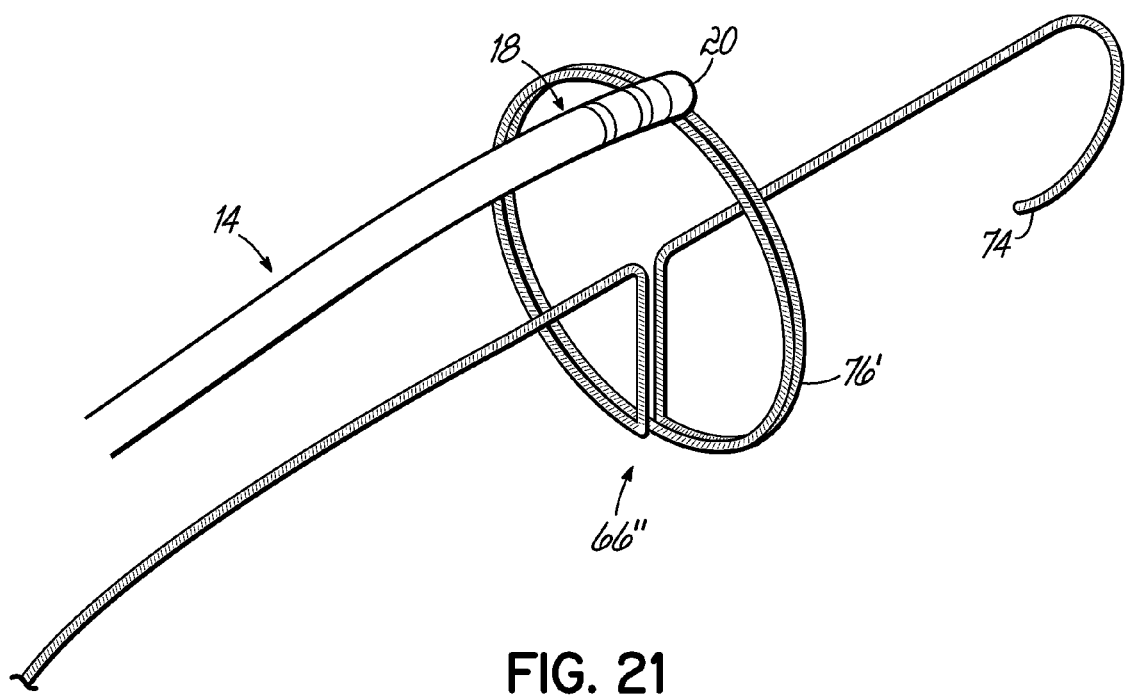
FIG. 21 illustrates a template wire constructed in accordance with another embodiment, as well as an ablation catheter in position to be guided by a template portion of the template wire.

FIG. 21 illustrates a template wire 66" constructed in accordance with another embodiment, similar to that shown in FIGS. 20A-20D, but illustrating a double coil design for the template portion 76' and schematically illustrating the ablating tip portion 20 of an ablation catheter 14 in engagement with the double coil template portion 76 for guidance during an ablation procedure as generally discussed herein.

Figure 22:
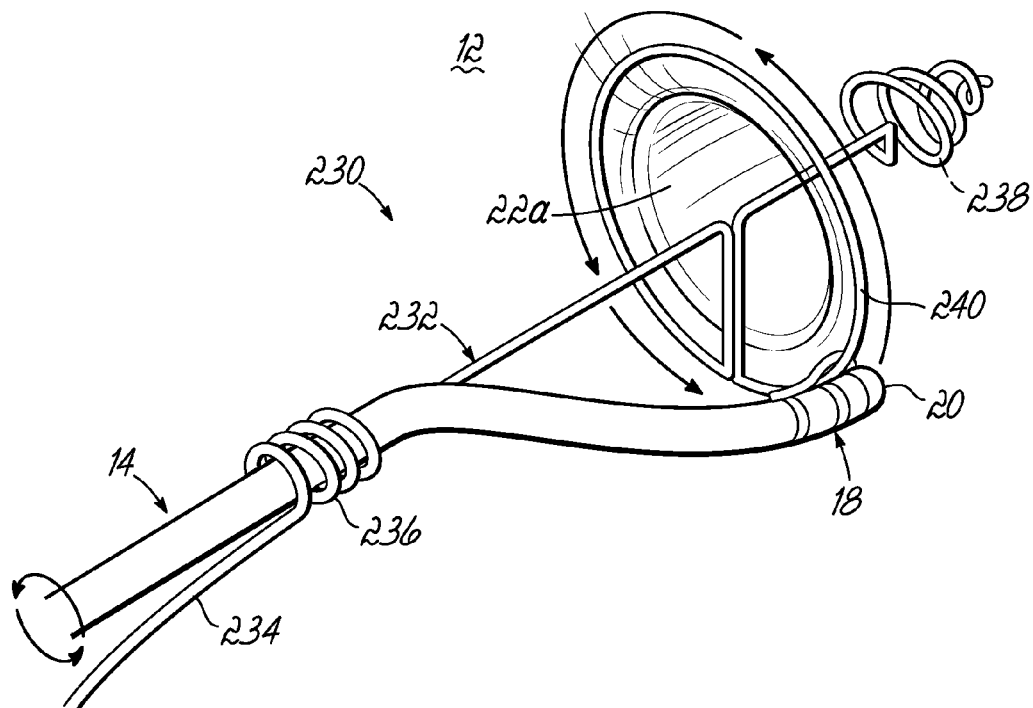
FIG. 22 is a schematic, perspective view of a system constructed in accordance with another embodiment.

FIG. 22 illustrates an alternative system 230 that includes a guiding device 232 and an ablation catheter 14 connected thereto. The guiding device 232 comprises a wire 234 that is coupled to the ablation catheter 14 with a coiled portion 236 thereof through which the ablation catheter 14 extends. The guiding device 232 further includes a coiled section 238 at the distal tip thereof for providing the temporary tissue anchoring portion. The ablating tip 20 of the ablation catheter 14 is physically coupled to a template portion 240 of the wire 234 using a suitable connection such as a hook-type connection 242 as shown. In this manner, the ablation catheter 14 is physically coupled for movement with respect to the guiding device 232 in the two locations, including at the coiled portion 236 and the hook-type connector 242. The ablating tip 20 of the ablation catheter 14 may be moved around the template portion 240 of the wire 234 as the ablating tip portion 20 is activated to create lesions as generally described herein. The movement of the ablation catheter 14 may be a rotation generally about its long axis as shown.

Figure 23:
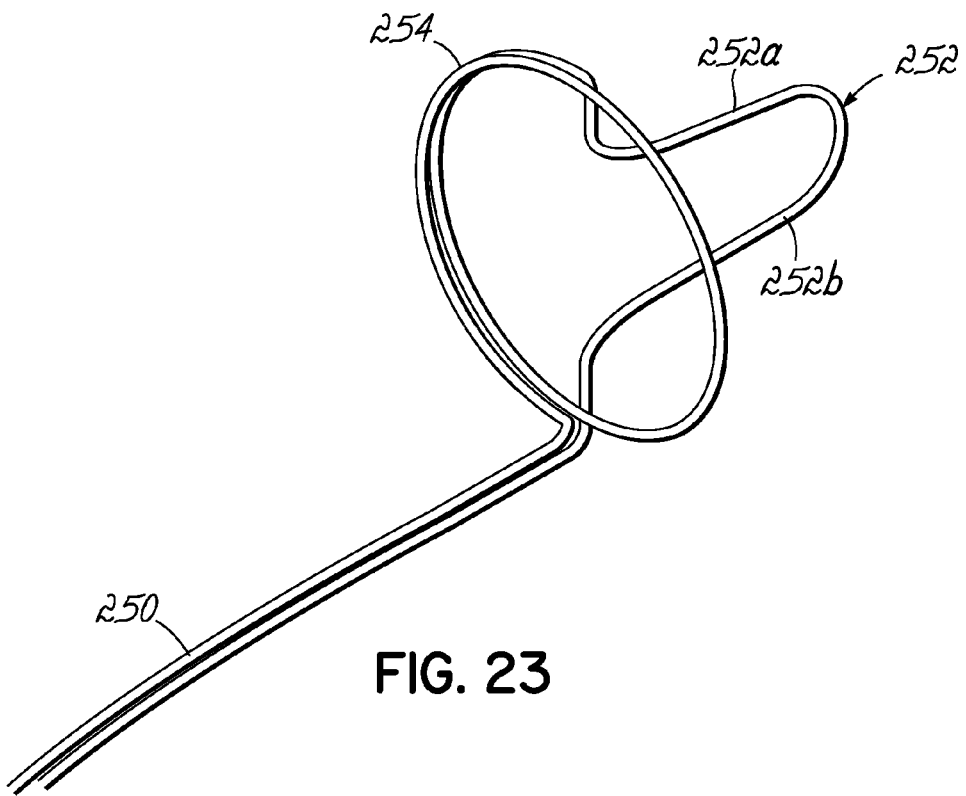
FIG. 23 is a perspective view of a template wire constructed in accordance with another embodiment.

FIG. 23 illustrates another alternative embodiment of a template wire 250 that includes a temporary tissue anchoring portion 252 at a distal end and a template portion 254. This embodiment and similar embodiments illustrate that the template wire 250 may be formed to "double back" on itself. For example, this will avoid any sharp wire end being manipulated within the heart. In this embodiment, the tissue anchoring portion 252 generally comprises a U-shaped section of the wire 250 that, again, may be anchored using a friction fit within one of the pulmonary vein openings as discussed herein. Two legs 252a, 252b provide the temporary anchoring function and may or may not bias toward one another to perform this anchoring function.

Figure 24:
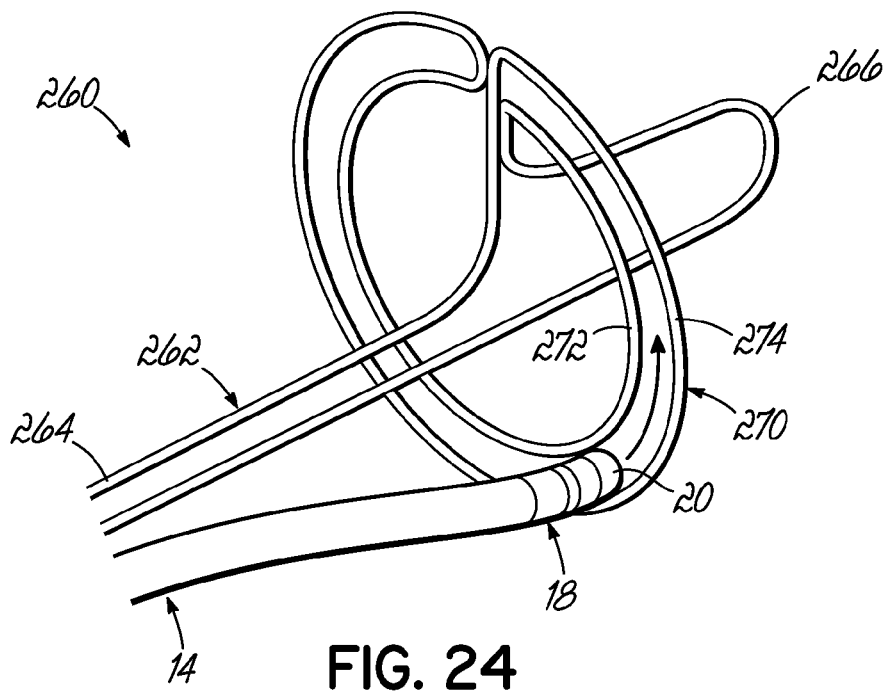
FIG. 24 is a perspective view illustrating another embodiment of a template wire and an ablation catheter being used therewith.

FIG. 24 illustrates a system 260 in accordance with another embodiment in which the guiding device 262 comprises a template wire 264 including a generally U-shaped tissue anchoring portion 266 for insertion into a pulmonary vein opening, and a template portion 270 that includes spaced apart wire portions 272, 274 forming a track. The ablating tip portion 20 of the ablation catheter 14 is positioned within the track between the two spaced apart wire portions 272, 274 to provide further guidance for the ablating tip portion 20 as it is moved around the template portion 270 to create a pattern of ablation as generally described herein.

Figure 25:
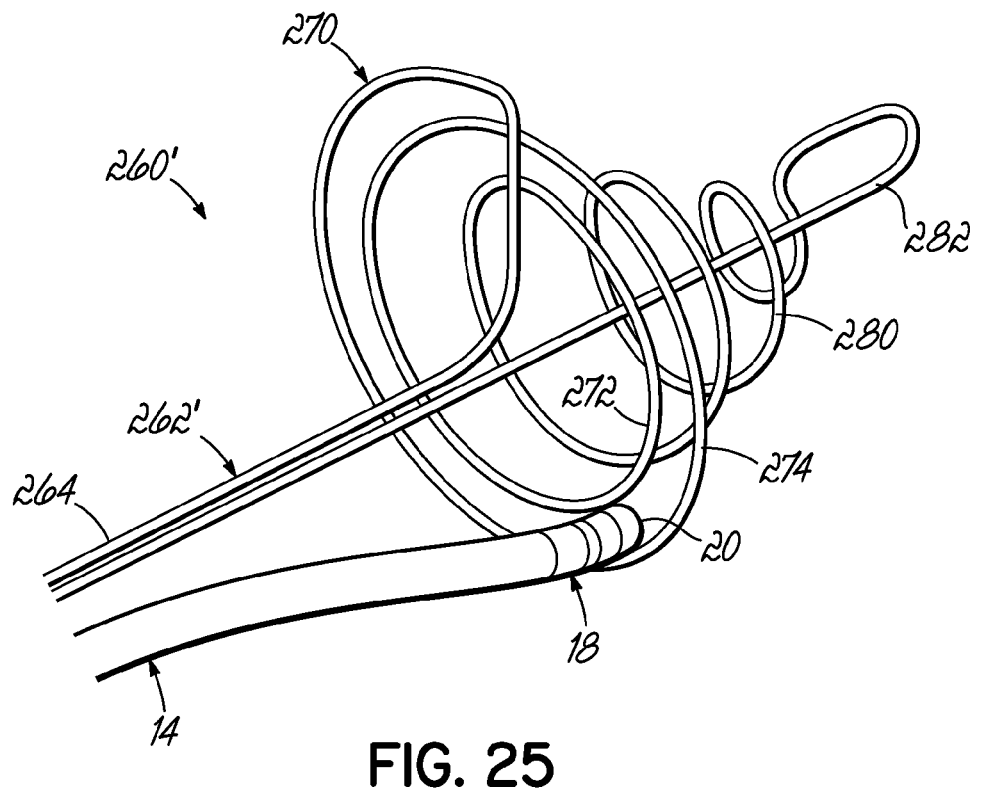
FIG. 25 is a perspective view of a template wire constructed in accordance with another embodiment and being used with an ablation catheter.

FIG. 25 illustrates another embodiment of system 260' including a guiding device 262' similar to FIG. 24, but including a differently configured tissue anchoring portion having a coiled portion 280 and U-shaped portion 282 for insertion and retention in a pulmonary vein opening.

Figure 26:
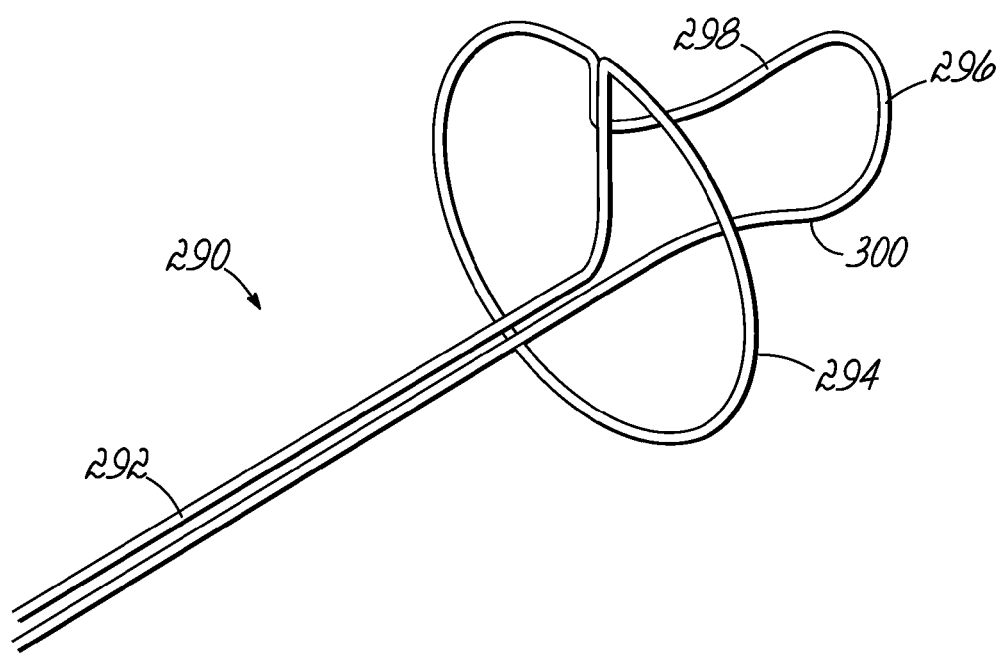
FIG. 26 is a perspective view illustrating a template wire constructed in accordance with another embodiment.

FIG. 26 illustrates another embodiment of a guiding device 290 comprising a template wire 292 including a template portion 294 and a tissue anchoring portion 296 used generally in the manners described herein. Again, in this case, the tissue anchoring portion 296 is generally U-shaped with leg portions 298, 300 of the U-shape engaging the interior walls of the pulmonary vein with a friction and/or biased or resilient fit.

Figure 27:
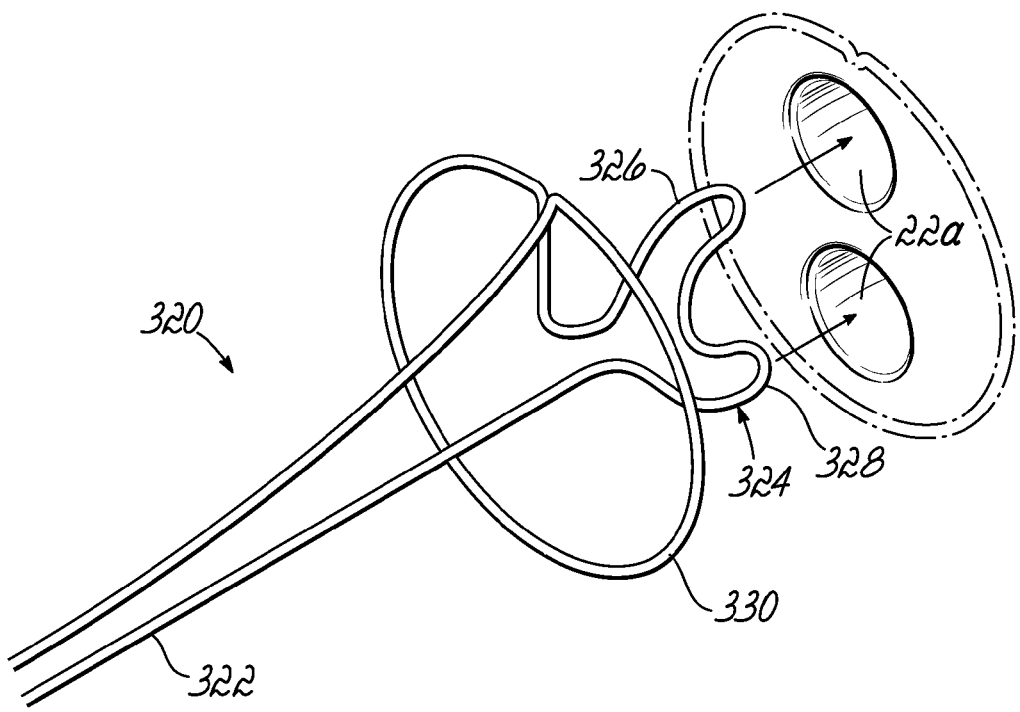
FIG. 27 is a perspective view illustrating a template wire constructed in accordance with another embodiment.

FIG. 27 illustrates another alternative embodiment of a guiding device 320 comprising a template wire 322 including a tissue anchoring portion 324 which includes two generally U-shaped segments 326, 328. The segments 326, 328 are respectively insertable and temporarily retained within two separate pulmonary vein openings 22a whereby a template portion 330 will engage against tissue surrounding both openings 22a as schematically illustrated in dash-dot lines. Once situated in this manner and temporarily anchored, the template portion 330 may be utilized to guide an ablation catheter tip portion generally as described herein.

FIG. 28 schematically illustrates the interior of the left atrium 24 of a heart and a system 350 constructed in accordance with another embodiment. In this embodiment, the template wire 190 is generally of a configuration previously described (see FIG. 18K) with the template portion 194 of the wire 190 surrounding more than one pulmonary vein opening 22a and individual surrounding patterns 50 of lesions 40 having been applied around each of the pulmonary vein openings 22a. In this embodiment, a connector 352 comprising a wire loop is located between the template wire 190 and the ablation catheter 14. This wire loop 352 forms a more positive engagement between the template portion 194 of the template wire 190 and the ablation catheter 14 as the lesions 40 are formed. An additional delivery catheter 354 is also shown for holding delivery catheter 182 and ablation catheter 14.

FIGS. 29A-29D illustrate various other examples of connectors that may be utilized between the ablation catheter 14 and the template wire. In FIG. 29A, the connector comprises a hook-type connector 360. In FIG. 29B, the connector comprises a coil connector 362 through which the template wire will extend. In FIG. 29C the connector comprises a more direct loop connector 364 than the loop connector 352 shown in FIG. 28. FIG. 29D illustrates the clip-type connector 366. In this embodiment, the template wire may be clipped between the connector 366 and the ablation catheter 14 while still allowing movement therebetween to allow the ablating tip portion to ride along the template wire generally as illustrated in FIG. 28.

Figure 30A:
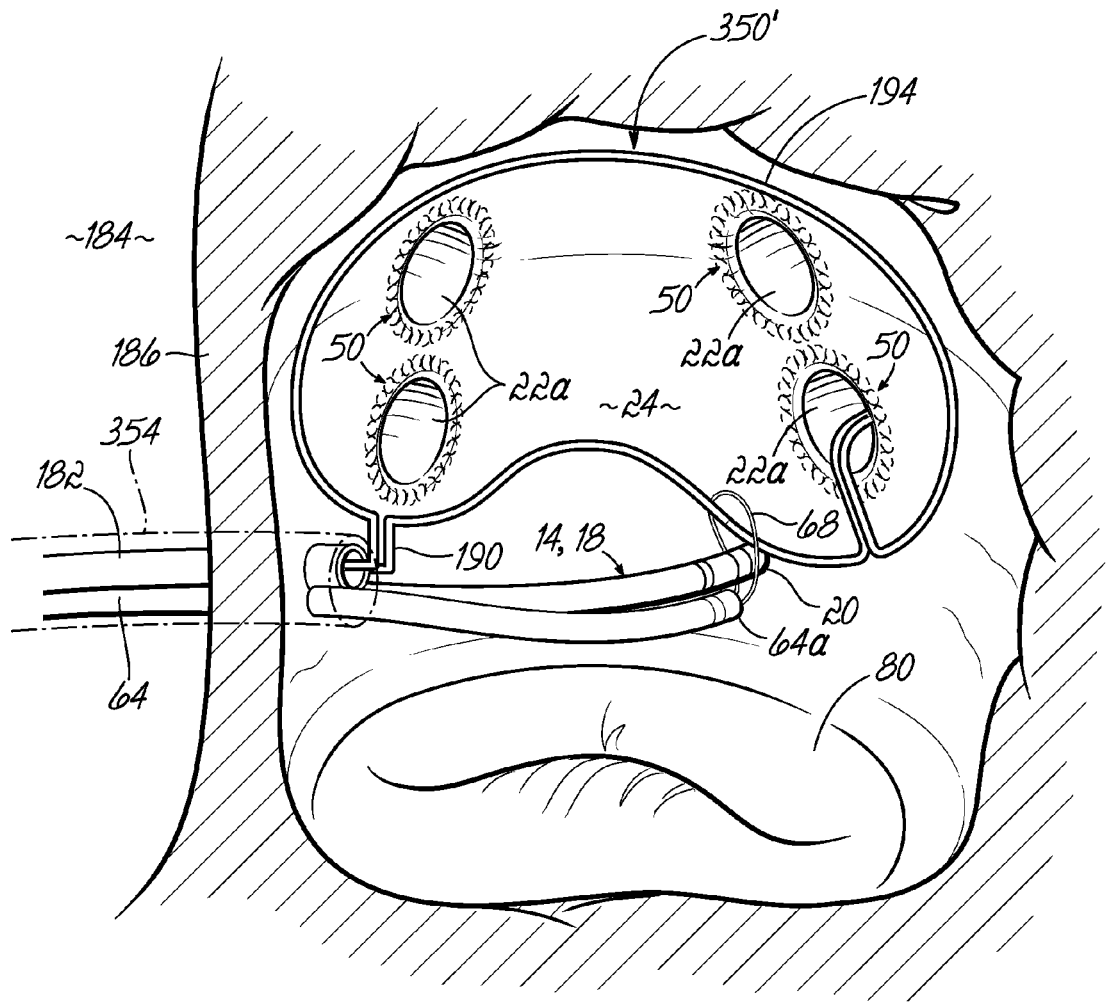
FIGS. 30A-30I illustrate a system constructed in accordance with another embodiment and respective steps in a method of use for the system.
Figure 30B:
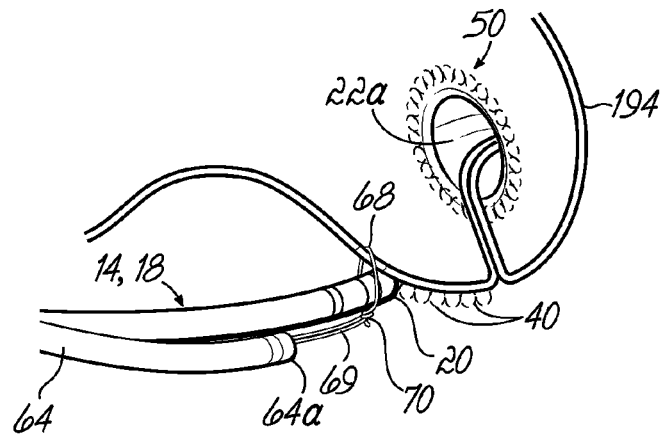
Figure 30C:
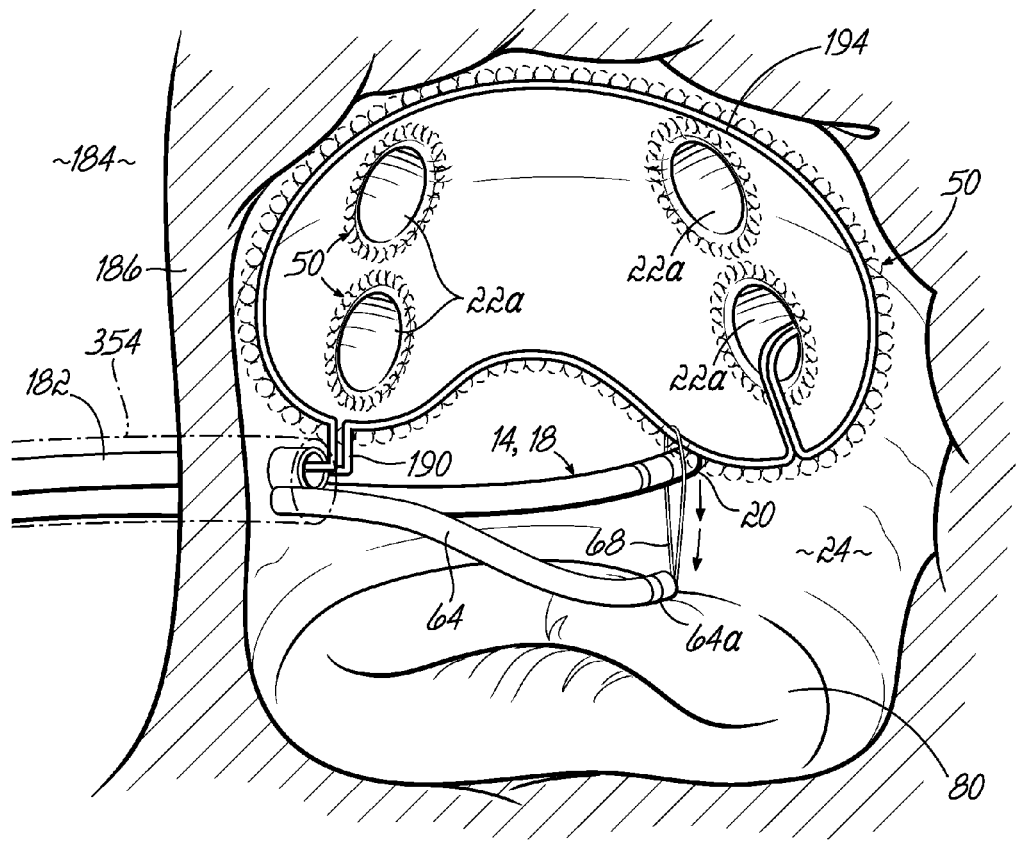
Figure 30D:
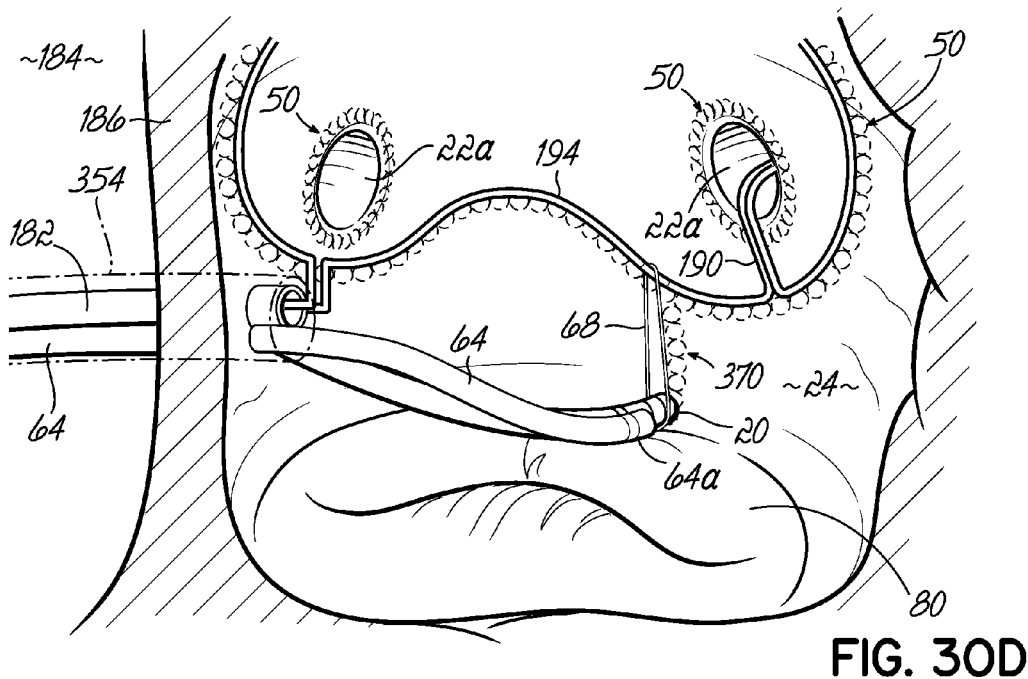
Figure 30E:
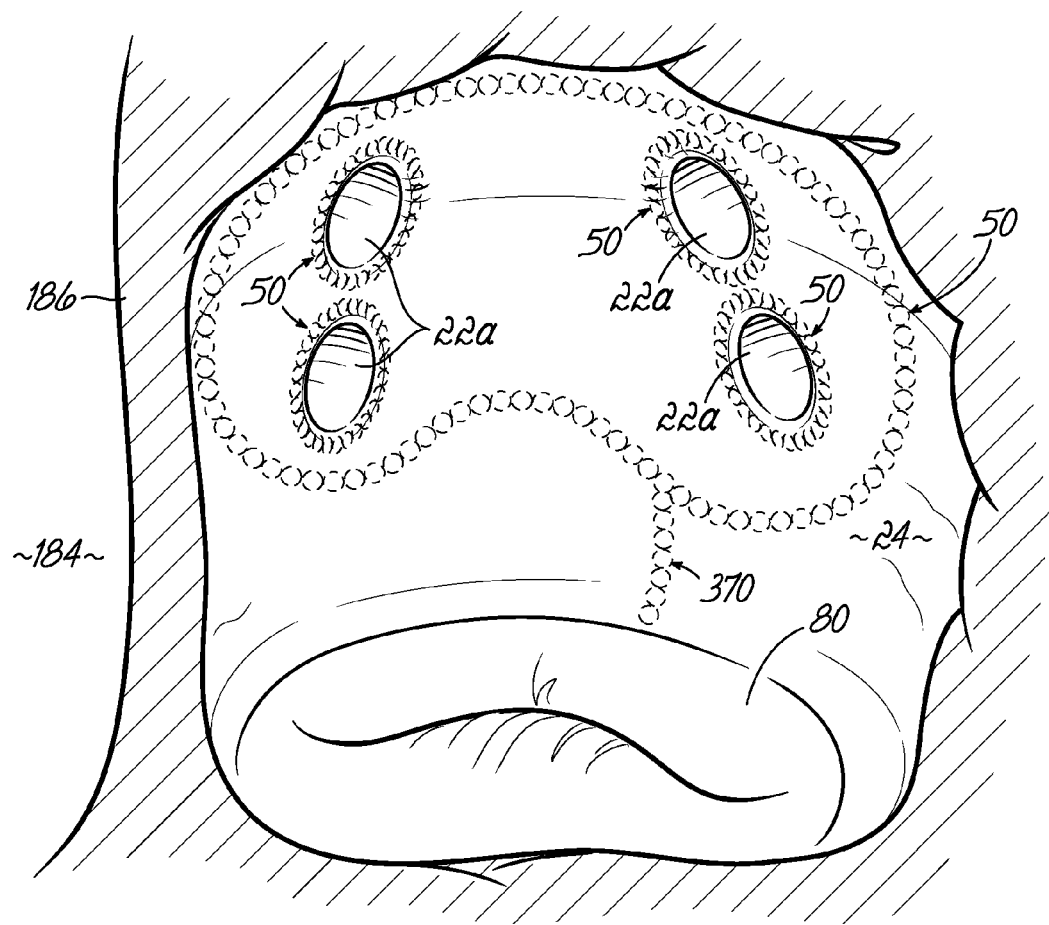
Figure 30F:
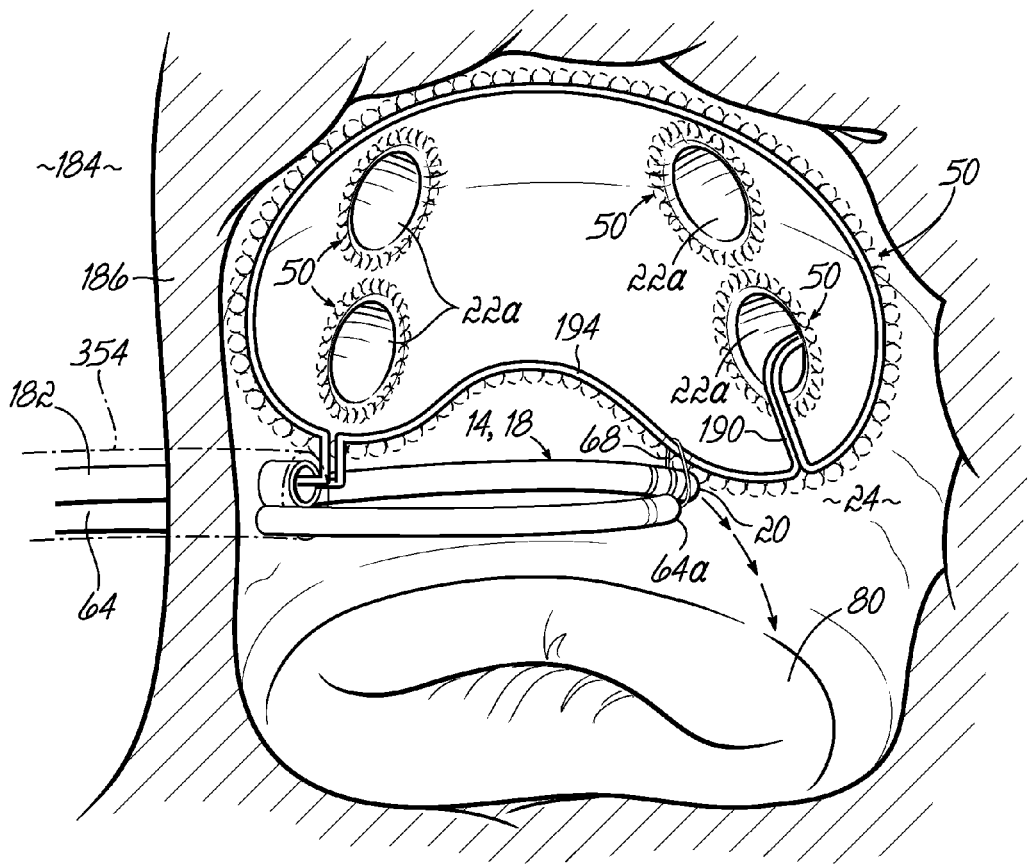
Figure 30G:
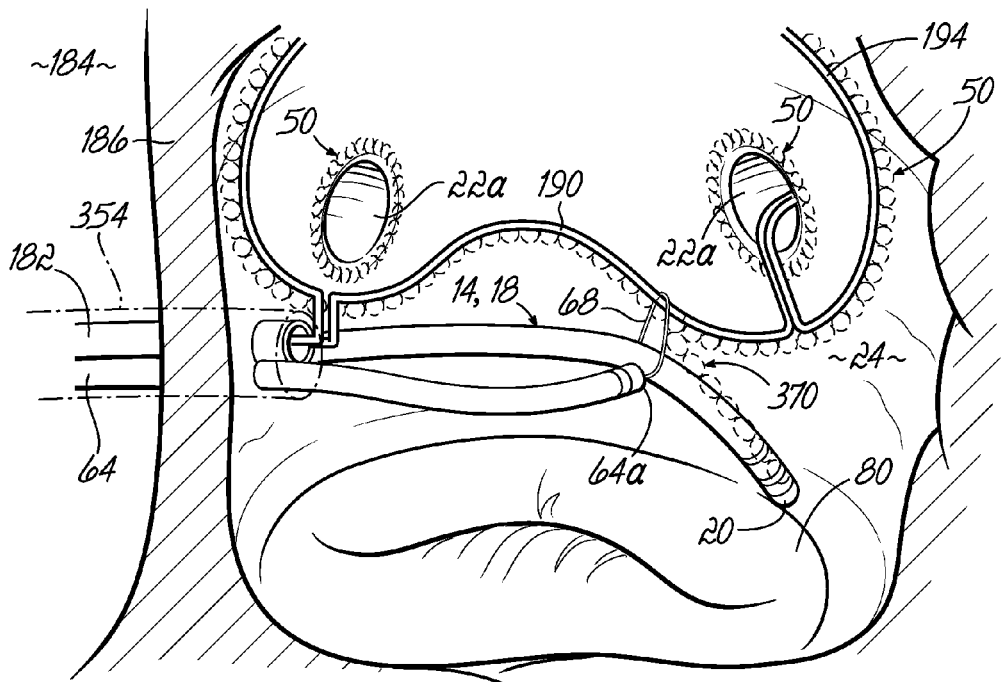
Figure 30H:
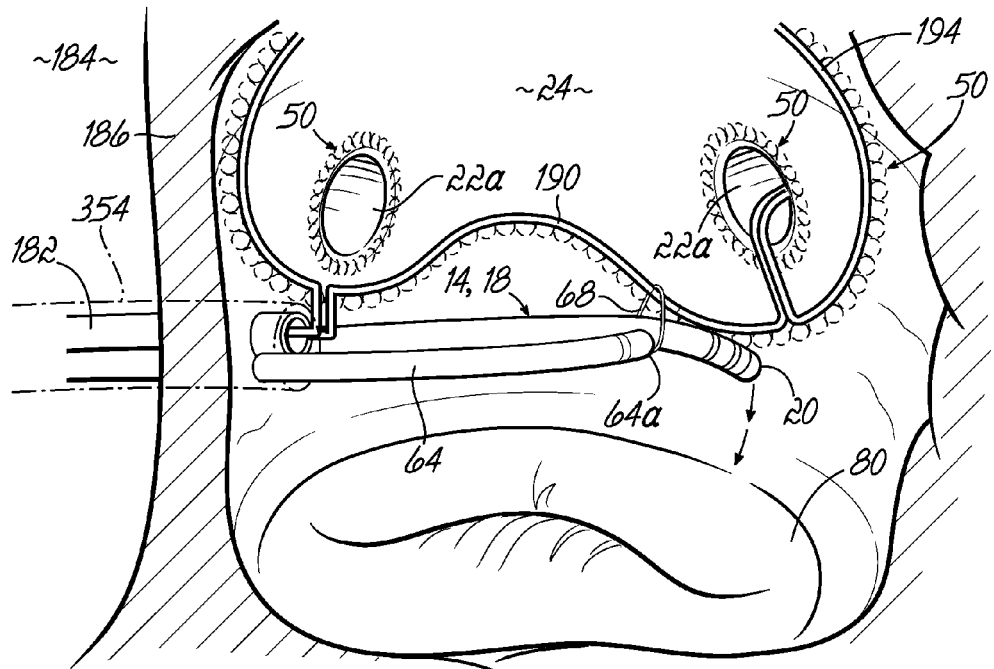
Figure 30I:
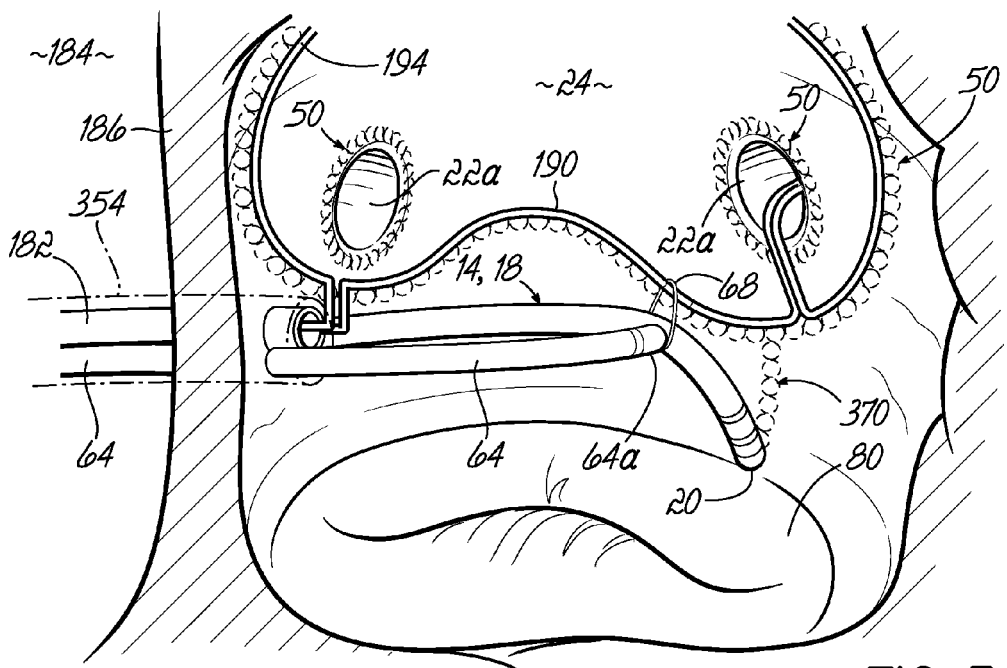

FIGS. 30A through 30D illustrate a system 350' similar to that shown in FIG. 28, but illustrating a suture loop connector or snare 68 capturing both the template wire 190 and the ablation catheter 14. The slip knot 70 (FIG. 30B) is tightened to more securely engage the ablating tip 20 against the template wire 190 as the pattern of ablation is applied as shown in FIG. 30B. FIG. 30C illustrates that the slip knot 70 may be loosened to then allow more freedom of movement for the ablating tip 20. In this manner, and as illustrated in FIG. 30D, a linear pattern 370 of lesions may be formed starting from the previously applied, large box pattern 50, to the mitral valve 80 in the wall of the left atrium 24. The resulting patterns 50, 370 of lesions 40 may then be those shown in FIG. 30E. FIGS. 30F and 30G, as well as FIGS.

30H and 30I illustrate additional methods of using the guiding device and, more particularly, the positioning catheter 64 to assist with forming the straighter pattern of lesions 370 from the box pattern 50 to the mitral valve 80. The ablation catheter 14 will typically have steering control at its distal tip and this steering ability may be used with the suture snare 68 slightly loosened but still providing firm support to allow the ablating tip portion 20 to create the necessary lesions.

Figure 31A:
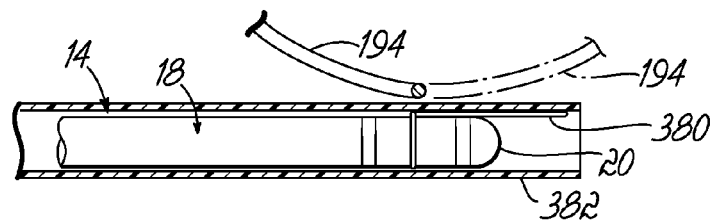
FIGS. 31A-31C schematically illustrate an alternative coupling or connection formed between the ablation catheter and template wire.
Figure 31B:
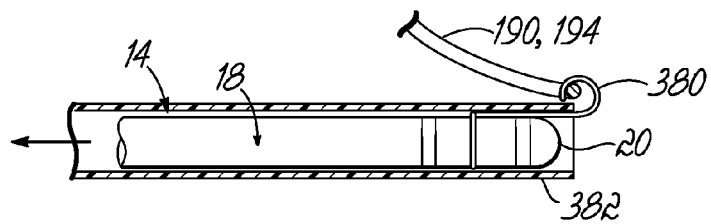
Figure 31C:
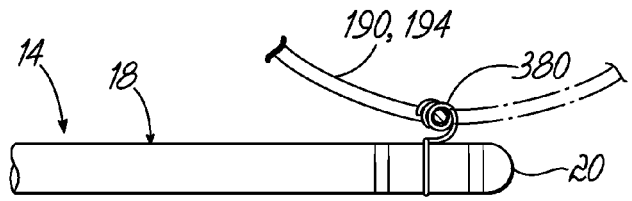

FIGS. 31A-31C illustrate an alternative coupling or connection between the distal end 18 of the ablation catheter 14 and the template wire 190, 194. In this regard, a coupling wire segment 380 is connected to the ablation catheter 14 and retained in a straightened condition by a sheath 382. When the sheath 382 is withdrawn proximally relative to the ablation catheter 14, the coupling wire segment 380 will be actuated into a preformed coiled condition to coil around the template wire 190, 194 in a manner allowing movement of the ablating tip portion 20 relative to the template wire 190, 194, such as lengthwise along the template wire 190, 194. As discussed herein, such a coupling will allow the ablation catheter 14 and ablating tip portion 20 to be moved along a predetermined pattern to create one or more lesions designed to promote normal sinus rhythm of the heart.

Figure 32A:
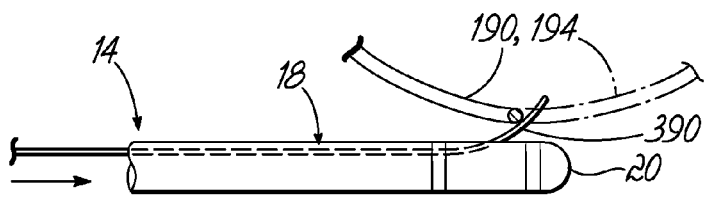
FIGS. 32A and 32B are schematic views illustrating another alternative coupling or connection between the ablation catheter and the template wire.
Figure 32B:
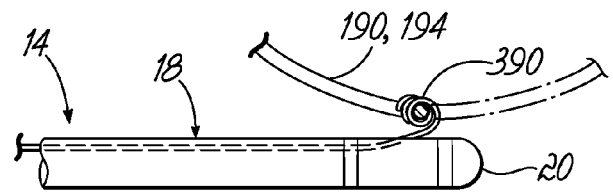

FIGS. 32A and 32B illustrate an alternative connection to that shown in FIGS. 31A-C. In this regard, the coupling wire segment 390 is positioned within a lumen of the ablation catheter 14 and may be extended distally therefrom as shown such that the distal end of the coupling wire segment 390 coils into a preformed shape around the template wire 190, 194. Once coupled in this manner, again the ablating tip portion 20 of the ablation catheter 14 may be moved along and, in limited fashion, toward and away from the template wire 190, 194 to apply a pattern of ablation to the tissue.

Figure 33A:
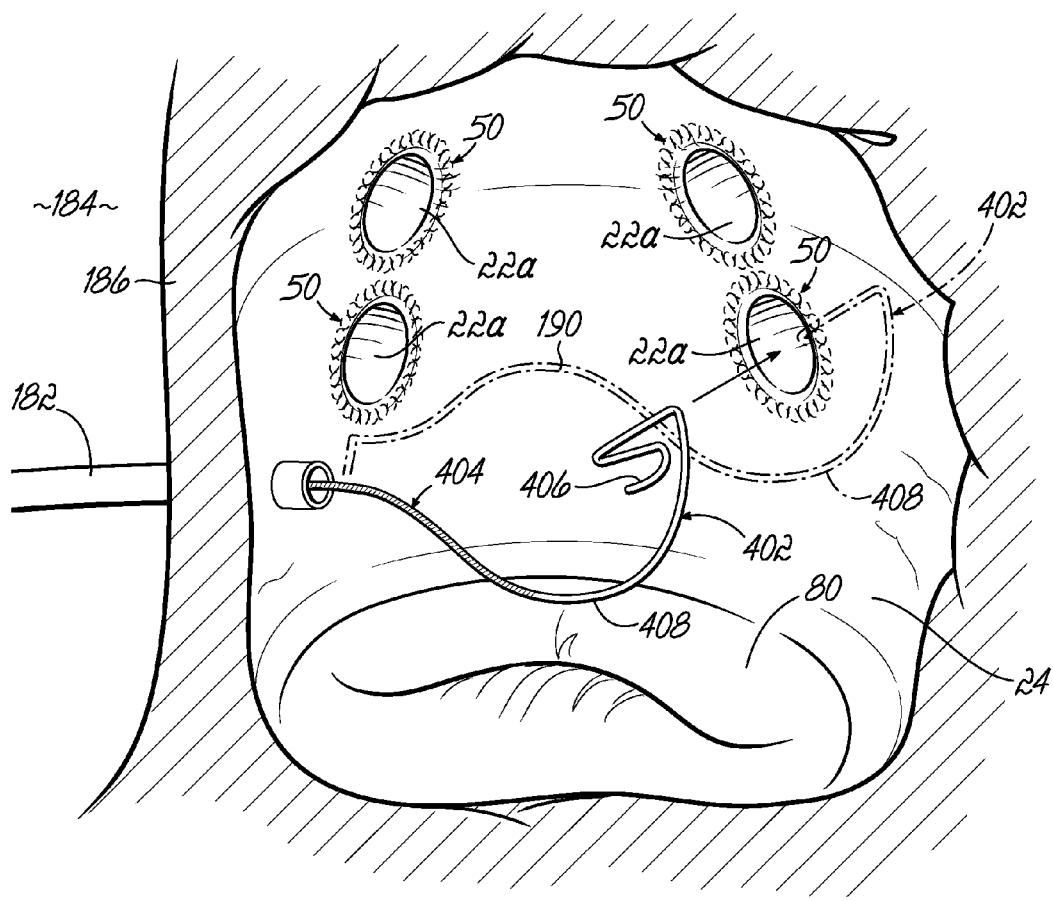
FIGS. 33A and 33B illustrate a template wire constructed in accordance with another embodiment to apply a pattern of ablation corresponding to the portion of a closed, geometric shape extending around all pulmonary veins in the left atrium.
Figure 33B:
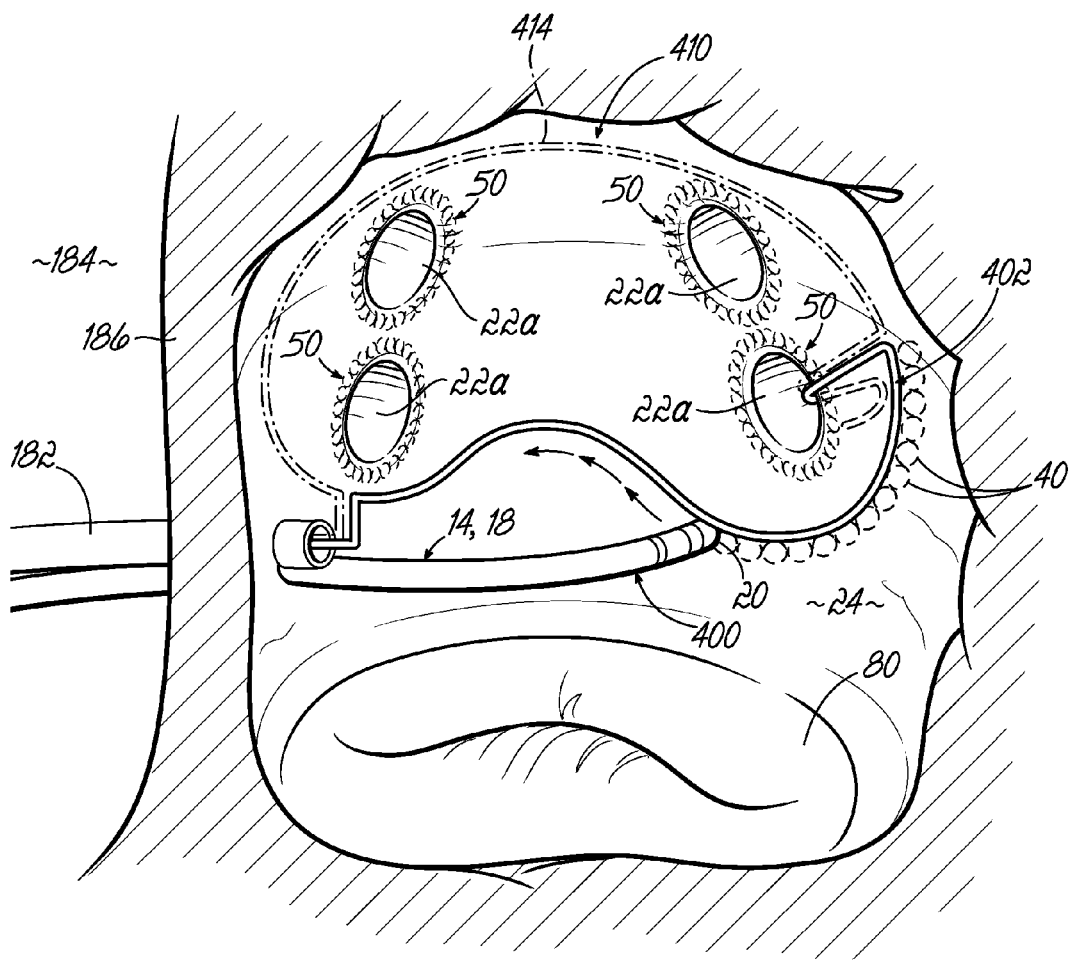
Figure 33C:
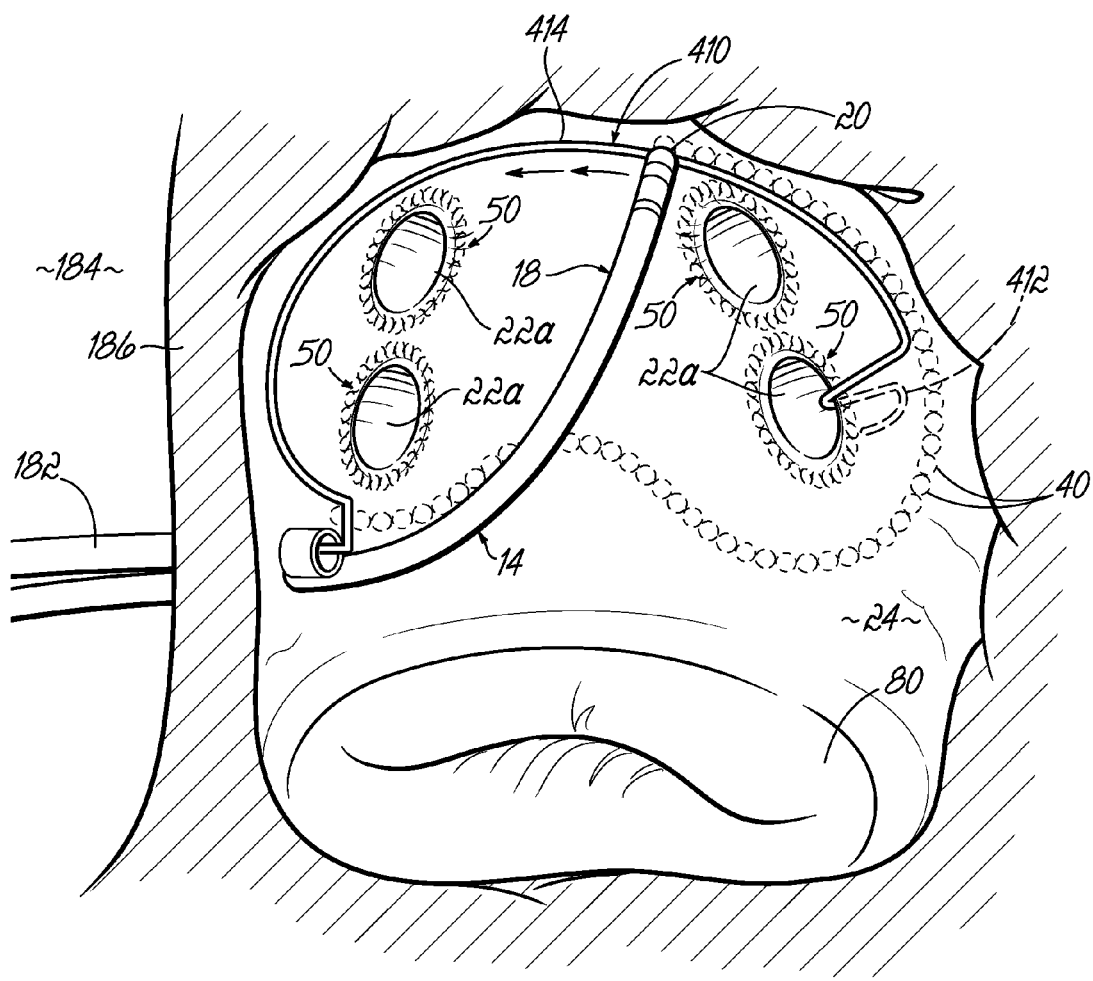
FIG. 33C illustrates another template wire constructed to apply the remaining portion of the closed geometric pattern of ablation.

FIGS. 33A and 33B illustrate another alternative system 400 (FIG. 33B) comprising a guiding device 402 and an ablation catheter 14. In this system 400, the delivery catheter 182, as previously discussed, is delivering a template wire 404 into the left atrium 24 so as to extend along a portion of the ablation pattern desired. In this example, the template wire extends partially about two lower pulmonary vein openings 22a once it has been extended from the delivery catheter 182 and takes on a preformed shape. A tissue anchoring portion 406 is inserted into one of the pulmonary vein openings 22a. Once located and retained in this manner, as illustrated in FIG. 33B, the ablation catheter 14 may be used to apply a pattern of ablation along the template portion 408, such as in the manner shown. In a subsequent step, another template wire 410 is introduced into the left atrium 24 and secured into one of the pulmonary vein openings 22a. In this example, this template wire 410 includes a temporary anchoring portion 412 that extends into the same pulmonary vein opening 22a as the template wire 404 shown in FIGS. 33A and 33B. This secures the template wire 410 in position to extend around the remaining upper pulmonary vein openings 22a and apply the remainder of a closed pattern of ablation creating lesions 40 in a desirable "box pattern" along a template portion 414, as shown in FIG. 33C.

Figure 34A:
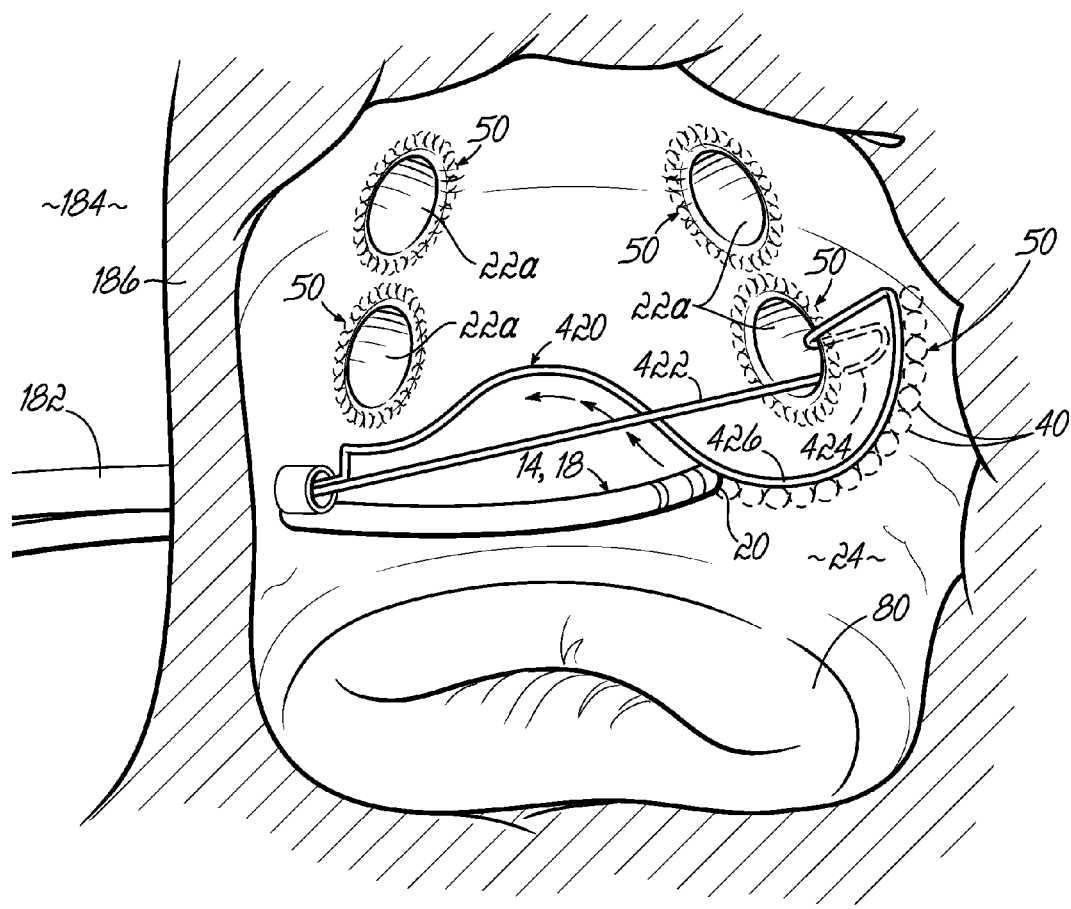
FIGS. 34A and 34B illustrate a template wire constructed in accordance with another embodiment for applying a portion of the ablation pattern similar to FIG. 18L.
Figure 34B:
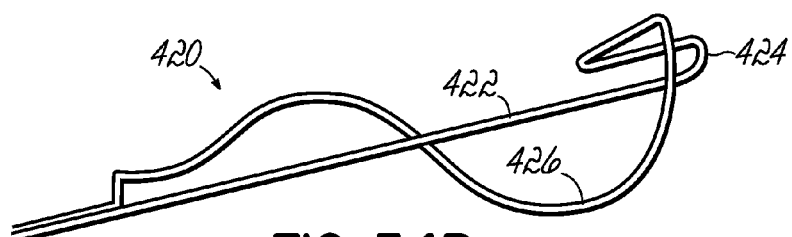

FIGS. 34A and 34B illustrate an alternative guiding device 420 that is similar to that shown in FIGS. 33A and 33B, but includes a wire stiffening section 422 to supply greater support. In a manner similar to other embodiments, and for similar purposes, a tissue anchoring portion 424 and a template portion 426 are provided.

Figure 34C:
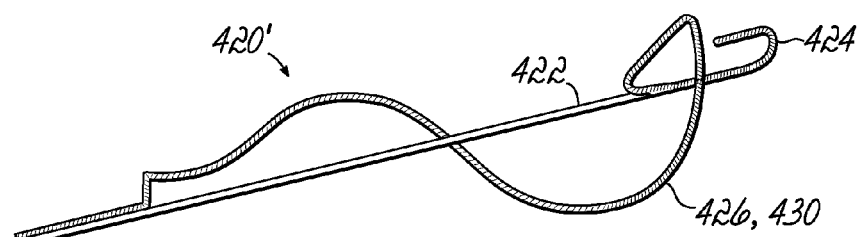
FIG. 34C is a view similar to FIG. 34B, but illustrating another alternative template wire.

FIG. 34C illustrates another alternative embodiment of a guiding device 420' similar to that shown in FIGS. 34A and 34B, but illustrating that a portion 430 of the wire template 420' may be formed from a coiled, flexible construction, while the remaining portion 422 may be formed from a stiffer construction such as wire providing greater support.

Figure 35:
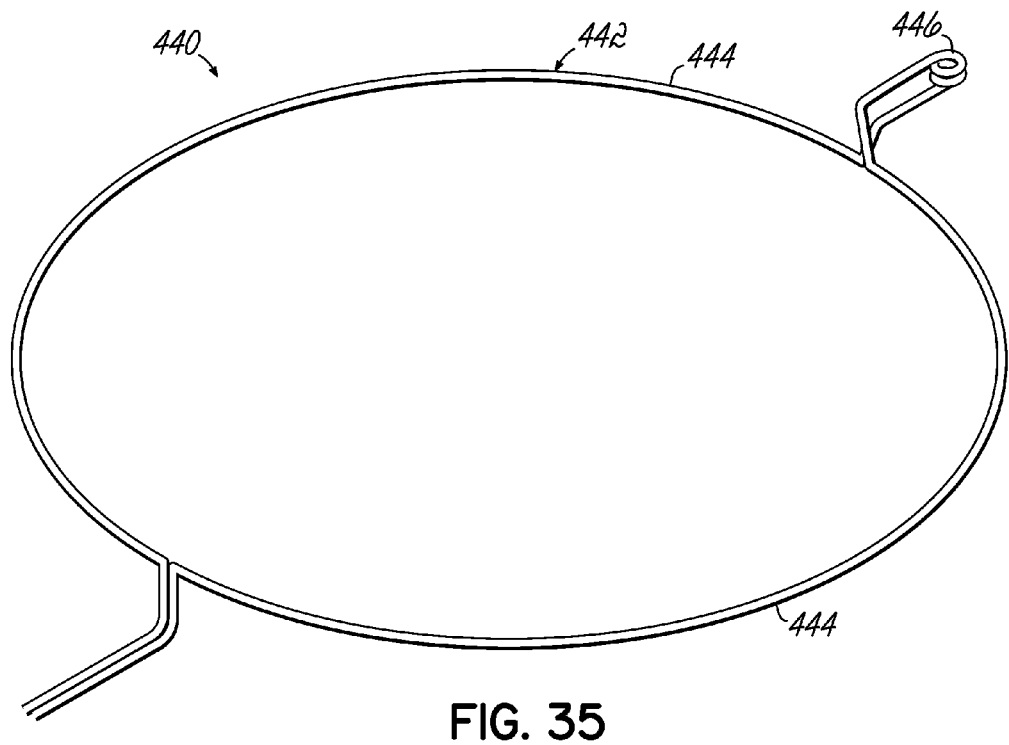
FIG. 35 is a perspective view illustrating another alternative template wire.

FIG. 35 illustrates another alternative guiding device 440 comprising a template wire 442 for guiding the application of a box pattern of ablation along a template portion 444 thereof. A temporary tissue anchoring portion 446 is provided in a coiled configuration for insertion into a frictional retention within a pulmonary vein opening generally as discussed herein.

Figure 36:
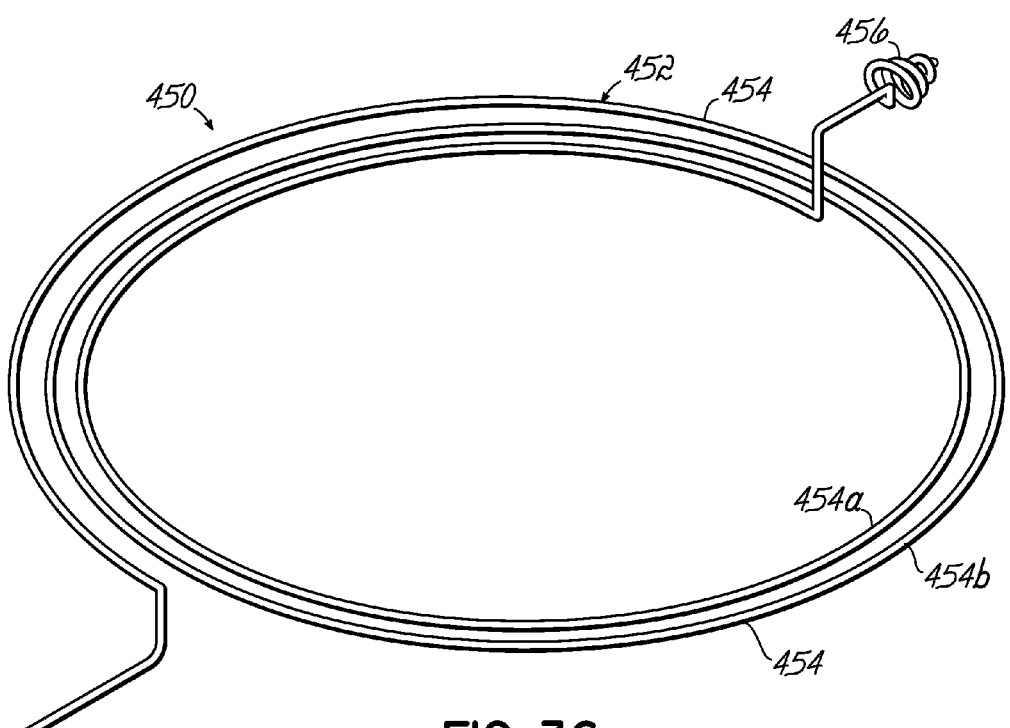
FIG. 36 is a perspective view illustrating another alternative template wire.

FIG. 36 illustrates another alternative guiding device 450 in the form of a template wire 452 having one or more double wire track sections 454 for receiving the ablating tip portion of an ablation catheter between wire portions 454a, 454b in guiding that tip portion around, for example, a box pattern in the interior wall surface of the left atrium. The guiding device 450 includes a temporary tissue anchoring portion 456, again in the form of a coil designed to be temporarily retained through friction when inserted in a pulmonary vein opening.

Figure 37:
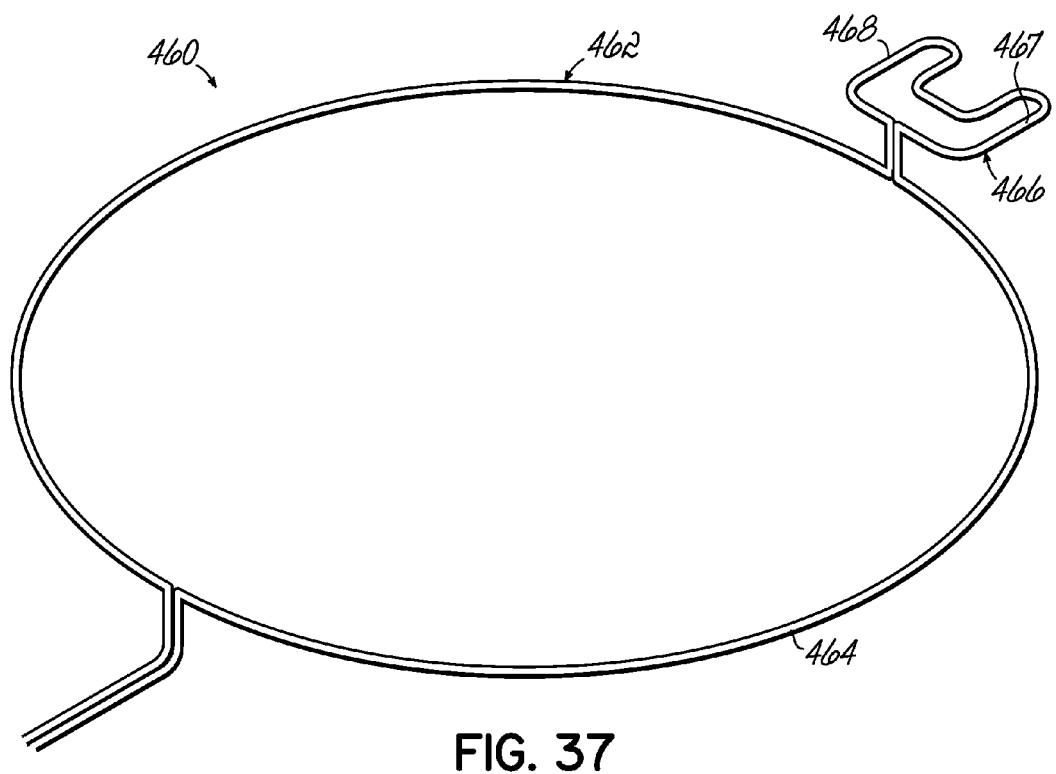
FIG. 37 is a perspective view illustrating another alternative template wire.
Figure 37A:
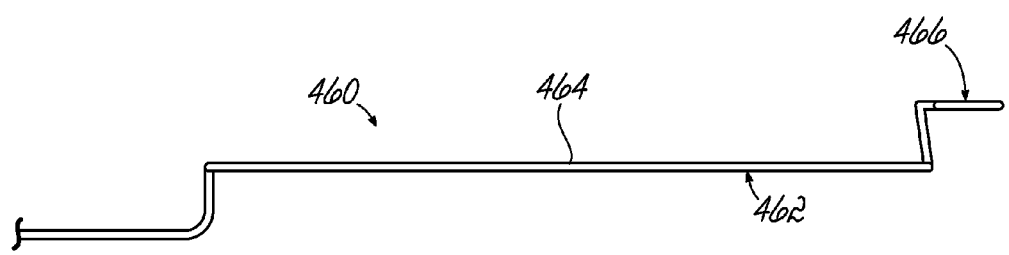
FIG. 37A is a side view of the template wire illustrated in FIG. 37.

FIGS. 37 and 37A illustrates another alternative embodiment of a guiding device 460 in the form of a template wire 462 having a template portion 464 adapted to engage with an ablation catheter as described herein and further including a temporary tissue anchoring portion 466 in the form of first and second generally U-shaped sections 467, 468 adapted to be inserted into one or more pulmonary vein openings to retain the device 460 in the left atrium for use as generally described herein.

Figure 38:
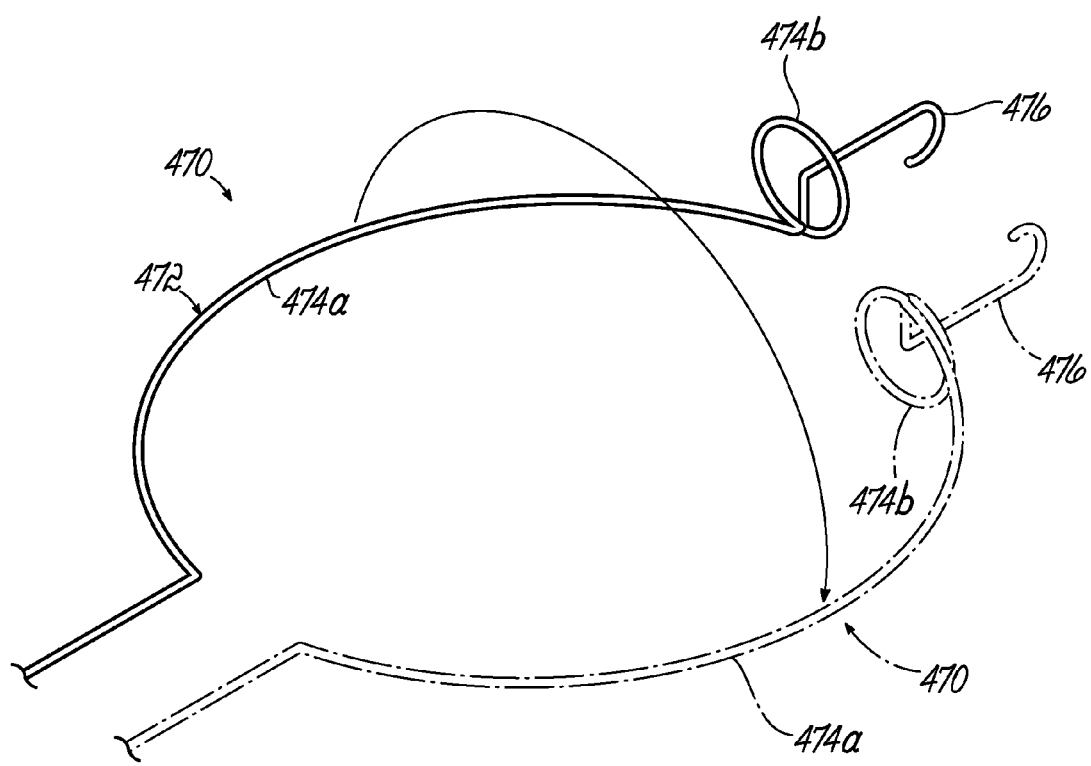
FIG. 38 is a perspective view of another alternative template wire.

FIG. 38 illustrates another alternative embodiment of a guiding device 470 comprising a template wire 472 formed with an arch segment 474a as part of the template portion, and a circular portion 474b as another part of the template portion for encircling a pulmonary vein opening. A temporary tissue anchoring portion 476 is provided in the form of a hook. The hook 476 may be inserted into a pulmonary vein opening and frictionally retained therein. In this embodiment, and as schematically illustrated, the wire device 470 may be rotated or re-oriented, such as shown, to apply multiple segments of an ablation pattern. That is, in the orientation shown in solid lines, the template portions 474a, 474b may be used in a first step to guide the application of a first pattern of ablation, generally as described herein, and then may be rotated or flipped to the second orientation (shown in dash-dot lines) to guide the application of a second pattern of ablation in a similar manner. The first and second patterns of ablation may form segments of a single closed geometric shape or may be used in any other manner. When re-orienting the device 470, the hook 476 may be inserted in different pulmonary vein openings.

Figure 39A:
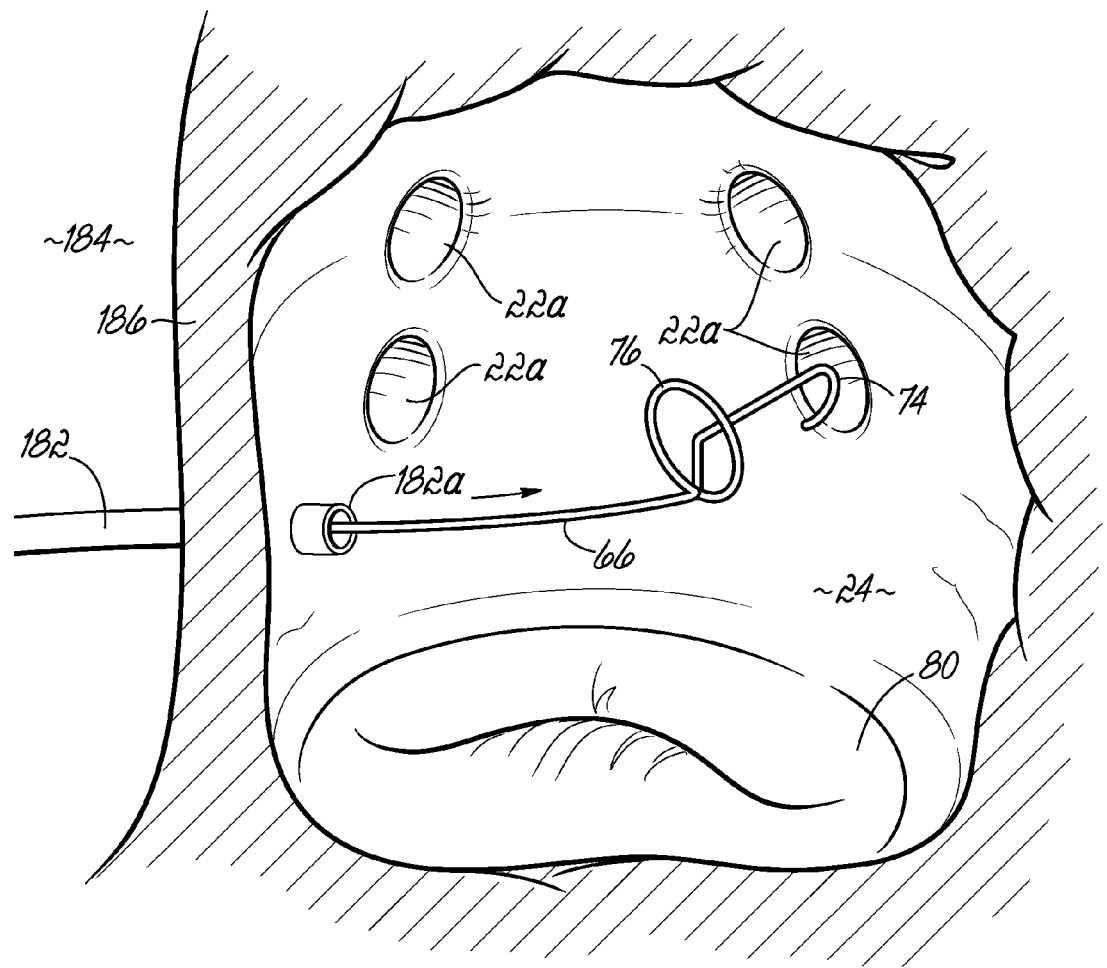
FIGS. 39A-39F are schematic perspective views illustrating another alternative template wire and system, and steps performed during the use of this system.
Figure 39B:
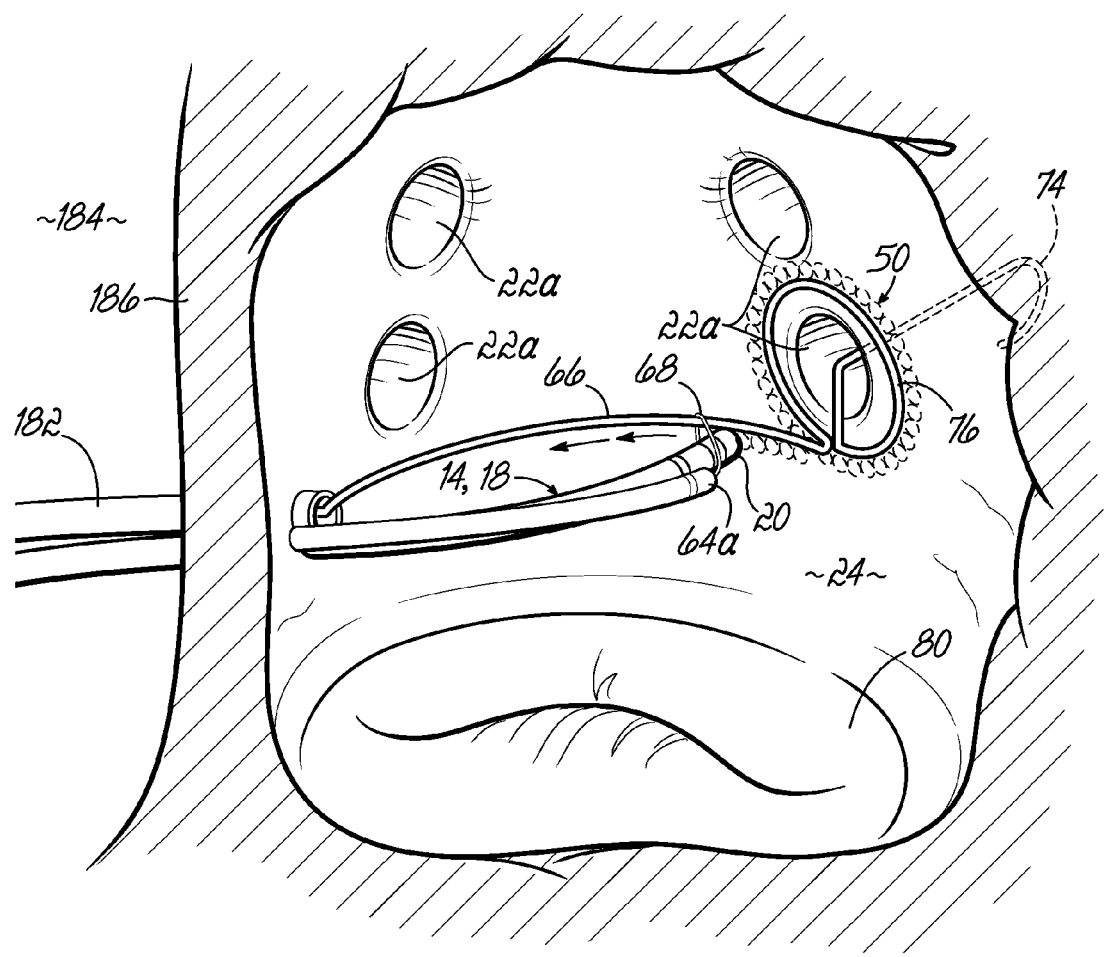
Figure 39C:
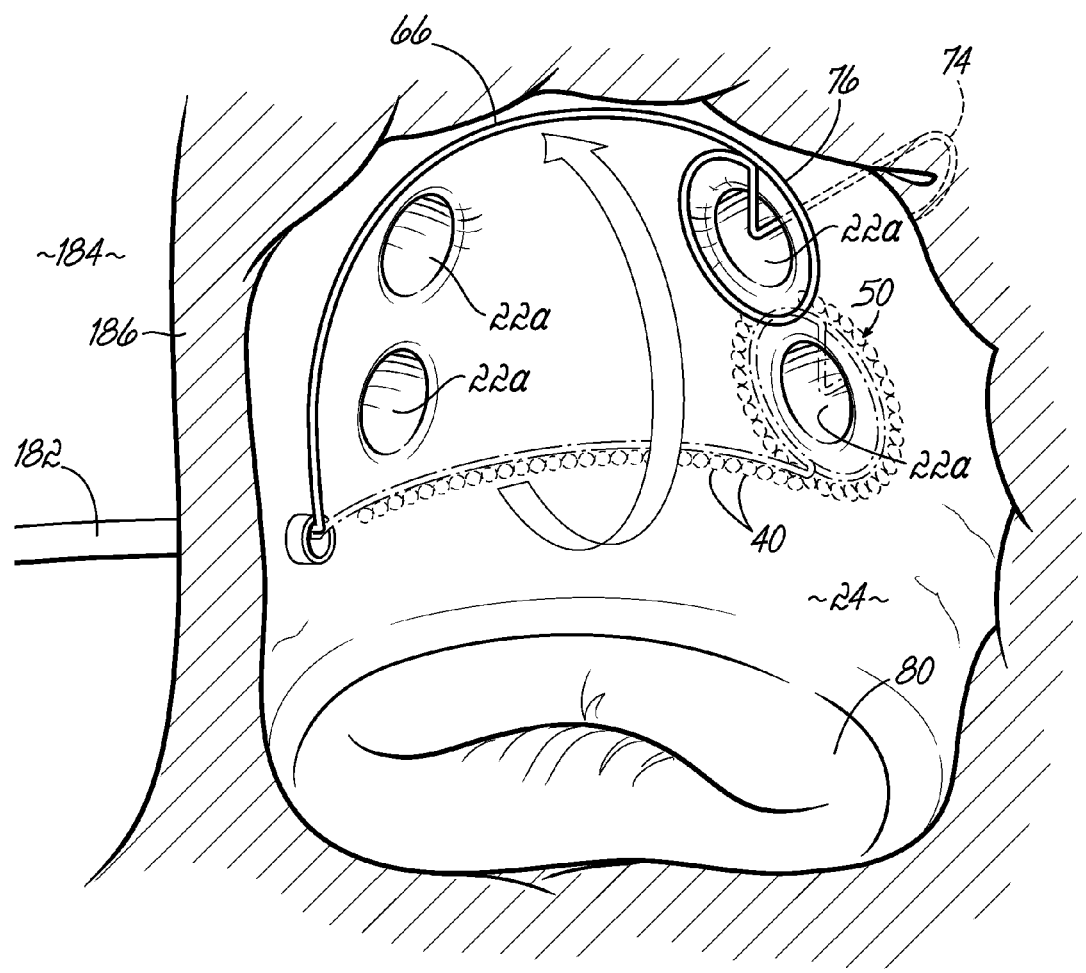
Figure 39D:
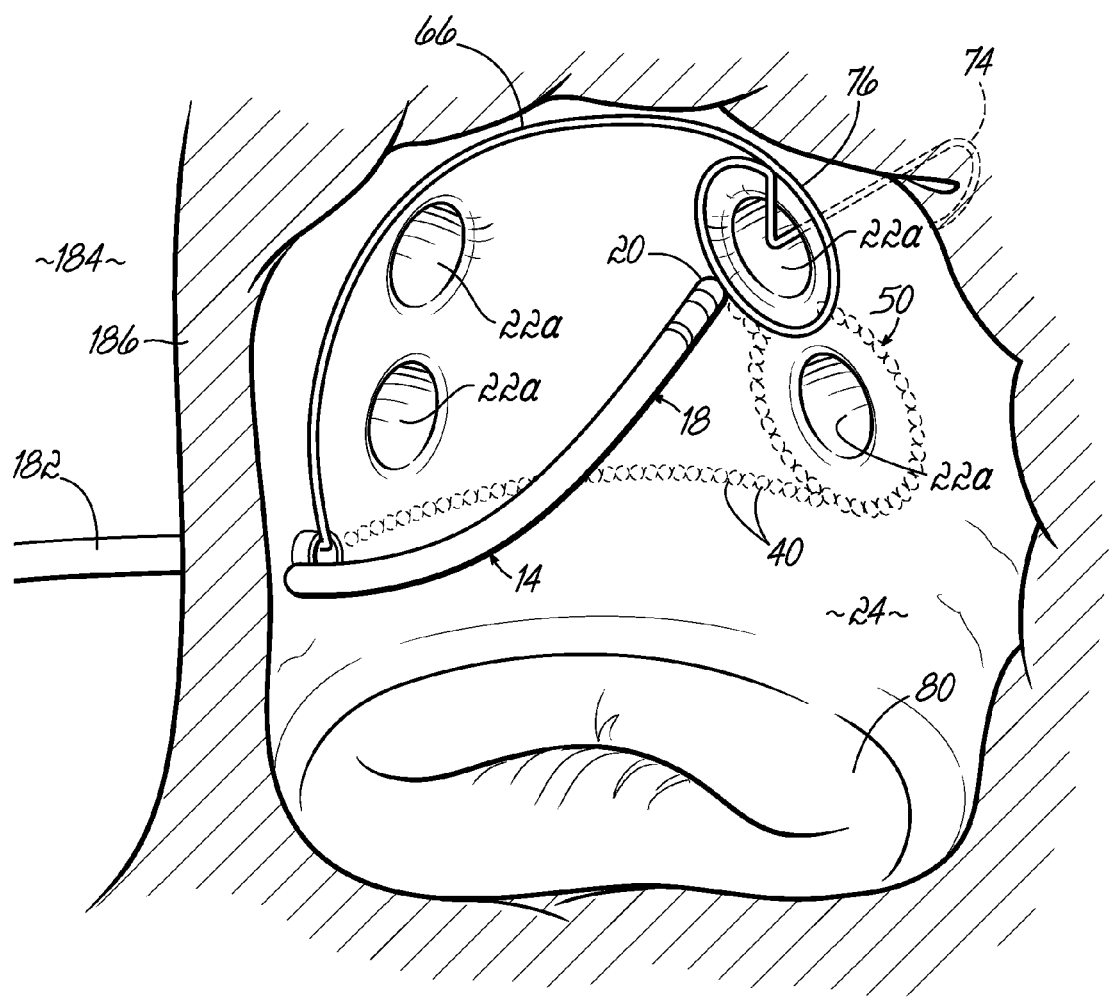
Figure 39E:
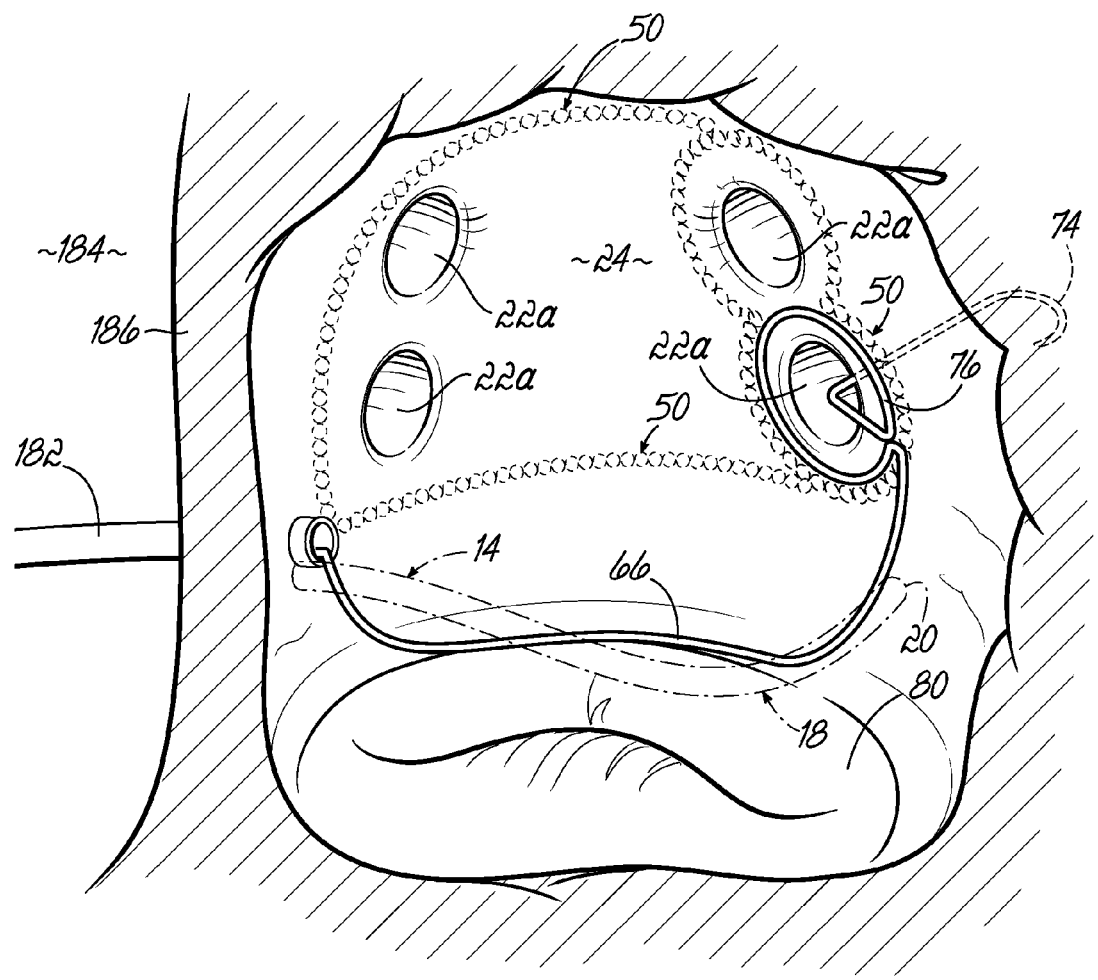
Figure 39F:
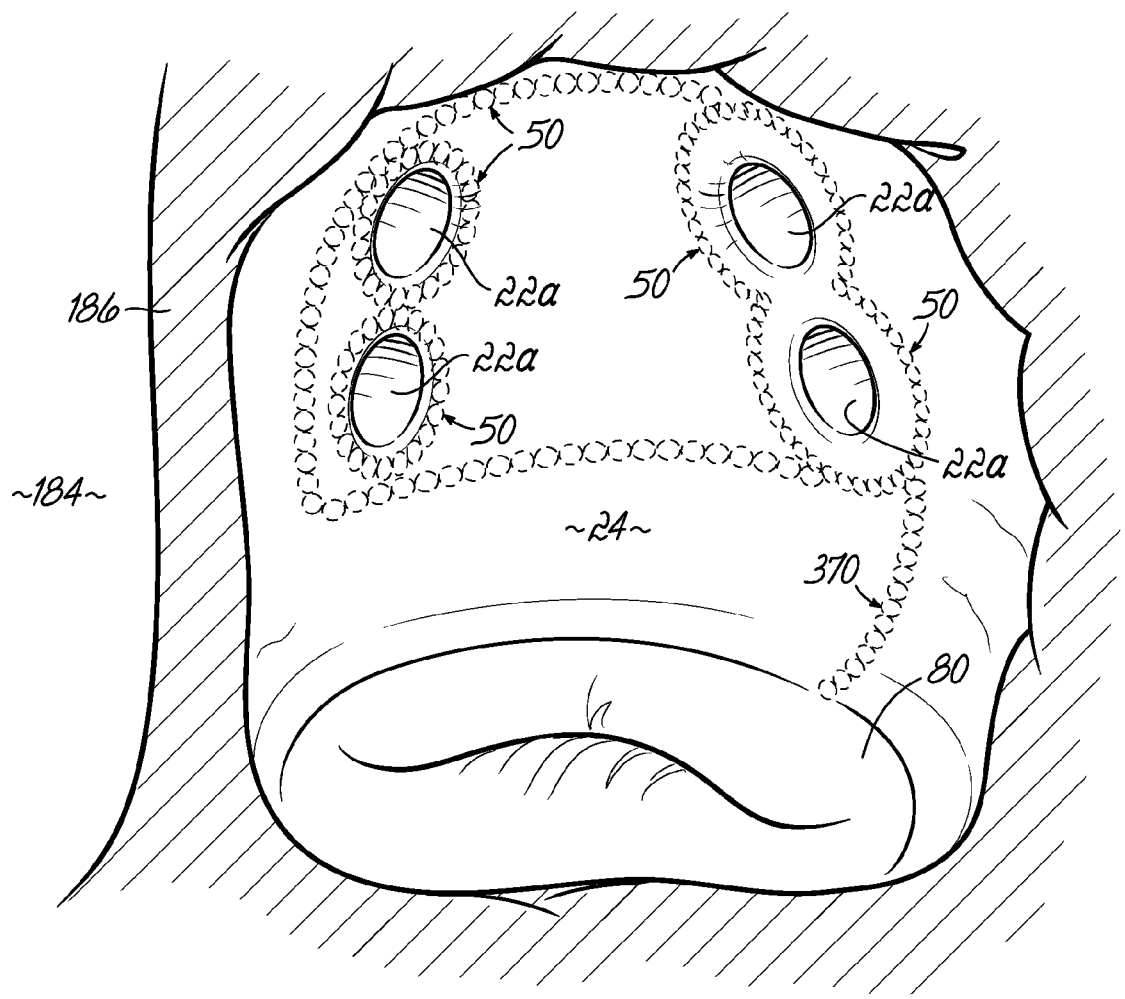

FIGS. 39A-39F illustrate another method for creating patterns of ablation in the left atrial chamber 24 designed to treat AF. In this embodiment, as illustrated in FIG. 39A, a wire template 66 is introduced through a delivery sheath 182 into the left atrial chamber 24 and a temporary anchoring portion 74 is inserted and retained within one of the pulmonary vein openings 22a. The template portion 76 and a more proximal straight portion of the wire 66 are used generally in a manner described herein to guide an ablation catheter 14 (FIG. 39B) and a positioning catheter 64 while creating a pattern 50 of lesions 40 as shown in FIG. 39B. FIG. 39C illustrates that the template wire 66 is rotated or flipped to a second position which is then used to guide the ablating tip portion 20 engaged thereagainst to apply further segments in the pattern 50 of ablation. That is, as shown in FIG. 39D and more fully in FIG. 39E, the pattern 50 of ablation may include isolating an additional pulmonary vein opening 22a and creating a further pattern 50 of ablation and resulting lesions 40 connecting between the two isolated pulmonary vein openings 22a and extending around the remaining two pulmonary vein openings 22a as shown in FIG. 39E. As also shown in FIG. 39E, a segment of the wire 66 proximal to the template portion 76 may then be further oriented to take on a shape that extends between the box pattern 50 and the mitral valve 80. This segment of the wire 66 may then be used to guide the ablating tip portion 20 of the ablation catheter 14, shown in dash-dot lines, to create a line segment or pattern 370 of ablation generally between the box pattern 50 and the mitral valve 80 as shown in FIG. 39F.

Figure 40A:
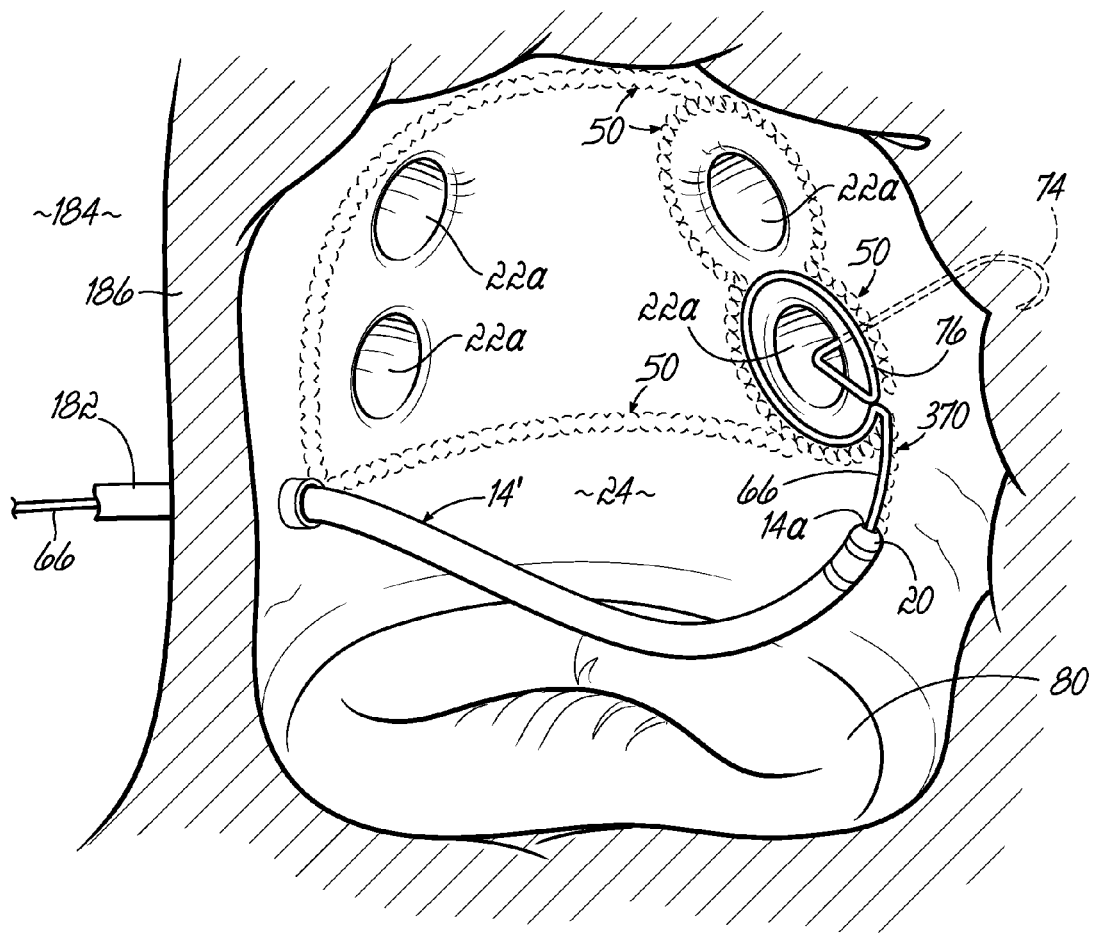
FIG. 40A is a schematic, perspective view illustrating another system useful with the system, for example, illustrated in FIGS. 39A-39F to apply a pattern of ablation to the mitral valve.
Figure 40B:
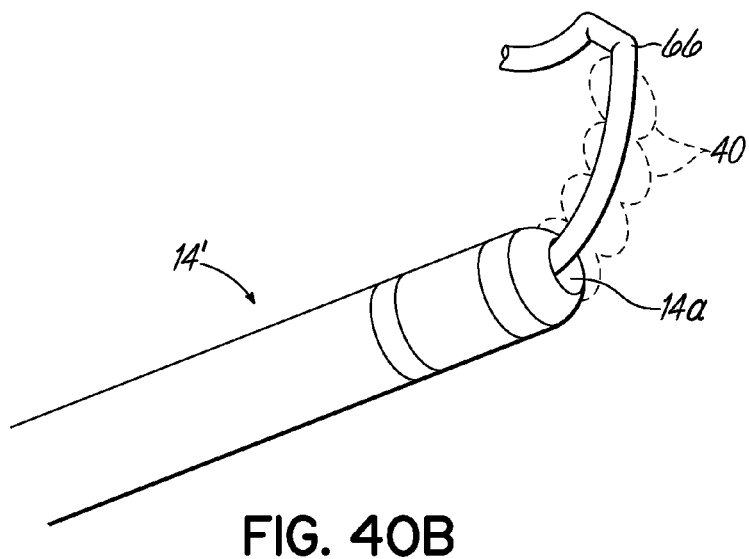
FIG. 40B is an enlarged view of the distal tip of the ablation catheter and template wire illustrated in FIG. 40A.

FIGS. 40A and 40B illustrate another alternative for creating the segment or pattern 370 of lesions between the box pattern 50 and the mitral valve 80. In this embodiment, the ablation catheter 14' includes a lengthwise lumen 14a that receives the template wire 66 and the ablation catheter 14' may be moved along the template wire 66 in either of two opposite directions to guide the ablating portion 20 as the ablation catheter 14' is actuated to apply the segment or pattern 370 of ablation and resulting lesions 40 between the box pattern 50 and the mitral valve 80.

Figure 40C:
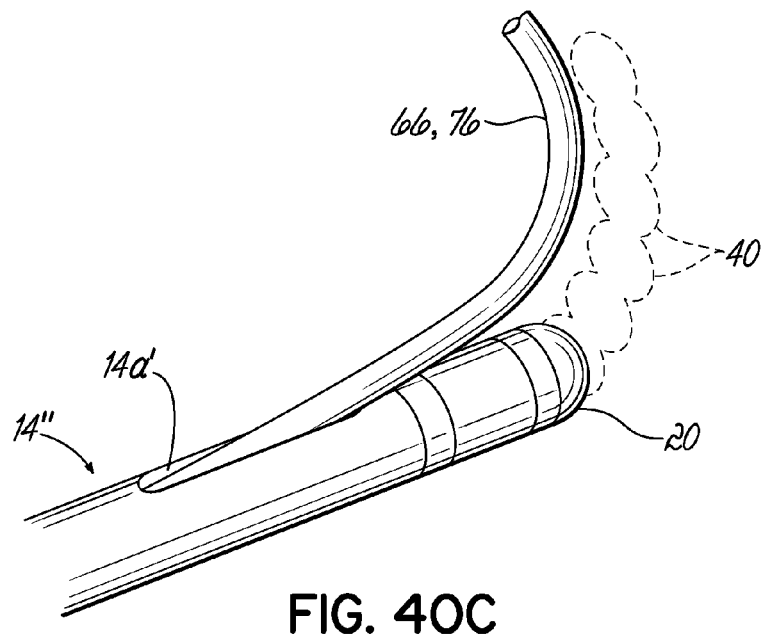
FIG. 40C is an enlarged view similar to FIG. 40B, but illustrating another alternative construction of the system.
Figure 40D:
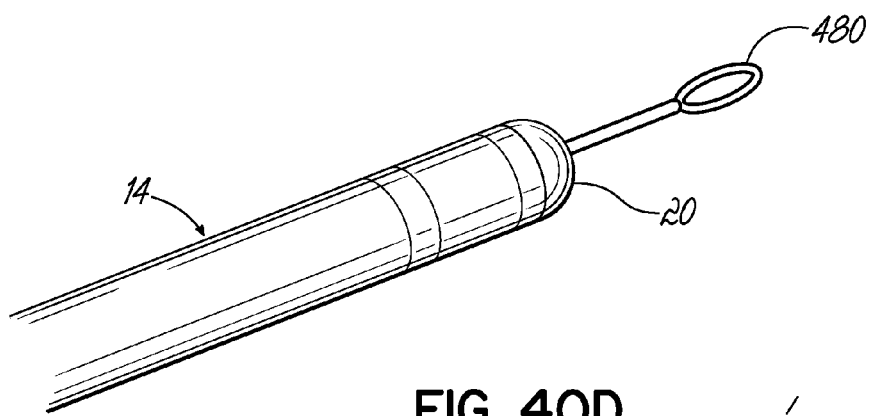
FIGS. 40D and 40E are enlarged views similar to FIG. 40C, but illustrating another alternative ablation catheter.
Figure 40E:
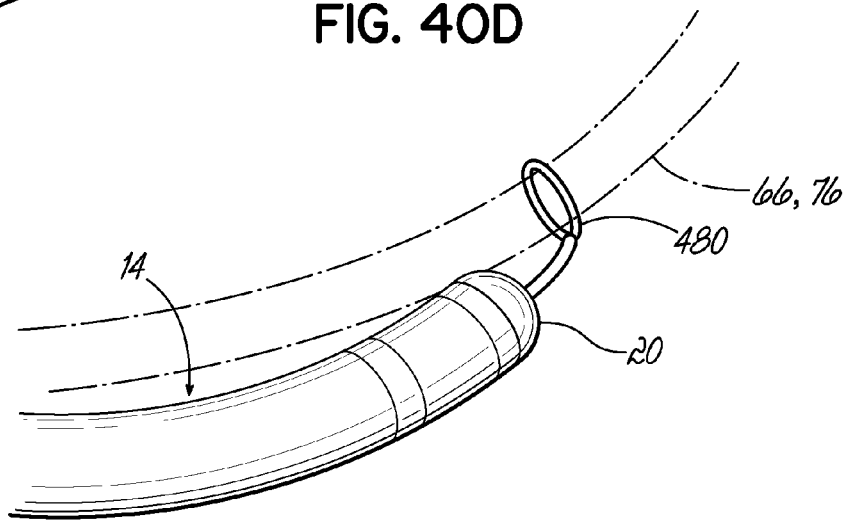
Figure 40F:
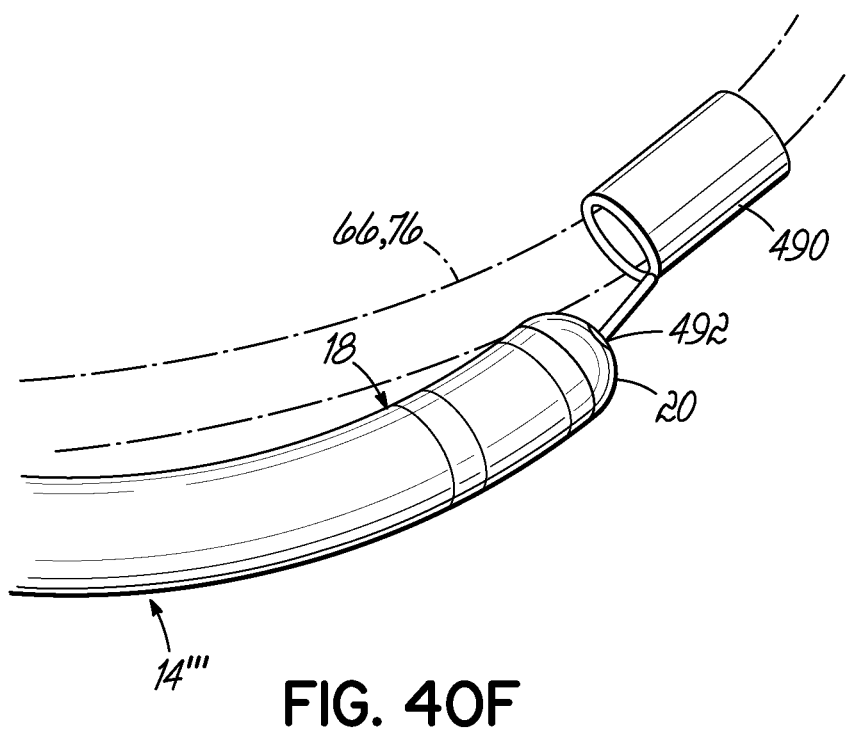
FIG. 40F is an enlarged view similar to FIG. 40C, but illustrating another alternative ablation catheter, and connection between the ablation catheter and the template wire.
Figure 40G:
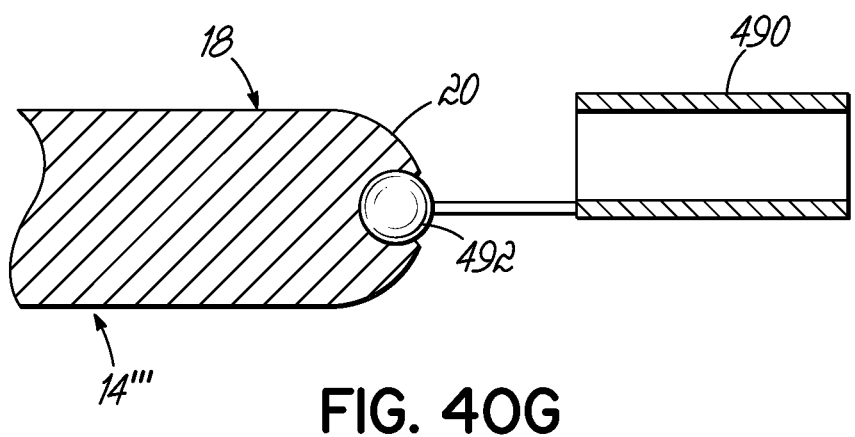
FIG. 40G is a cross sectional view of the ablating tip portion of the catheter shown in FIG. 40F.

FIGS. 40C-40G illustrate additional alternatives for coupling and guiding the ablating tip portion along the template wire 66. FIG. 40C illustrates an embodiment in which a lengthwise extending lumen 14a' in the ablation catheter 14" opens on a side surface of the ablation catheter 14" as opposed to the distal tip thereof. FIG. 40D illustrates a loop-type connector 480 through which the template wire 66, 76 may extend and slide similar to embodiments previously discussed and as further shown in FIG. 40E. The ablation catheter 14'" of FIG. 40F includes a tubular type channel connector 490 for receiving the template wire 66, 76 and, as shown in FIG. 40G, including a pivotal connection 492 with the ablation catheter 14'" to assist with manipulation and movement during the ablation and lesion forming process.

Figure 41A:
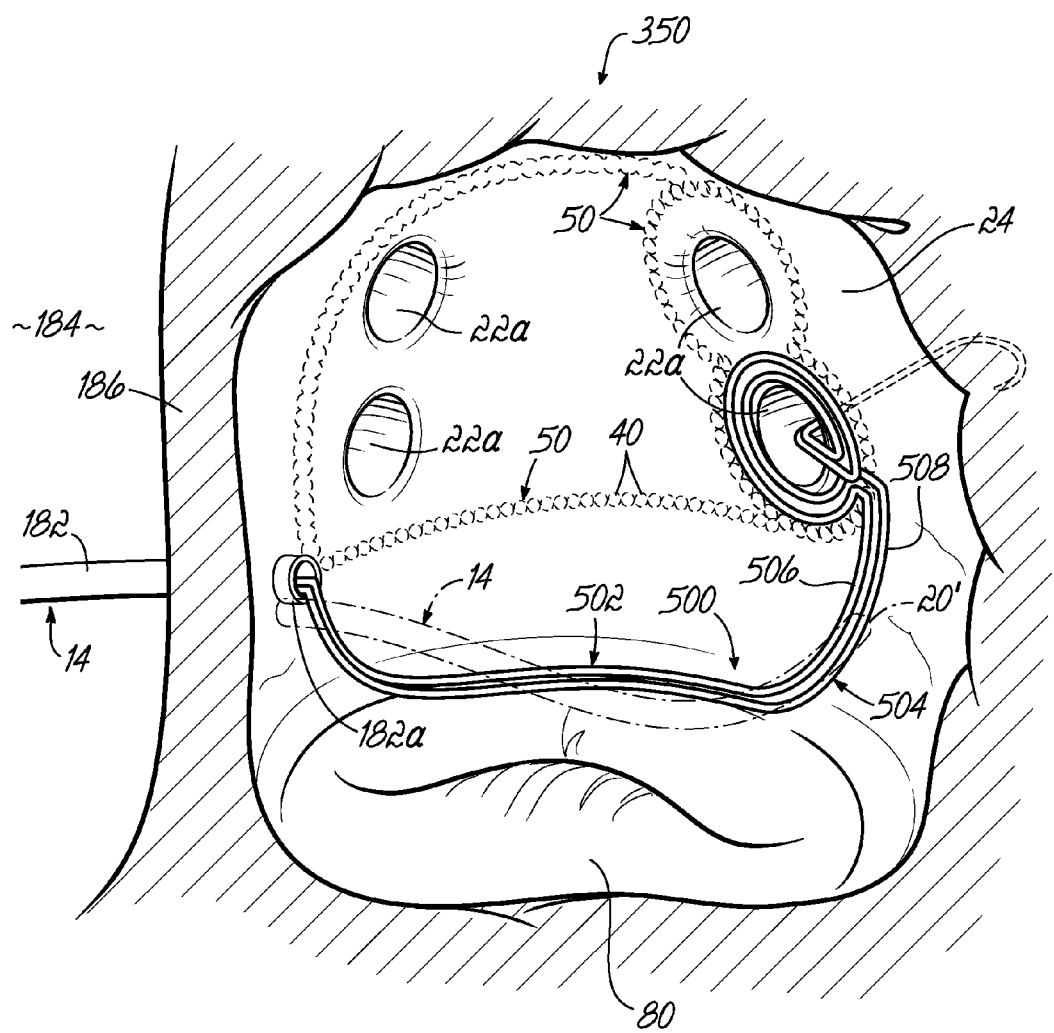
FIGS. 41A and 41B are respective schematic, perspective views illustrating another alternative template wire and ablation catheter used in the left atrium.
Figure 41B:
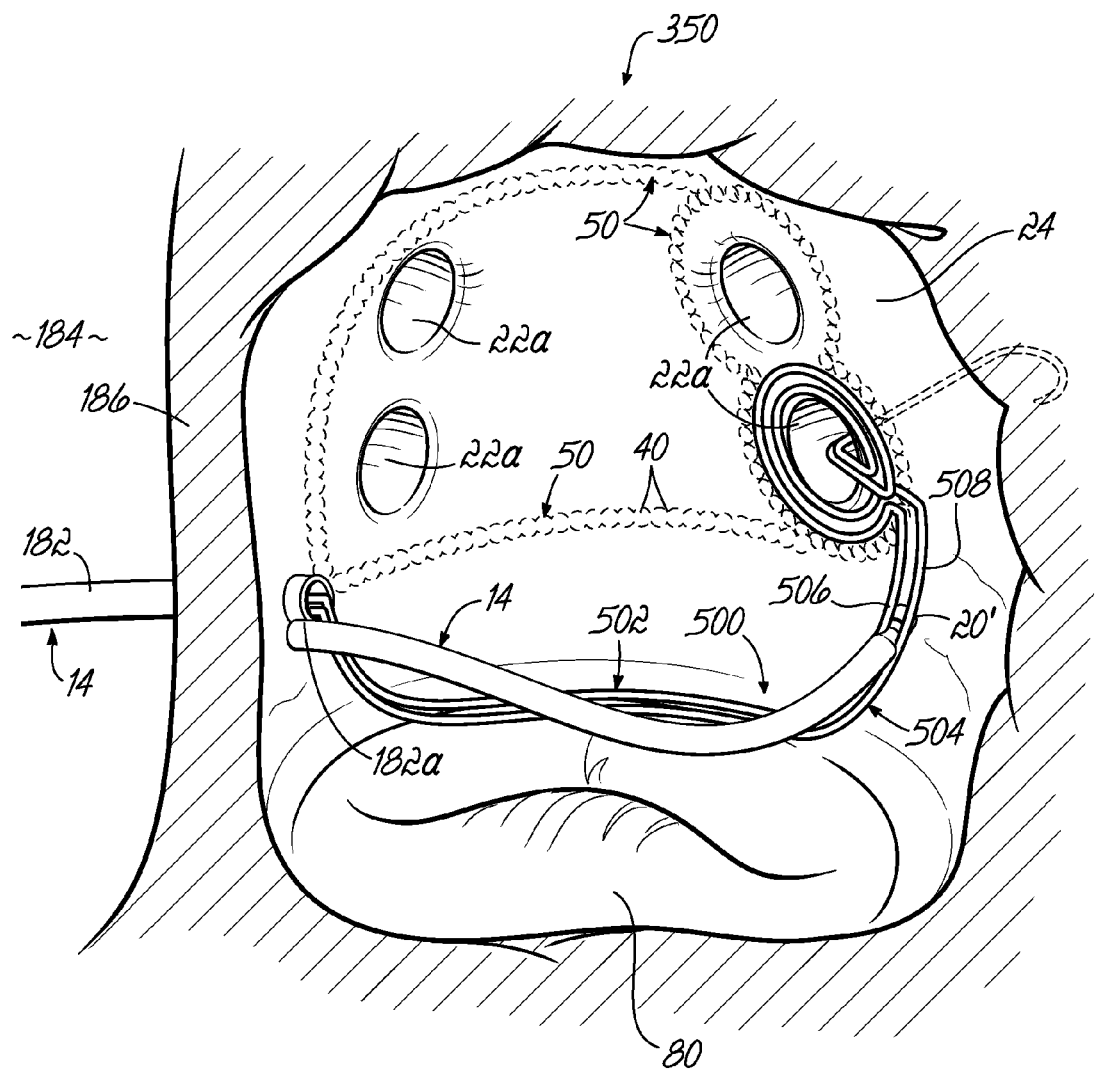
Figure 41C:
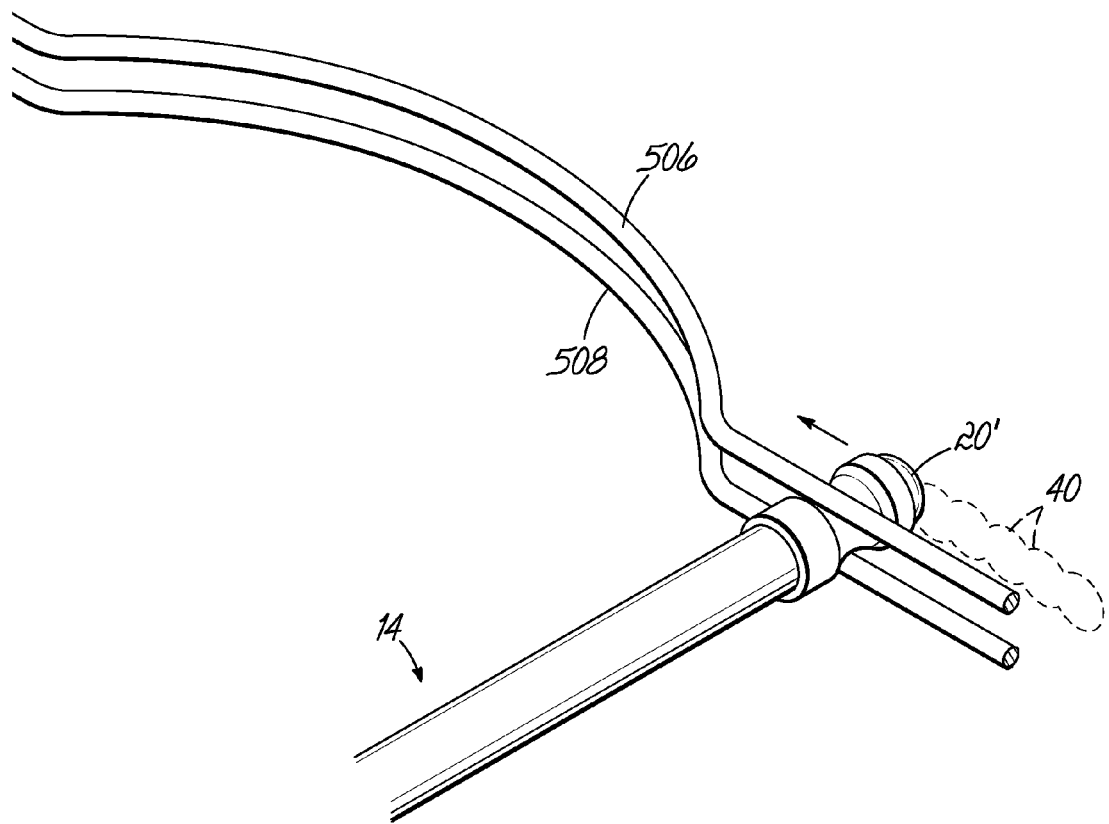
FIG. 41C is an enlarged view illustrating the connection formed between the ablation catheter and the template wire illustrated in FIGS. 41A and 41B.

FIG. 41A illustrates another alternative embodiment for a guiding device 500 comprising a template wire 502 similar to that shown in FIG. 39E, but including a double wire track section 504. The double wire track section 504 includes two wire portions 506, 508 between which the ablating tip portion 20' of the ablation catheter 14 can ride as illustrated in FIGS. 41B and 41C, to facilitate better control and guidance while forming lesions 40. For better sliding retention, the ablating tip portion 20' is configured with a recess to be physically coupled with the wire portions 506, 508 for sliding movement therealong.

Figure 42:
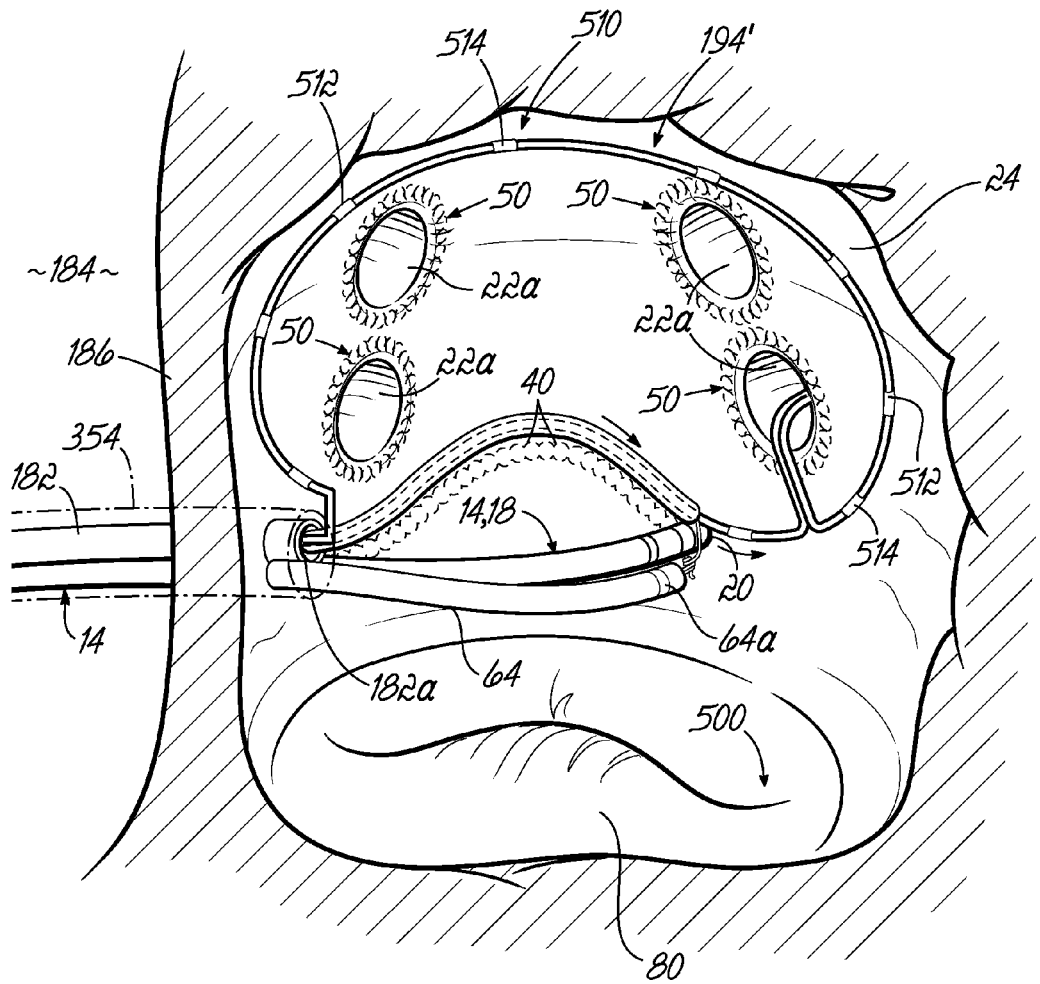
FIG. 42 is a schematic, perspective view illustrating a system used in the left atrium, and constructed in accordance with another embodiment.

FIG. 42 illustrates another alternative embodiment of a system 510 including a guiding device in the form of a template wire 194' similar to that shown in FIG. 30A but having a plurality of sensors 512 and markers 514. The sensors 512 may be sensing electrodes and the markers 514 may be radiopaque markers that are identifiable under X-ray. The sensing electrodes 512 would be usable for mapping of an EKG signal. After ablation it may be useful to confirm that an EKG signal does not continue across the pattern 50. The radiopaque markers 514 would be useful for purposes of identifying the location of the ablation catheter and/or wire 194', for example, under X-ray as the electrophysiologist is conducting the procedure. This system 510 further shows the use of a third catheter device receiving and riding along the wire 194' to assist with guiding the ablating tip portion 20. This catheter device can also be directly or indirectly secured to the ablating tip portion 20.

Figure 43:
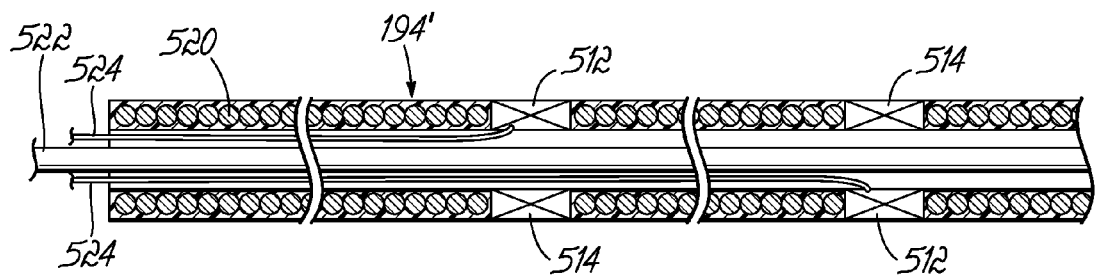
FIG. 43 is a cross sectional view showing a portion of the template wire illustrated in FIG. 42.

FIG. 43 is a cross sectional view of a portion of the template wire 194' shown in FIG. 42 and illustrating a composite construction for the wire 194' including an outer coil 520 with sensing electrodes 512 and radiopaque markers 514, and an inner core or guide 522. Signal wires 524 are coupled to each of the sensing electrodes 512 and used for transmitting electrical signals for mapping or detecting EKG signals.

Figure 44:
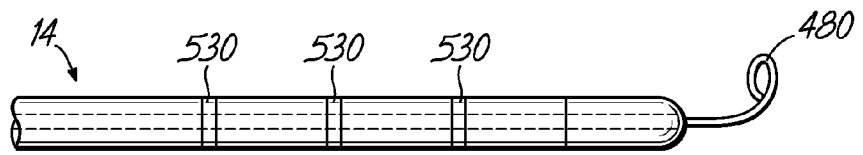
FIG. 44 is a plan view showing the distal tip of an ablation catheter constructed in accordance with another embodiment.
Figure 44A:
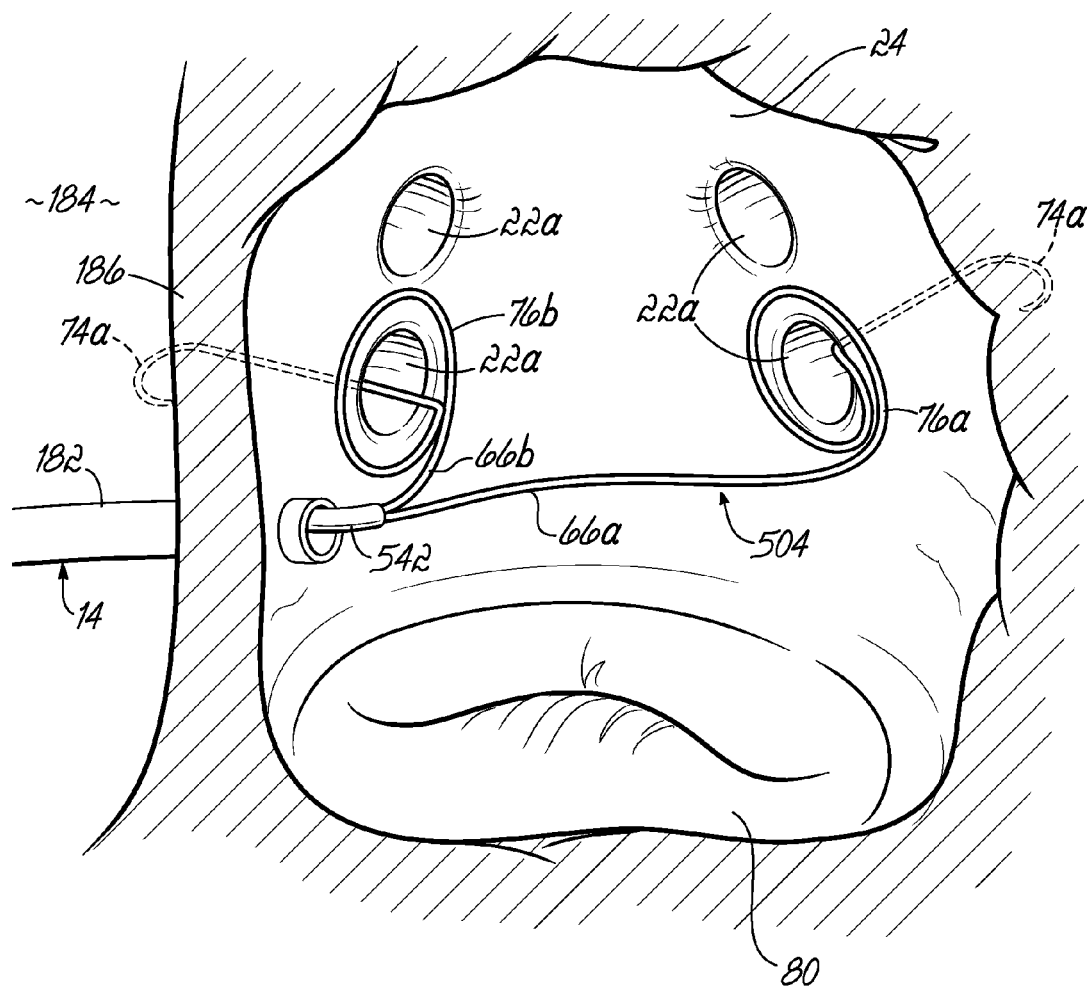
FIGS. 44A-44G are respective schematic, perspective views illustrating a system constructed in accordance with another embodiment used to apply a pattern of ablation within the left atrium.
Figure 44B:
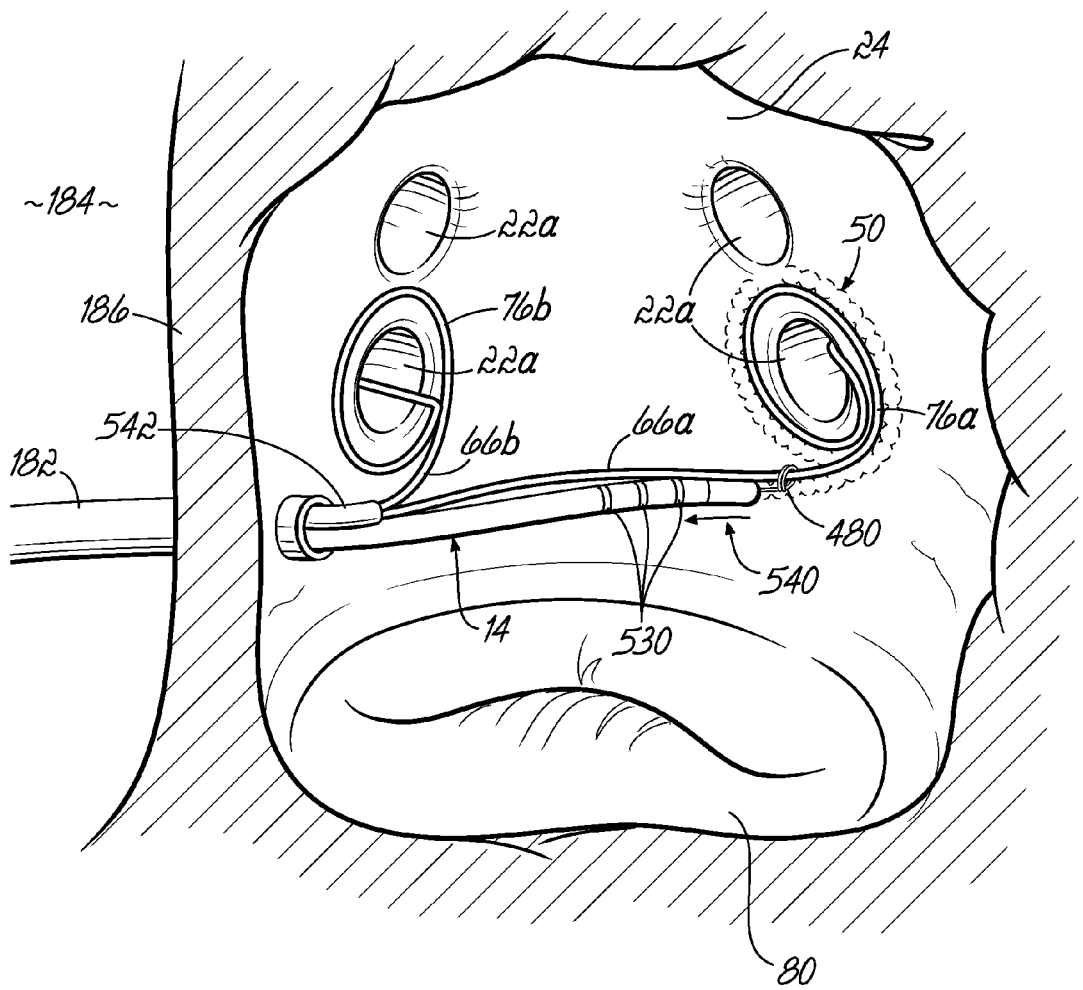

FIG. 44 illustrates an ablation catheter 14 having a tip with a loop connector 480 as previously discussed, and interrogation sensors 530, such as sensing electrodes, that may also or alternatively be used for detecting EKG signals for purposes of testing the effectiveness of the lesion pattern in blocking disruptive electrical signals through the tissue.

Figure 44C:
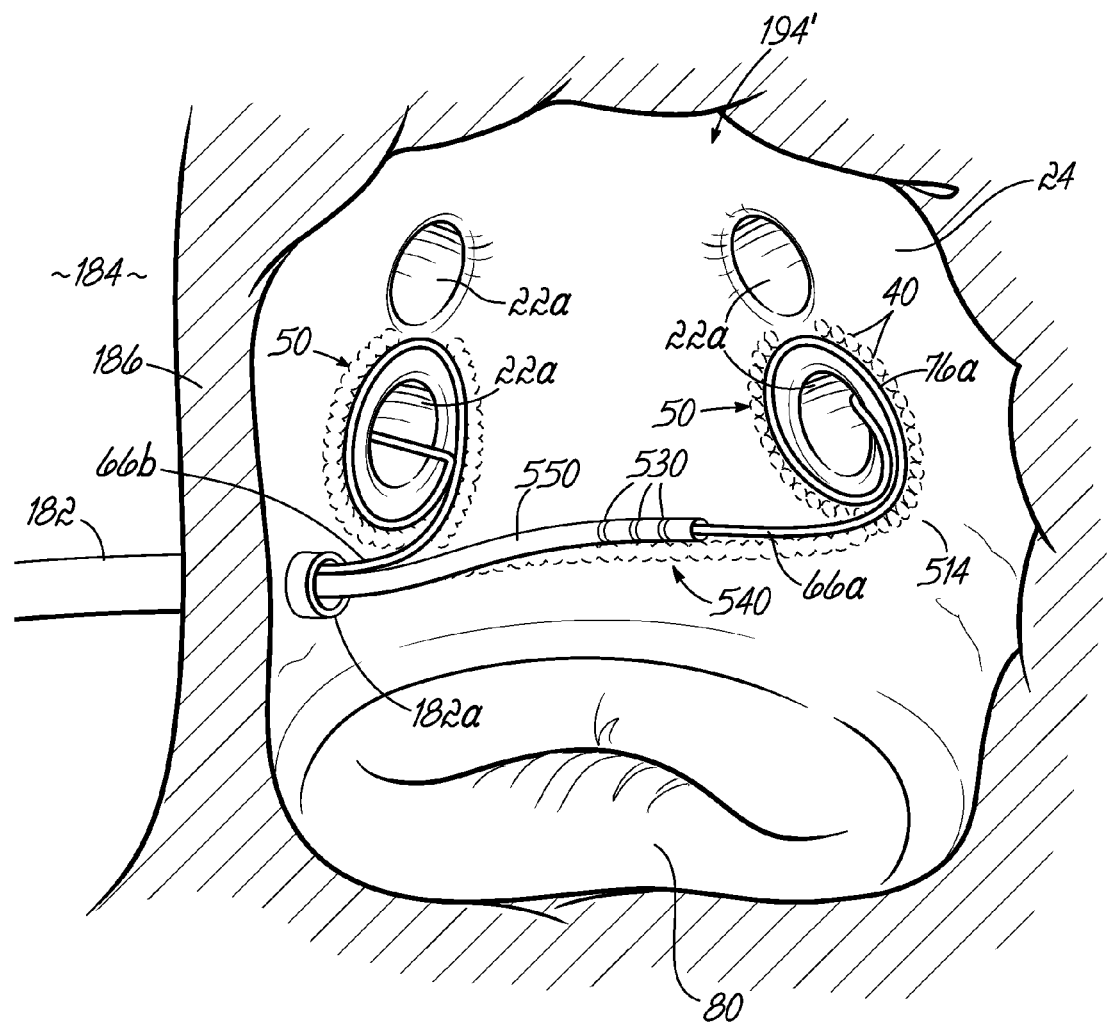
Figure 44D:
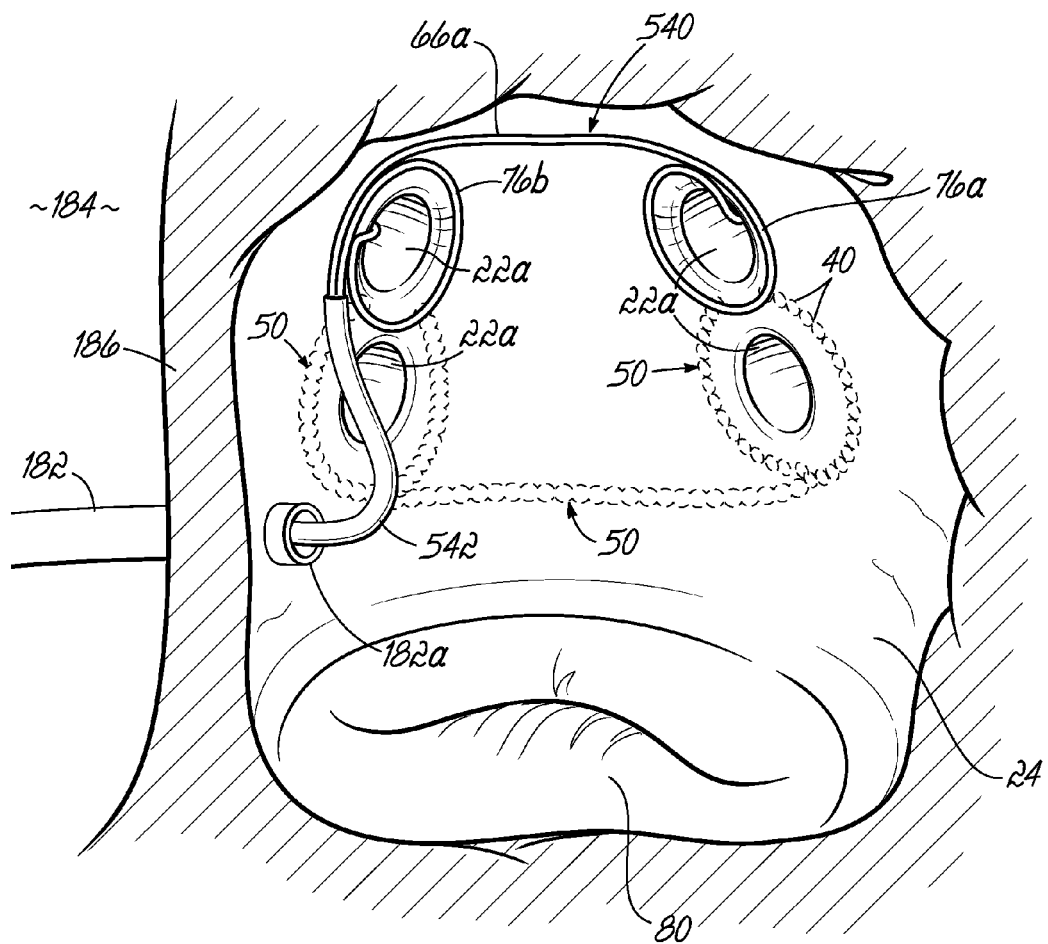
Figure 44E:
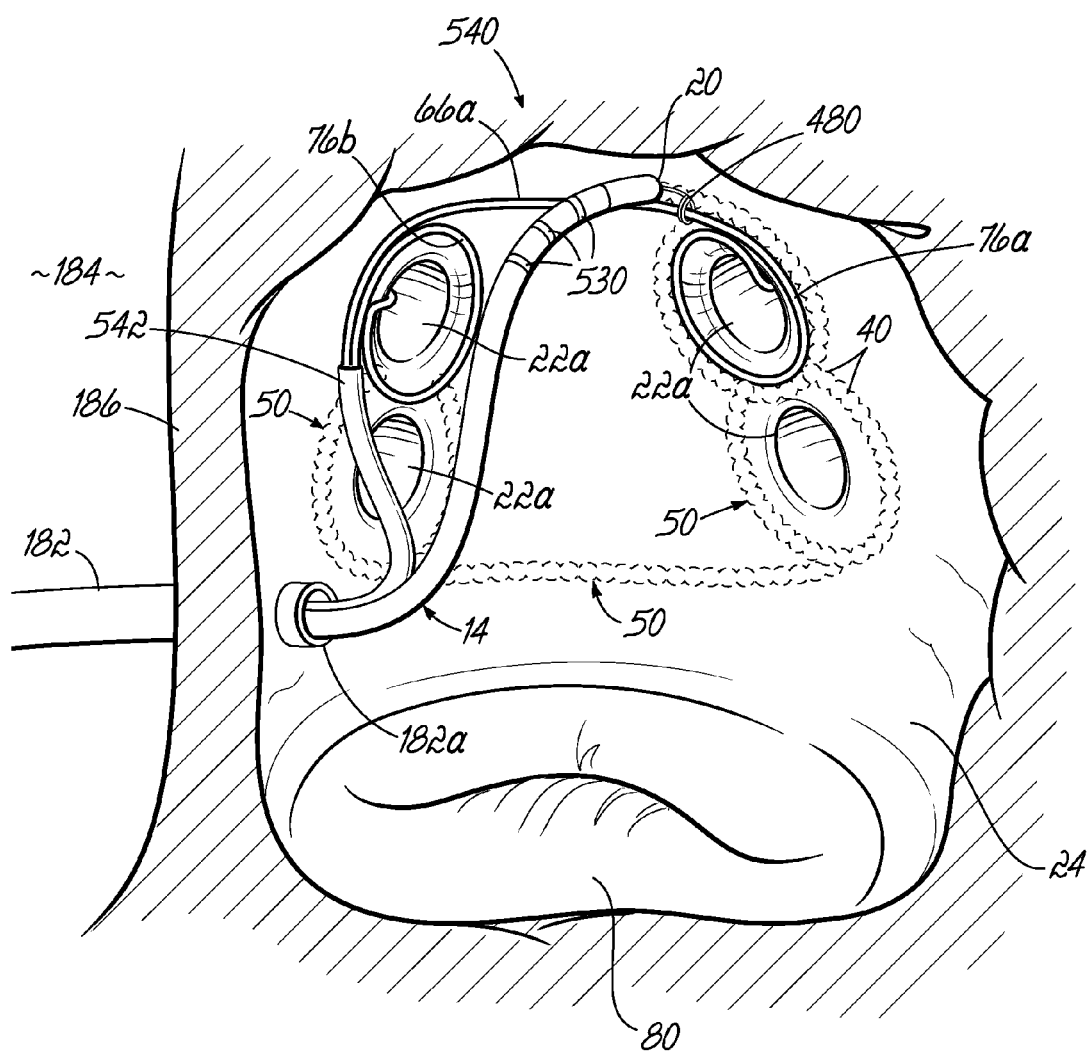
Figure 44F:
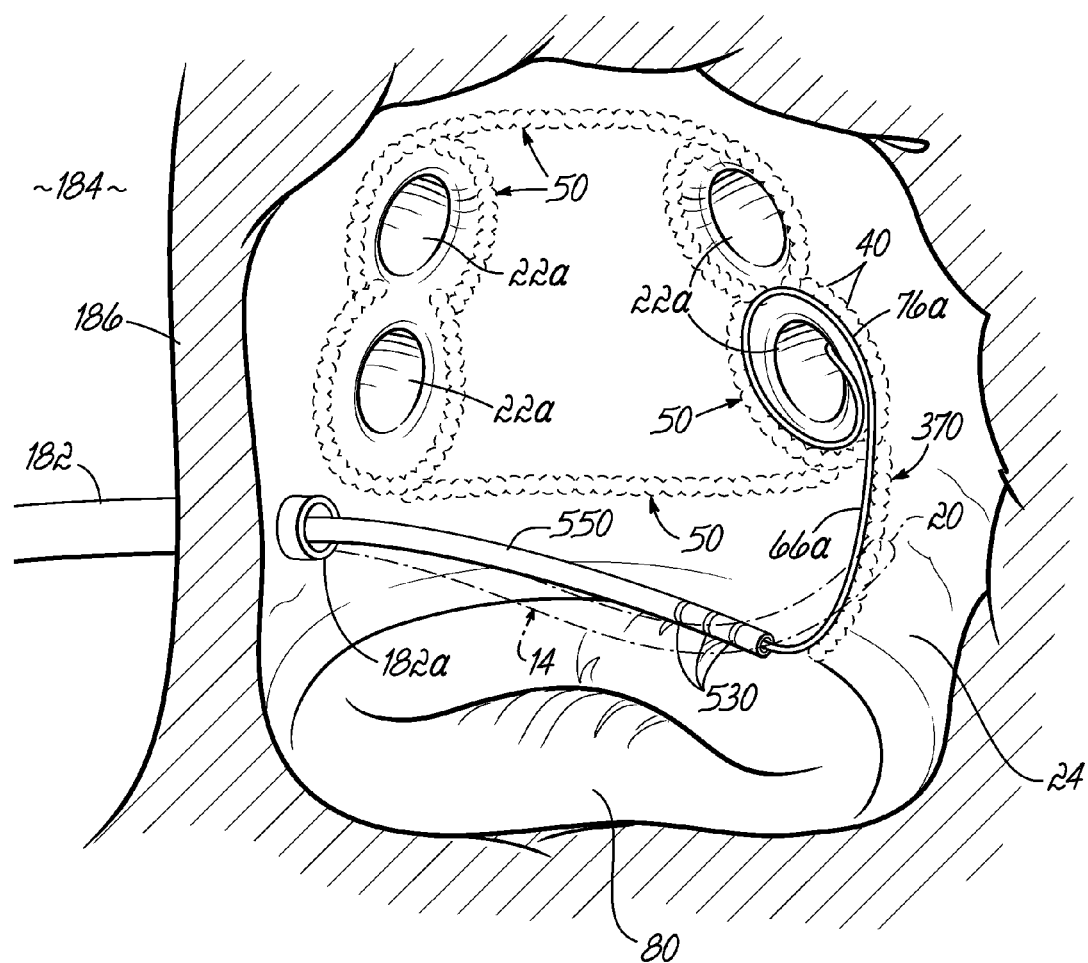
Figure 44G:
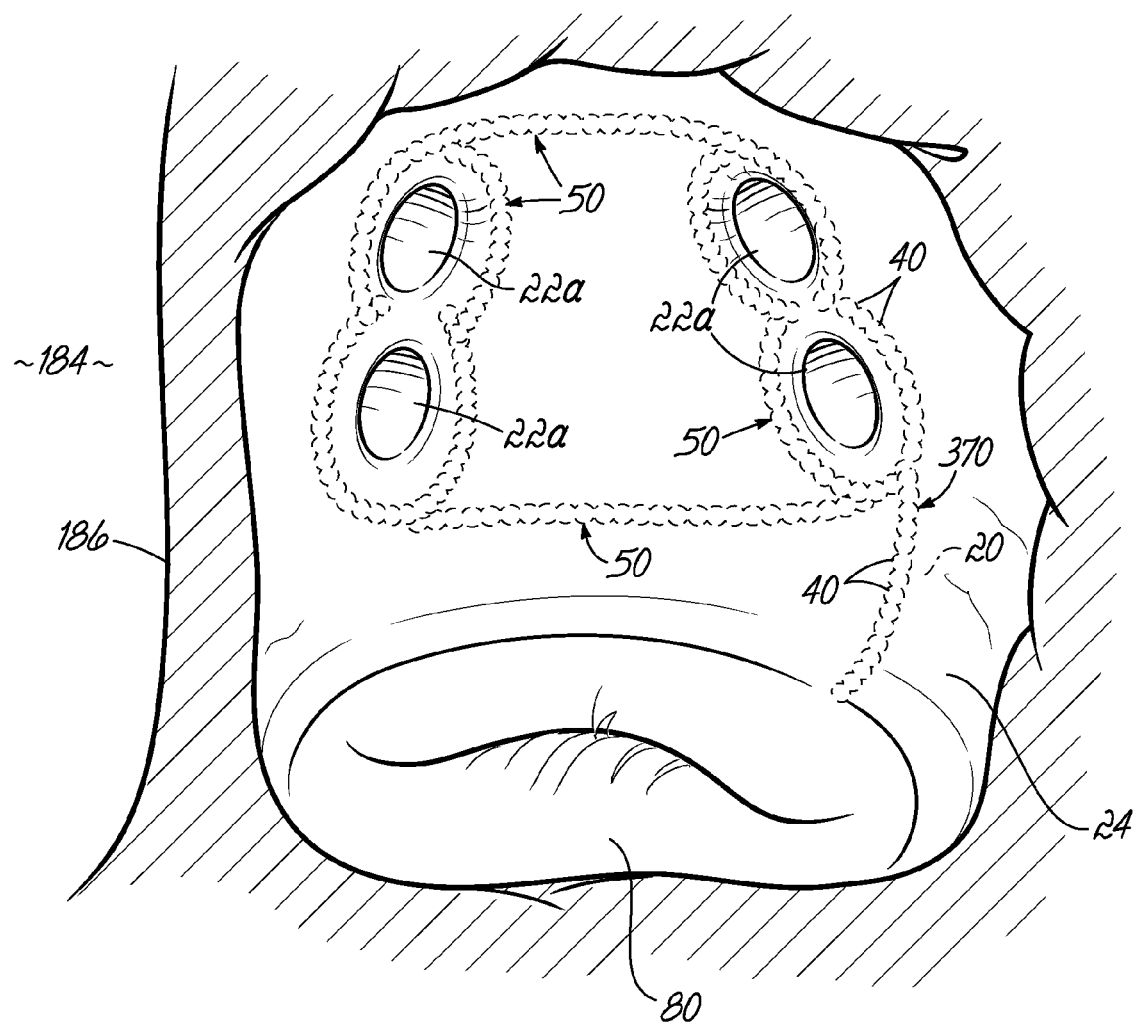

FIGS. 44A-44G illustrate another method using a system 540 comprising first and second template wires 66a, 66b. The first and second template wires 66a, 66b are introduced through a delivery sheath 182 into the left atrium 24 using another smaller diameter choker catheter 542 and are temporarily contained in first and second pulmonary vein openings 22a. The template wires 66a, 66b are used to guide an ablation catheter 14 in one of the manners described herein, such as in the manner shown in FIG. 44B. FIG. 44C illustrates that the ablation catheter 14 may be used for interrogating or testing the effectiveness of the ablation pattern by way of sensors 530. It will be appreciated that another interrogation catheter 550 (FIGS. 44C, 44F) may be guided along the wires 66a, 66b for this purpose in the alternative. As shown in Figs. The choker catheter 542 is positioned so as to provide stability for the two wires 66a, 66b. As illustrated in FIG. 44D the same two template wires 66a, 66b may be used to apply remaining portions of the ablation and resulting pattern 50 of lesions 40, that is for isolating the remaining two pulmonary vein openings 22a and applying the remaining portion of the box pattern 50 as illustrated in FIGS. 44E and 44F. As further illustrated in FIG. 44F, the catheter (such as interrogation catheter 550) carrying one of the template wires 66a may be manipulated toward the mitral valve 80 to extend a portion of the template wire 66a from the box pattern 50 to the mitral valve 80 for purposes of guiding the ablation catheter 14 to create a segment or pattern 370 of ablation and resulting lesions 40 between the box pattern and the mitral valve. The resulting overall pattern of lesions 40 is as shown in FIG. 44G.

Figure 45A:
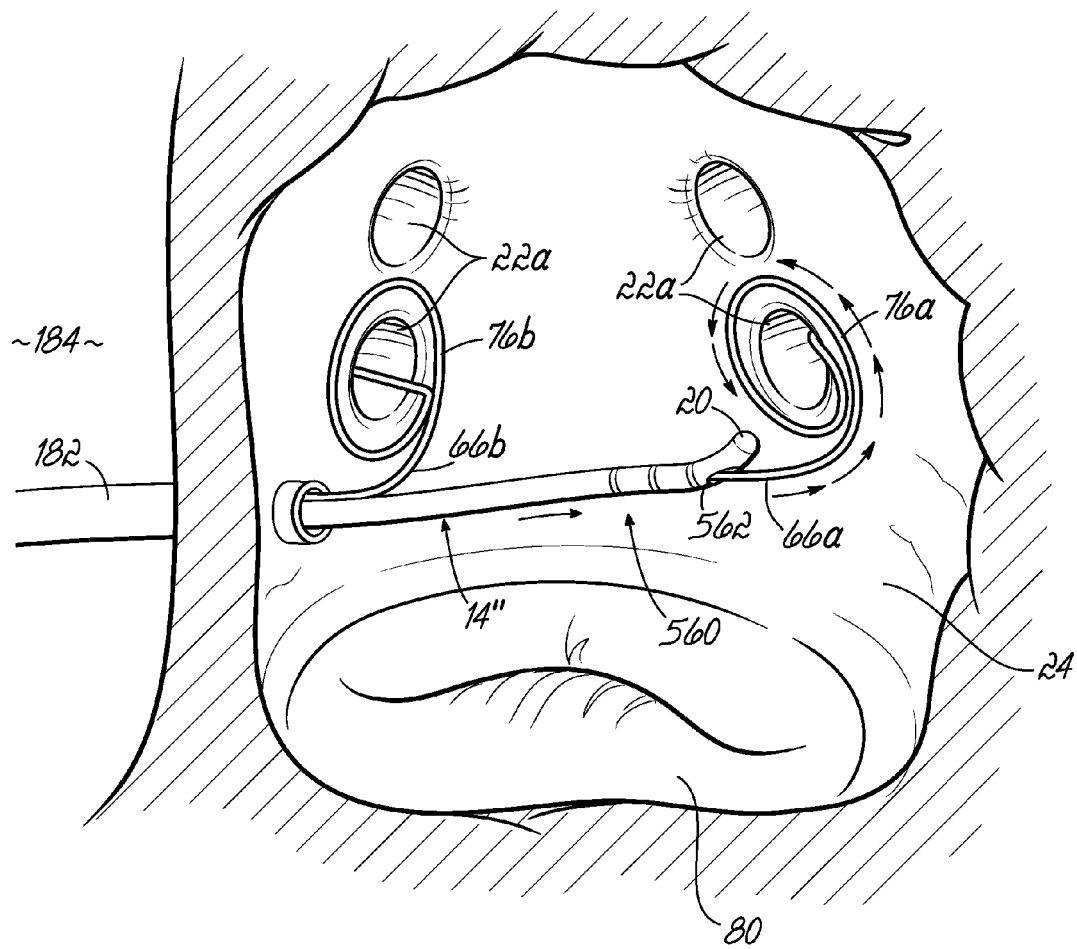
FIG. 45A is a schematic, perspective view illustrating a system constructed in accordance with another embodiment being used to apply a pattern of ablation in the left atrium.
Figure 45B:
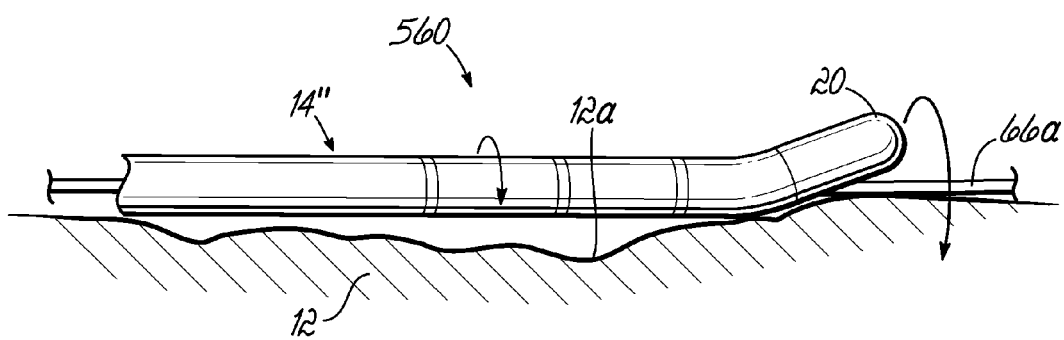
FIG. 45B is an enlarged view of the system shown in FIG. 45A and its use in ablating tissue.
Figure 45C:
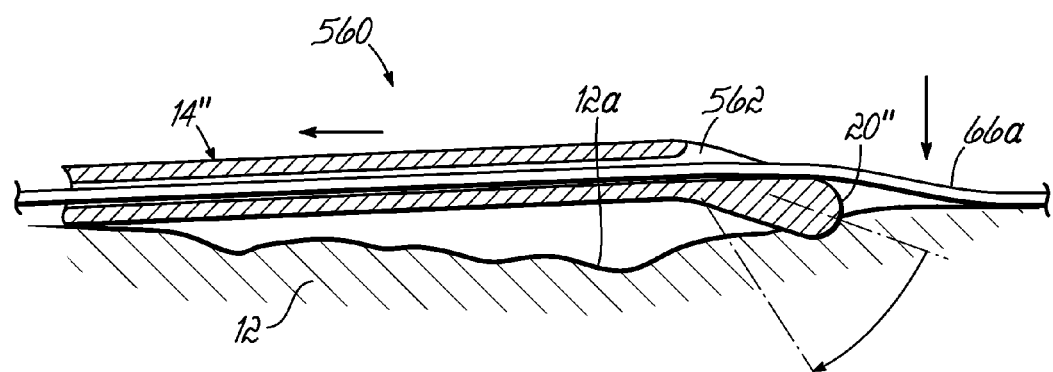
FIGS. 45C and 45D are views similar to FIG. 45B, but illustrating the distal tip portion of the ablation catheter in cross section and transverse or angled and biased movement of the ablating tip portion.
Figure 45D:
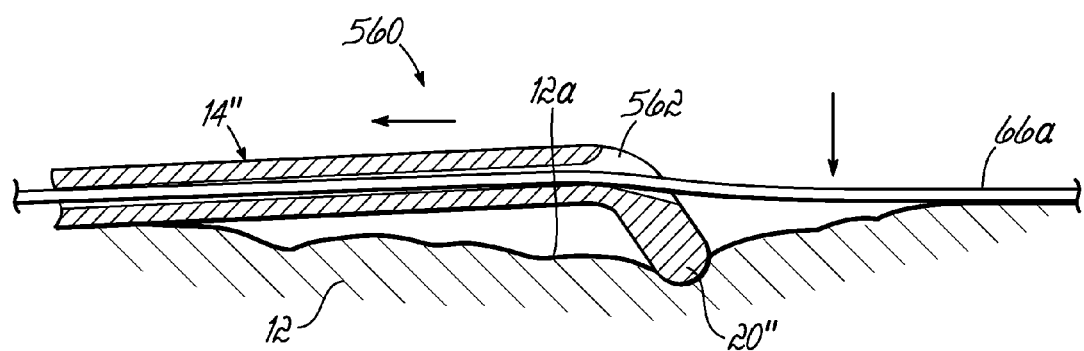

FIGS. 45A-45D illustrate another embodiment of a system 560 including an ablation catheter 14" and template wire 66a generally usable and deliverable as previously described. In this embodiment, the ablation catheter 14" includes a resilient, and transversely extending ablating tip portion 20'" and an aperture 562 communicating with a lengthwise lumen in the ablation catheter 14" through which the template wire 66a extends as illustrated in FIG. 45A. In this embodiment, the ablation catheter 14" may be rotated as illustrated in FIGS. 45B, 45C and 45D to engage the surface 12a of the tissue 12 to be ablated. This produces a downward bias creating necessary force with the angled ablating tip portion 20'" against the tissue surface 12a. It will be appreciated that the tip 20'" may be oriented with an angle that is more or less rounded or sharp than that shown for exemplary purposes. As further illustrated in FIGS. 45C and 45D, the resilience and downward bias of the ablating tip portion 20'" helps ensure that any three dimensional variances in the surface 12a of the tissue 12 will be accommodated. That is, the ablating tip portion 20'" will remain forced against the surface 12a of the tissue 12 by reason of the angled and resiliently biased nature of the tip portion 20'".

FIGS. 46A and 46B illustrate an alternative system 600 for ablating internal heart tissue 12. The system 600 generally includes an ablation catheter 14 and a guiding device 610. In this embodiment, the ablation catheter 14 includes a proximal end portion (not shown) positioned outside the patient, and a distal end 18, with the distal end 18 including an ablating tip portion 20 operative to allow selective ablation of tissue 12. This ablation catheter 14 may be a conventional ablation catheter with a tip that creates spot or focal point lesions in a known manner, such as through the use of RF energy. In this example, the guiding device 610 is shown to be temporarily anchored within a pulmonary vein 22, schematically illustrated in cross section, including an opening 22a into the left atrial chamber or atrium 24. For this purpose, a distal tip portion of the guiding device 610 includes a J-shaped or hook-shaped section 612, as well as a coil section 614 that are flexible and biased into engagement with the walls of the vein 22. The guiding device 610 is engageable with the ablation catheter 14, by being coupled therewith via a laterally extending coupling element in the exemplary form of a coiled section 620. In this embodiment, the guiding device 610 more specifically comprises a wire, which may have many different forms and constructions. For example, this wire may be formed from a single integral material, such as biocompatible metals or polymers (e.g., medical grade steel, steel alloys, titanium or superelastic alloys such as nickel-titanium).

This wire device 610, as well as other wires disclosed herein, may alternatively be constructed as a composite, for example, using an outer coil construction over an inner core construction. The materials may be a combination of superelastic and non-superelastic. In any case, the term "wire" as used herein is not meant to denote any particular construction, except that the wire is an elongate element with physical characteristics sufficient to carry out of the functions and use as shown and described herein. As illustrated in FIG. 46B, the ablating tip portion 20 of the catheter 14 is steerable so that it may be flexed into desired positions by the doctor, such as the position shown. The coupling between the guiding device 16 and the ablation catheter 14 allows the ablation catheter 14 to be rotated and moved back and forth along its length within the coupling coil 620 to apply a pattern of ablation forming lesion areas 40 in the tissue 12 surrounding the opening 22a of the pulmonary vein 22. The pattern of ablation may take on various geometric patterns or shapes including closed geometric shapes. In this particular embodiment, the closed geometric shape may be a generally circular shape or pattern of lesions 40 located in a surrounding manner to the opening 22a of the pulmonary vein 22.

Figure 47A:
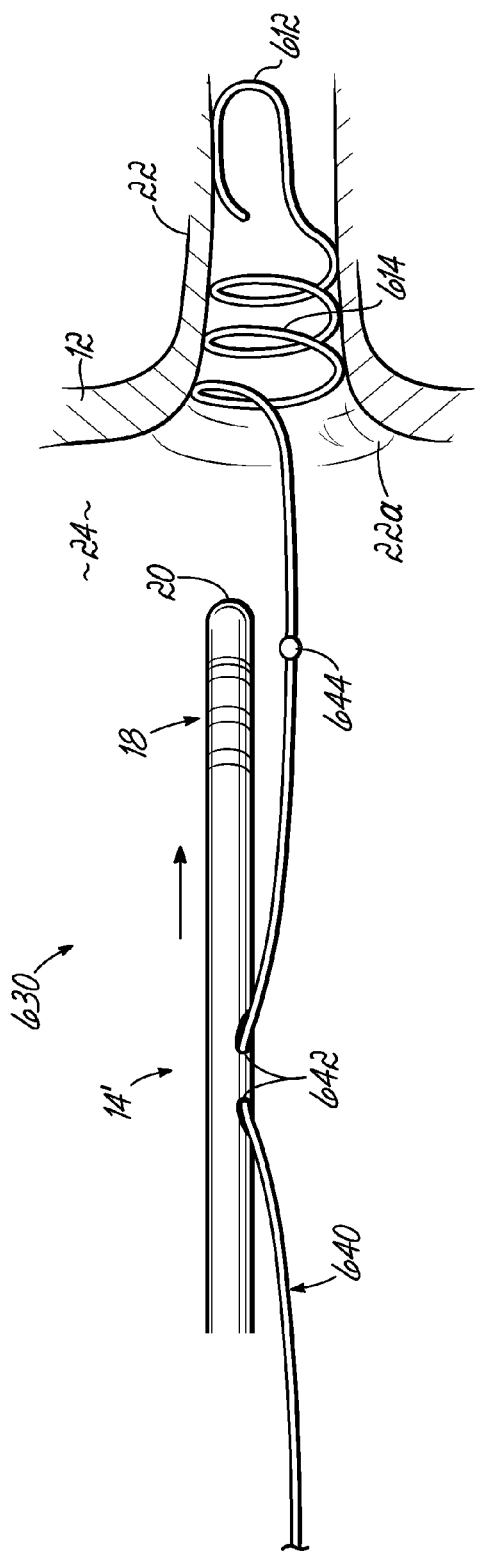
FIG. 47A is a plan view of a system in accordance with a second embodiment of the invention illustrating another type of connection between the ablation catheter and the guiding device.
Figure 47B:
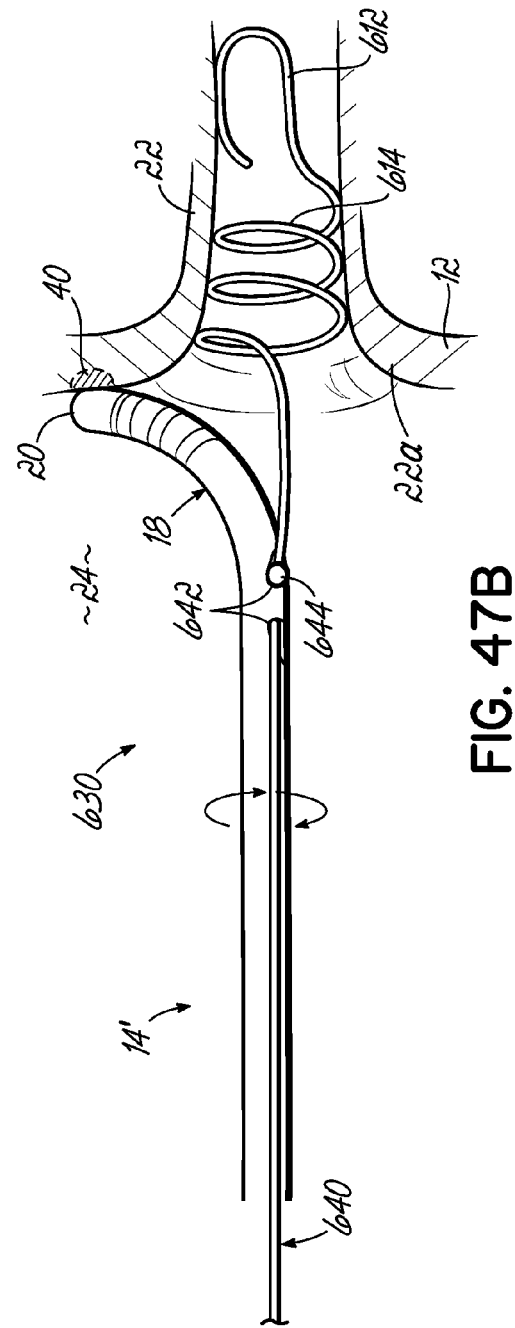
FIG. 47B is a plan view similar to FIG. 47A, but illustrating a subsequent step in the method in which tissue is being ablated in areas surrounding the pulmonary vein.
Figure 48C:
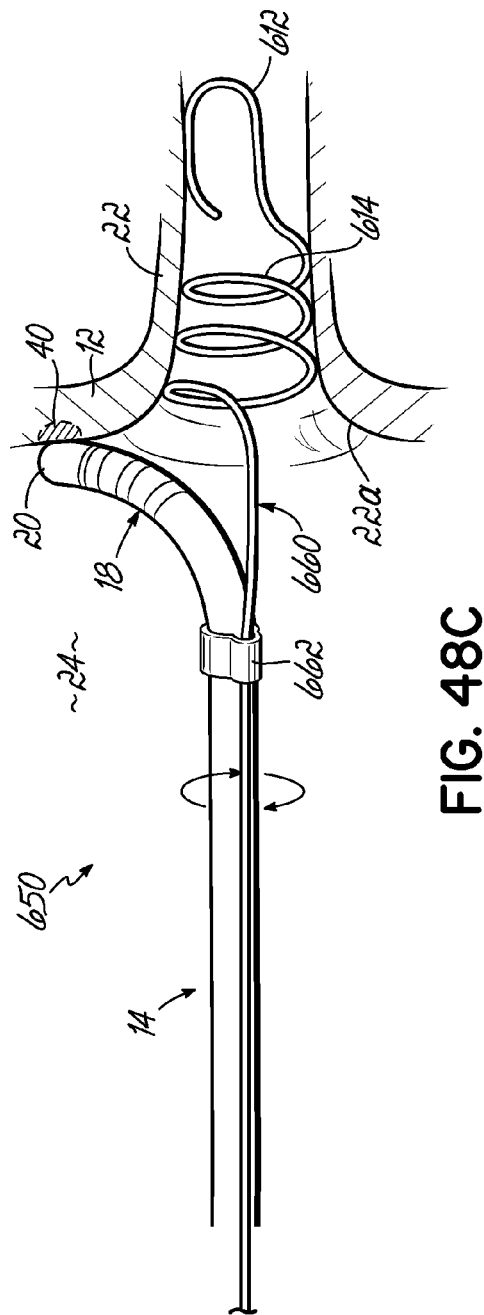
FIG. 48C is a similar view to FIGS. 48A and 48B but illustrating a subsequent portion of the method in which tissue surrounding the pulmonary vein is being ablated with the ablation catheter.

FIGS. 47A and 48B illustrate another embodiment of a system 630 similar to the system 600 illustrated in FIGS. 46A and 46B. In this embodiment, however, the connection or coupling between the guiding device 640 and the ablation catheter 14' comprises structure of the ablation catheter itself, such as an aperture or opening 642 on the catheter 14' that allows the wire of the guiding device 640 to be passed therethrough and allows rotation of the catheter 14' in a manner described in connection with FIGS. 46A and 46B. In this embodiment, the guiding device 640 includes a stop element 644 that engages the ablation catheter 14' as shown in FIG. 47B to stop advancement of the ablation catheter 14' at a location sufficient to apply the spot ablations 40 to the tissue 12 surrounding the opening 22a of the pulmonary vein 22 in the manner described in connection with FIG. 47B.

Figure 48E:
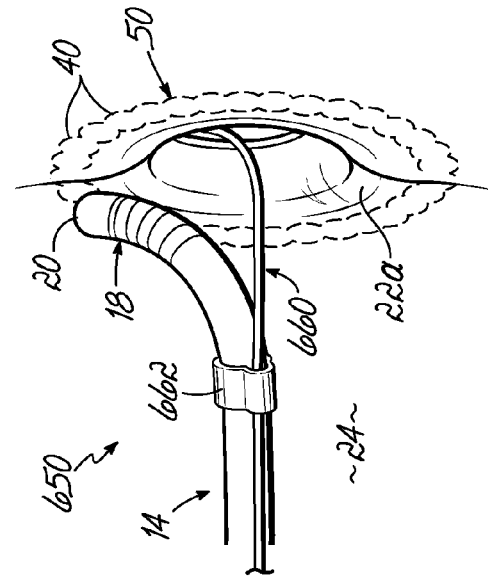
FIG. 48E is a view similar to FIG. 48D but illustrating completion of the ablation pattern into a closed geometric shape surrounding the pulmonary vein.
Figure 48D:
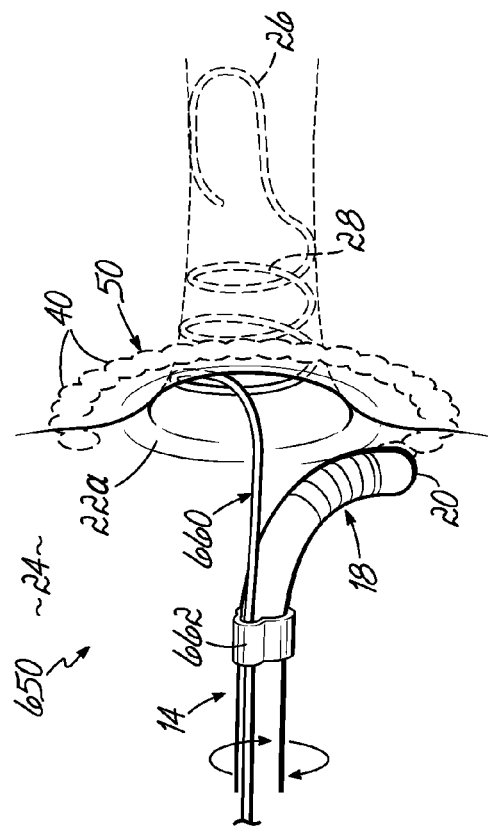
FIG. 48D is a view of the system shown in FIGS. 48A-48C and illustrating a still further portion of the method.

FIGS. 48A-48E illustrate a system 650 in accordance with another embodiment including a guiding device 660 similar to those illustrated in FIGS. 46A, 46B and 47A, 47B but with the guiding device 660 coupled to the ablation catheter 14 with a laterally extending channel connector 662. As further shown in FIGS. 48C-48E, the coupling 662 between the guiding device or wire 660 in this case, and the ablation catheter 14 again allows rotation of the ablation catheter 14 and the ablating tip 20 about or in surrounding fashion to the opening 22a of the pulmonary vein 22 while applying ablation energy, such as spot ablations 40 by appropriately activating the ablation catheter 14. As shown in FIG. 48E, the result can be a closed geometric pattern 670 of lesions 40 surrounding the opening 22a to the pulmonary vein 22 in the interior wall of the atrium 24. It will be appreciated the even though the same reference numerals 40 and 50 are used to refer to the lesions/ablations and patterns thereof, the specific shapes thereof will vary as shown herein, and in many ways not shown herein depending on the needs of the physician.

Figure 49:
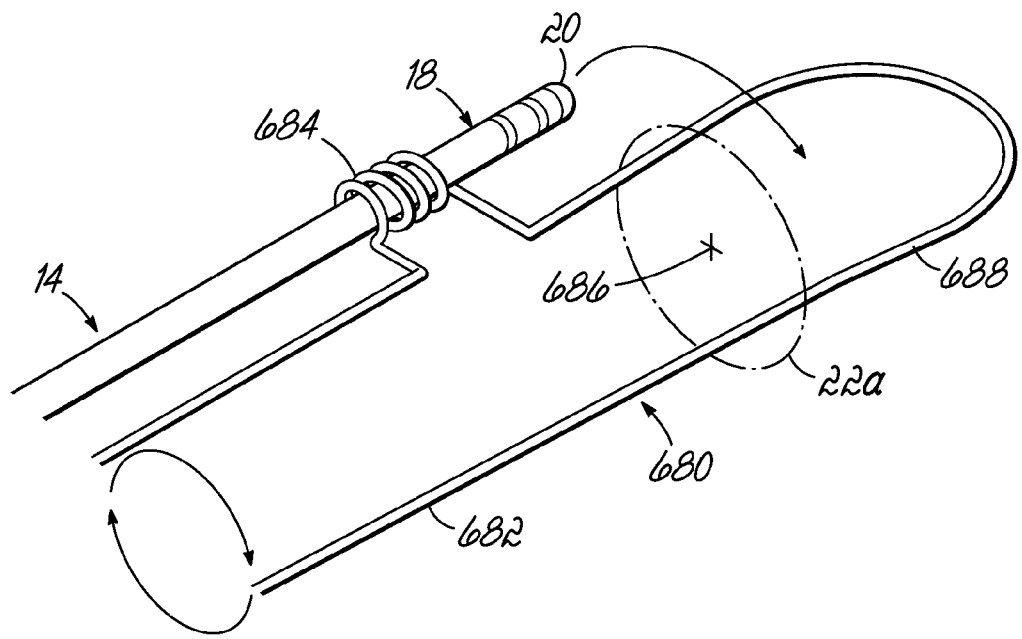
FIG. 49 is a perspective view of a system including a guiding device engaged with an ablation catheter to form a system in accordance with the invention in which the guiding device allows the ablation catheter to be rotated generally about a center point to apply a pattern of ablation.

FIG. 49 illustrates another embodiment of a guiding device 680 comprising a wire 682 coupled to the ablation catheter 14 by a portion of the wire 682. In this case, the coupling portion of the wire is a coil 684 that allows rotation of the ablation catheter 14 generally around a center point 686 when a tissue anchoring portion 688 of the guiding device 680 is suitably anchored. This tissue anchoring portion 688 again comprises a generally U-shaped distal section of wire that is configured to be inserted within a pulmonary vein opening 22a schematically illustrated in dash-dot lines in FIG. 49. The configuration and shape of the guiding device 680 allow the ablation catheter 14 to be rotated around the pulmonary vein opening 22a while ablating tissue in a suitable pattern, such as one of the patterns described herein. The coupling 684 between the guiding device 680 and the ablation catheter 14 further allows the ablation catheter 14 to be moved axially toward and away from the tissue to be ablated thereby allowing the electrophysiologist to apply the requisite amount of ablation force to the tissue. Because of the laterally extending coupling 684, this guiding device 680 and such other devices contemplated herein with similar couplings may be used with conventional or "off-the-shelf" ablation catheters.

Figure 50:
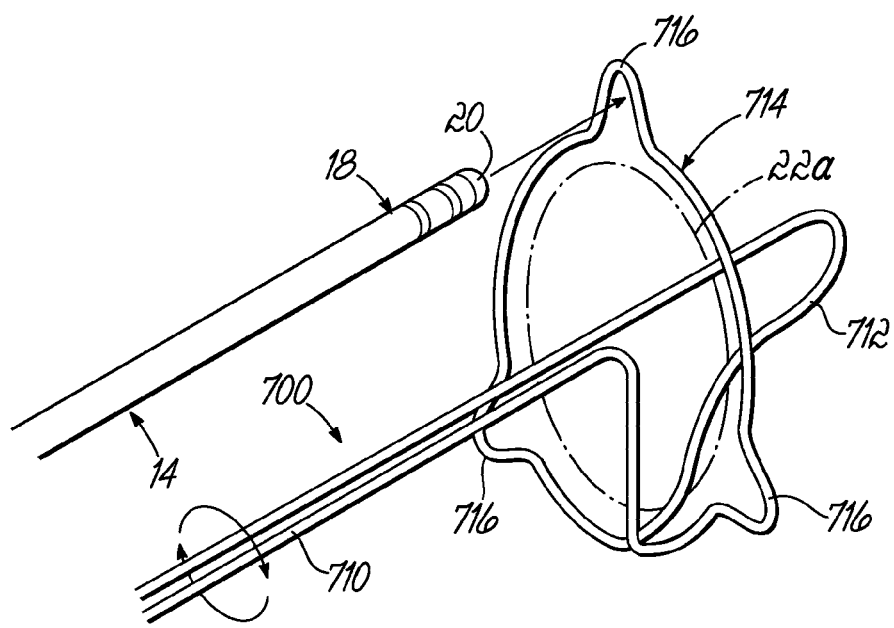
FIG. 50 is a perspective view illustrating a system including a guiding device and an ablation catheter in which the ablating tip portion of the catheter is engaged with the guiding device to apply a pattern of ablation by generally rotating or indexing the ablating tip to apply a pattern of ablation about a center point while rotating the guiding device about that center point.

FIG. 50 illustrates another alternative embodiment of a system 700 including a guiding device 710 comprising a wire structure that includes a generally U-shaped tissue anchoring portion 712 generally as previously described for being temporarily retained or anchored within a pulmonary vein opening, and a closed template portion 714. Like the other embodiments, the template portion 714 of this embodiment extends laterally or transversely relative to a main or lengthwise axis of the wire guiding device 710 at a more proximal location. The template portion 714 couples with the ablating tip portion 20 of an ablation catheter 14 while the ablating tip portion 20 applies a pattern of ablation designed to treat conditions of the heart, such as AF. In this embodiment, the ablating tip portion 20 may be directed within one of three laterally extending receiving sections 716 of the template portion 714 as schematically illustrated and, once received within one of the receiving sections 716, the wire structure or guiding device may be rotated about the center point of the pulmonary vein openings 22a with the ablating tip portion 20 engaged within the receiving section. This results in more controlled movement of the catheter 14. Rotational movements of the catheter 14 and device 710 may be continuous or indexed to apply a generally circular pattern of ablation around or in surrounding relation to the pulmonary vein opening. This may be through spot ablation or one or more continuous segments of ablation as with the other embodiments described herein. Alternatively, additional receiving sections 716 may be added such that device 710 need not be rotated during the ablation. Instead, the tip portion 20 would be removed from one receiving section 716 and moved to another section 716 with sections 716 positioned closely enough to each other to create the closed pattern 50.

While the present invention has been illustrated by a description of various preferred and merely illustrative embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A system for ablating internal heart tissue in an ablation pattern on a surface of the tissue within the heart, the system comprising:
    an ablation catheter including a proximal end and a distal end, the distal end including an ablating tip portion operative to allow selective ablation of tissue, and
    a guiding device engageable with the ablation catheter, the guiding device including a template wire having a proximal portion extending along a lengthwise axis, a template portion located distal to the proximal portion, and a tissue anchoring portion operable to engage with tissue proximate to the tissue to be ablated so as to temporarily anchor the guiding device relative to the tissue to be ablated, wherein the template portion extends laterally relative to the lengthwise axis and is generally shaped to correspond to at least a portion of the ablation pattern, and the template wire and the ablation catheter are respectively configured to allow the ablating tip portion to be guided and moved along the template portion to apply at least a portion of the ablation pattern;
    wherein the template wire and the ablation catheter are coupled together with a direct or indirect connection to allow the ablating tip portion to be guided and moved along the template portion; and
    wherein the template wire further includes the tissue anchoring portion.

2. The system of claim 1, wherein the tissue anchoring portion further comprises a portion configured to extend into and temporarily anchor within a pulmonary vein.

3. The system of claim 1, wherein the guiding device is attached to the ablation catheter in a manner that allows limited movement of the ablating tip portion toward and away from the tissue in order to maintain proper contact with and ablation of three dimensional variations in the tissue surface.

4. The system of claim 1, wherein the template wire is configured into a generally closed geometric shape so that the pattern applied is a closed geometric shape.

5. The system of claim 4, wherein the template wire is configured into a shape for surrounding one or more pulmonary vein locations in the left atrium.

6. The system of claim 1, wherein the template wire carries one or more markers or sensors operative to assist with location and/or testing the effectiveness of the ablation.

7. The system of claim 1, wherein the template wire further comprises a double wire track configured to receive and guide the ablating tip portion between two wire portions of the track.

8. The system of claim 1, wherein the template wire includes a laterally extending coupling for connecting directly to the ablation catheter.

9. A system for ablating internal heart tissue in an ablation pattern on a surface of the tissue within the heart, the system comprising:
    an ablation catheter including a proximal end and a distal end, the distal end including an ablating tip portion operative to allow selective ablation of tissue, and
    a guiding device engageable with the ablation catheter, the guiding device including a template wire having a proximal portion extending along a lengthwise axis, a template portion located distal to the proximal portion, and a tissue anchoring portion operable to engage with tissue proximate to the tissue to be ablated so as to temporarily anchor the guiding device relative to the tissue to be ablated, wherein the template portion extends laterally relative to the lengthwise axis and is generally shaped to correspond to at least a portion of the ablation pattern, and the template wire and the ablation catheter are respectively configured to allow the ablating tip portion to be guided and moved along the template portion to apply at least a portion of the ablation pattern; and
    wherein the ablation catheter further comprises a coupling wire segment actuatable to selectively coil around the template wire in order to couple the ablating tip portion to the template wire in a manner allowing movement of the ablating tip portion relative to the template wire.

10. A system for ablating internal heart tissue in an ablation pattern on a surface of the tissue within the heart, the system comprising:
    an ablation catheter including a proximal end and a distal end, the distal end including an ablating tip portion operative to allow selective ablation of tissue, and
    a guiding device engageable with the ablation catheter, the guiding device including a template wire having a proximal portion extending along a lengthwise axis, a template portion located distal to the proximal portion, and a tissue anchoring portion operable to engage with tissue proximate to the tissue to be ablated so as to temporarily anchor the guiding device relative to the tissue to be ablated, wherein the template portion extends laterally relative to the lengthwise axis and is generally shaped to correspond to at least a portion of the ablation pattern, and the template wire and the ablation catheter are respectively configured to allow the ablating tip portion to be guided and moved along the template portion to apply at least a portion of the ablation pattern;
    wherein the ablation catheter further includes a guide channel and the template wire extends through the guide channel, wherein the ablation catheter is moveable along the template portion to apply at least a portion of the pattern; and
    wherein the template wire is preformed with a three dimensional shape including the tissue anchoring portion and the template portion along which the ablation catheter is guided, and the channel further comprises a lumen extending lengthwise through the ablation catheter, and the template wire transforms from a straightened condition in the lumen of the ablation catheter to the three dimensional shape when the template wire is extended outwardly from a distal end of the ablation catheter.

11. The system of claim 1, wherein the template wire has at least two areas of stiffness along the length thereof that are different from each other at the distal end portion.

12. The system of claim 1, wherein the ablation catheter further includes one or more sensors operative to test the effectiveness of the ablation.

13. The system of claim 1, further comprising:
a motor drive unit operatively coupled to the ablation catheter so as to move the ablating tip portion along the pattern.

14. A percutaneous method of treating the heart of a patient in a manner designed to promote normal sinus rhythm, comprising:
directing an ablation catheter, including a distal end and a lumen extending lengthwise through the ablation catheter, percutaneously into the vascular system including the left atrium of the heart of a patient, the distal end including an ablating tip portion operative to allow selective ablation of tissue,
percutaneously directing a guiding device comprising a template wire, having a lengthwise axis along a proximal portion, and preformed with a three dimensional shape including a tissue anchoring portion and a template portion along which the ablation catheter is guided, into the vascular system and the left atrium of the heart of the patient, the guiding device including a template portion at a location distal to the proximal portion and extending laterally relative to the lengthwise axis;
extending the template wire from the lumen of the ablation catheter to transform the template wire from a straightened condition in the lumen of the ablation catheter to the three dimensional shape including the tissue anchoring portion and the template portion configured to guide the application of at least a portion of the pattern;
temporarily anchoring the guiding device on tissue proximate to the tissue to be ablated, and
guiding the ablating tip portion along the template portion of the guiding device while ablating heart tissue within the left atrium along a pattern designed to promote normal sinus rhythm.

15. A system for ablating internal heart tissue in an ablation pattern on a surface of the tissue within the heart, the system comprising:
an ablation catheter including a proximal end and a distal end, the distal end including an ablating tip portion operative to allow selective ablation of tissue, and
a guiding device engageable with the ablation catheter, the guiding device including a template wire having a proximal portion extending along a lengthwise axis, a template portion located distal to the proximal portion, and a tissue anchoring portion operable to engage with tissue proximate to the tissue to be ablated so as to temporarily anchor the guiding device relative to the tissue to be ablated, wherein the template portion extends laterally relative to the lengthwise axis and is generally shaped to correspond to at least a portion of the ablation pattern, and the template wire and the ablation catheter are respectively configured to allow the ablating tip portion to be guided and moved along the template portion to apply at least a portion of the ablation pattern; and
wherein the distal end of the ablation catheter further comprises a recess configured to receive the template wire for guiding the distal end of the ablation catheter.

* * * * *